(12) United States Patent
Milstein et al.

(10) Patent No.: US 9,290,441 B2
(45) Date of Patent: Mar. 22, 2016

(54) USE OF RUTHENIUM COMPLEXES FOR FORMATION AND/OR HYDROGENATION OF AMIDES AND RELATED CARBOXYLIC ACID DERIVATIVES

(75) Inventors: David Milstein, Rehovot (IL); Chidambaram Gunanathan, Rehovot (IL); Yehoshua Ben-David, Givatayim (IL); Ekambaram Balaraman, Rehovot (IL); Boopathy Gnanaprakasam, Rehovot (IL); Jing Zhang, Rehovot (IL)

(73) Assignee: Yeda Research and Development Co. Ltd., Rehovot (IL)

(*) Notice: Subject to any disclaimer, the term of this patent is extended or adjusted under 35 U.S.C. 154(b) by 546 days.

(21) Appl. No.: 13/471,037

(22) Filed: May 14, 2012

(65) Prior Publication Data

US 2012/0253042 A1    Oct. 4, 2012

Related U.S. Application Data

(63) Continuation of application No. PCT/IL2011/000817, filed on Oct. 11, 2011.

(60) Provisional application No. 61/394,387, filed on Oct. 19, 2010.

(51) Int. Cl.

| | | |
|---|---|---|
| C07C 231/00 | (2006.01) | |
| C07C 209/50 | (2006.01) | |
| C07C 213/00 | (2006.01) | |
| C07C 231/02 | (2006.01) | |
| C07D 307/52 | (2006.01) | |
| C08L 79/02 | (2006.01) | |
| C07C 67/03 | (2006.01) | |
| C07K 1/02 | (2006.01) | |
| C07K 1/10 | (2006.01) | |

(52) U.S. Cl.
CPC .............. *C07C 231/00* (2013.01); *C07C 67/03* (2013.01); *C07C 209/50* (2013.01); *C07C 213/00* (2013.01); *C07C 231/02* (2013.01); *C07D 307/52* (2013.01); *C08L 79/02* (2013.01); *C07C 2101/08* (2013.01); *C07C 2101/14* (2013.01); *C07K 1/02* (2013.01); *C07K 1/10* (2013.01)

(58) Field of Classification Search
CPC .................................................... C07C 231/00
See application file for complete search history.

(56) References Cited

U.S. PATENT DOCUMENTS 7,709,689 B2 * 5/2010 Kilner et al. .................. 568/885

FOREIGN PATENT DOCUMENTS

| EP | 0286280 A1 * | 10/1988 | |
|---|---|---|---|
| WO | WO 03093208 | * 11/2003 | |
| WO | WO 2008035123 A2 * | 3/2008 | ............. C07C 29/149 |

OTHER PUBLICATIONS

Hirosawa "Hydrogenation of Amides by the Use of Bimetallic Catalysts Consisting of Group 8 to 10, and Group 6 or 7 Metals." Tetrahedron Letters, 1996, vol. 37, No. 37, pp. 6749-6752.*
Tillack et al., (2006) A novel ruthenium-catalyzed amination of primary and secondary alcohols Tetrahedron Letters 47: 8881-8885.
Abbenhuis et al., "Ruthenium-Complex-Catalyzed N-(Cyclo)alkylation of Aromatic Amines with Diols. Selective Synthesis of N-(ω-Hydroxyalkyl)anilines of Type PhNH(CH$_2$)$_n$OH and of Some Bioactive Arylpiperazines," J. Org. Chem., 63(13):4282-4290 (1998).
Ben-Ari et al., "Metal—Ligand Cooperation in C—H and H$_2$ Activation by an Electron-Rich PNP Ir(I) System: Facile Ligand Dearomatization—Aromatization as Key Steps," J. Am. Chem. Soc., 128(48):15390-15391 (2006).
Bray, "Large-scale manufacture of peptide therapeutics by chemical synthesis," Nature Reviews Drug Discovery, 2(7):587-593 (2003).
Cassidy et al., "Practical Synthesis of Amides from In Situ Generated Copper(I) Acetylides and Sulfonyl Azides," Angew. Chem. Int. Ed., 45(19):3154-3157 (2006).
Chan et al., "Oxidative amide synthesis and N-terminal alpha-amino group ligation of peptides in aqueous medium," J. Am. Chem. Soc., 128(46):14796-14797 (2006).
Cho et al., "Copper-catalyzed hydrative amide synthesis with terminal alkyne, sulfonyl azide, and water," J. Am. Chem. Soc., 127(46):16046-16047 (2005).
Cobley et al., "Latinum catalysed hydrolytic amidation of unactivated nitriles," Tetrahedron Letters, 41(14):2467-2470 (2000).
Fujita et al., "Synthesis of five-, six-, and seven-membered ring lactams by CpRh complex-catalyzed oxidative N-heterocyclization of amino alcohols," Organic Letters, 6(16):2785-2788 (2004).
Hamid et al., "Ruthenium catalysed N-alkylation of amines with alcohols," Chemical Communications, 2007(7):725-727.
Murahashi et al., "Ruthenium-Catalyzed Amidation of Nitriles with Amines. A Novel, Facile Route to Amides and Polyamides," J. Am. Chem. Soc., 108(14):7846-7847 (1986).
Murahashi et al., "Ruthenium-Catalyzed Hydration of Nitriles and Transformation of δ-Keto Nitriles to Ene-Lactams,". J. Org. Chem., 57(9):2521-2523 (1992).

(Continued)

*Primary Examiner* — David K O Dell
(74) *Attorney, Agent, or Firm* — Winston & Strawn LLP

(57) ABSTRACT

A process for preparing amides by reacting a primary amine and a primary alcohol in the presence of a Ruthenium complex to generate the amide and molecular hydrogen. Primary amines are directly acylated by equimolar amounts of alcohols to produce amides and molecular hydrogen (the only byproduct) in high yields and high turnover numbers. Also disclosed are processes for hydrogenation of amides to alcohols and amines; hydrogenation of organic carbonates to alcohols; hydrogenation of carbamates or urea derivatives to alcohols and amines; amidation of esters; acylation of alcohols using esters; coupling of alcohols with water and a base to form carboxylic acids; dehydrogenation of beta-amino alcohols to form pyrazines and cyclic dipeptides; and dehydrogenation of secondary alcohols to ketones. These reactions are catalyzed by a Ruthenium complex which is based on a dearomatized PNN-type ligand of formula A1 or precursors thereof of formulae A2 or A3.

22 Claims, 7 Drawing Sheets

(56) References Cited

OTHER PUBLICATIONS

Naota et al., "Ruthenium-Catalyzed Transformations of Amino Alcohols to Lactams," Synlett, 1991(10):693-694.

Owston et al., "Iridium-Catalyzed Conversion of Alcohols into Amides via Oximes," Organic Letters, 9(1):73-75 (2007).

Rannard et al., "The Selective Reaction of Primary Amines with Carbonyl Imidazole Containing Compounds: Selective Amide and Carbamate Synthesis," Organic Letters, 2(14):2117-2120 (2000).

Tamaru et al., "Direct Oxidative Transformation of Aldehydes to Amides by Palladium Catalysis," Synthesis, 6:474-476 (1983).

Tillack et al., "Catalytic Amination of Aldehydes to Amides," Eur. J. Org. Chem., 2001(3):523-528 (Feb. 2001).

Watanabe et al., "Ruthenium-Catalyzed N-Alkylation and N-Benzylation of Aminoarenes with Alcohols," J. Org. Chem., 49(18):3359-3363 (1984).

Williams et al., "Variable NMR Spin-Lattice Relaxation Times in Secondary Amides: Effect of Ramachandran Angles on the Librational Dynamics," J. Phys. Chem. B, 102:6248-6259 (1998).

Zhang et al., "Electron-Rich, Bulky Ruthenium PNP-Type Complexes. Acceptorless Catalytic Alcohol Dehydrogenation," Organometallics, 23(17):4026-4033 (2004).

Zhang et al., "Facile Conversion of Alcohols into Esters and Dihydrogen Catalyzed by New Ruthenium Complexes," J. Am. Chem. Soc. 127(31):10840-10841 (2005).

Zhang et al., "Efficient Homogeneous Catalytic Hydrogenation of Esters to Alcohols," Angew. Chem. Int. Ed., 45(7):1113-1115 (2006).

Zhang et al., "Electron-rich, bulky PNN-type ruthenium complexes: synthesis, characterization and catalysis of alcohol dehydrogenation," Dalton Transactions, 2007(1):107-113.

\* cited by examiner

USE OF RUTHENIUM COMPLEXES FOR FORMATION AND/OR HYDROGENATION OF AMIDES AND RELATED CARBOXYLIC ACID DERIVATIVES

CROSS-REFERENCE TO RELATED APPLICATIONS

This application is a continuation of International application PCT/IL2011/000817 filed Oct. 11, 2011, which claims the benefit of U.S. provisional application No. 61/394,387 filed Oct. 19, 2010. The entire content of each listed application is expressly incorporated herein by reference thereto.

FIELD OF THE INVENTION

The present invention relates to processes for (1) preparing amides by reacting alcohols with amines (including the preparation of polyamides (e.g., polypeptides) by reacting dialcohols and diamines and/or by polymerization of amino alcohols); (2) hydrogenation of amides (including polyamides) to alcohols and amines; (3) hydrogenation of organic carbonates (including polycarbonates) to alcohols and hydrogenation of carbamates (including polycarbamates) or urea derivatives to alcohols and amines; (4) amidation of esters (i.e., synthesis of amides from esters and amines; (5) acylation of alcohols using esters; (6) coupling of alcohols with water and a base to form carboxylic acids; (7) dehydrogenation of beta-amino alcohols to form pyrazines; and (8) dehydrogenation of secondary alcohols to ketones. The aforementioned processes are conducted in the presence of Ruthenium complexes as described herein.

BACKGROUND OF THE INVENTION

Amide formation is a fundamental reaction in chemical synthesis (1). The importance of amides in chemistry and biology is well recognized and has been studied extensively over the past century (2-4). Although several methods are known for the synthesis of amides, preparation under neutral conditions and without generation of waste is a challenging goal (1, 5). Synthesis of amides is mostly based on activated acid derivatives (acid chlorides, anhydrides) or rearrangement reactions induced by acid or base which often involve toxic chemical waste and tedious work-up (5). Transition-metal catalyzed conversion of nitriles into amides was reported (6, 7, 8). Catalytic acylation of amines by aldehydes in the presence of a stoichiometric amount of oxidant and a base is known (9, 10). Recently, oxidative amide synthesis was achieved from terminal alkynes (11). Cu(I) catalyzed reaction of sulfonyl azides with terminal alkynes is a facile method for the synthesis of sulfonyl amides (12, 13).

Polyamides are one of the most important polymer classes, extensively used in fiber products, plastics and their derivatives, with many applications, including in biomedical studies. Recently, the synthesis of functional polyamides has received considerable attention. Generally, polyamides are synthesized by condensation of diamines and activated dicarboxylic acid derivatives and/or in the presence of coupling reagents. In some cases, ring opening of small-ring lactams at high temperatures leads to polyamides. To avoid the use of activators, waste generation, or harsh conditions, the development of economical, efficient and environmentally benign protocols are desirable.

The reverse reactions, i.e., reduction of amides and related carboxylic acid derivatives plays an important role in organic synthesis, both in laboratory and industrial processes. Traditionally, the reduction is performed using stoichiometric amounts of hydride reagents, generating stoichiometric amounts of waste (14). A much more attractive, atom-economical approach is a catalytic reaction using $H_2$; however, hydrogenation of carboxylic acid derivatives under mild conditions is a very challenging task (15a-b), with amides presenting the one of the highest challenges among all classes of carbonyl compounds. A few examples of the important hydrogenation of amides to amines, in which the C—O bond is cleaved with the liberation of water (Scheme 1), were reported (16a-d). This reaction can also be affected with silanes as reducing agents (17a-b). In addition, the interesting hydrogenation of cyclic N-acylcarbamates and N-acylsulfonamides, which involves cleavage of the C—N bond, but does not form amines, was recently reported (18).

On the other hand, selective, direct hydrogenation of amides to form amines and alcohols has not been reported. Hydrogenation of amides to amines (via C—O cleavage, generating water) can have C—N cleavage as a side reaction, requiring the presence of water, and resulting from catalytic hydrolysis of the amides to acids and amines, followed by hydrogenation of the acids to alcohols (16b-d) However, no amide C—N hydrogenolysis to form alcohols and amines was reported in the absence of water.

Amines and alcohols are used extensively in the chemical, pharmaceutical and agrichemical industries (19a-c). Design of such a reaction is conceptually challenging, since the first mechanistic step in amide hydrogenation is expected to be $H_2$ addition to the carbonyl group to form a very unstable hemiaminal which, in the case of primary or secondary amides, spontaneously liberates water to form an imine; further hydrogenation of the imine then leads to amine formation (Scheme 1). For amine and alcohol formation, cleavage of the C—N bond in preference to the C—O bond is required.

Scheme 1. General scheme for hydrogenation of amides.

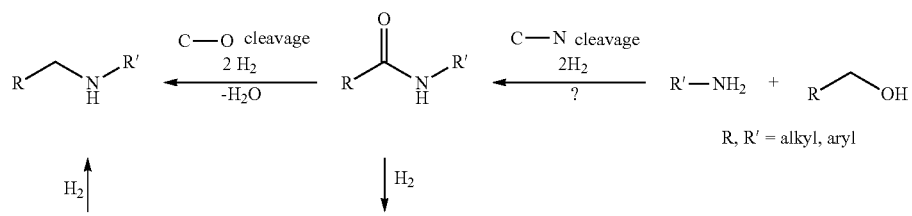

-continued

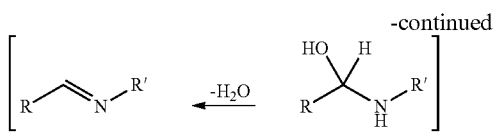

The applicants of the present invention recently reported the dehydrogenation of alcohols catalyzed by PNP- and PNN-Ru (II) hydride complexes (20). Whereas secondary alcohols lead to ketones (21, 22), primary alcohols are efficiently converted into esters and dihydrogen (20-22). The dearomatized PNN pincer complex 1 (FIG. 1) is particularly efficient (23); it catalyzes this process in high yields under neutral conditions, in the absence of acceptors or promoters.

Given the widespread importance of amines, alcohols, amides, and related derivatives in biochemical and chemical systems, efficient syntheses that avoid the shortcomings of prior art processes are highly desirable.

SUMMARY OF THE INVENTION

The present invention relates to processes for (1) preparing amides by reacting alcohols with amines (including the preparation of polyamides (e.g., polypeptides) by reacting dialcohols and diamines and/or by polymerization of amino alcohols); (2) hydrogenation of amides (including polyamides) to alcohols and amines; (3) hydrogenation of organic carbonates (including polycarbonates) to alcohols and hydrogenation of carbamates (including polycarbamates) or urea derivatives to alcohols and amines; (4) amidation of esters (i.e., synthesis of amides from esters and amines; (5) acylation of alcohols using esters (6) coupling of alcohols with water and a base to form carboxylic acids; (7) dehydrogenation of beta-amino alcohols to form pyrazines; and (8) dehydrogenation of secondary alcohols to ketones. The aforementioned processes are conducted in the presence of Ruthenium complexes as described herein.

In one embodiment, the present invention provides a process for preparing amides, by reacting a primary amine and a primary alcohol in the presence of a Ruthenium catalyst, to generate the amide and molecular hydrogen. As contemplated herein, the inventors have discovered a novel process for preparing amides in which primary amines are directly acylated by equimolar amounts of alcohols to produce amides and molecular hydrogen (the only byproduct) in high yields and high turnover numbers. This reaction is catalyzed by a Ruthenium complex, which is preferably based on a dearomatized PNN-type ligand, requiring no base or acid promoters, or is based on an aromatized precursor of the dearomatized PNN-type ligand, with the optional use of one or more equivalents of a base. Use of primary diamines in the reaction leads to bis-amides, whereas with a mixed primary/secondary amine substrate, chemoselective acylation of the primary amine group occurs.

The process of the invention, i.e., the direct catalytic conversion of alcohols and amines into amides and dihydrogen is illustrated in Scheme 2. This novel, environmentally benign reaction (24-28), can be used to produce various amides from very simple substrates, with high atom economy and in some embodiments no stoichiometric activating agents, thus generating no waste. Although such a reaction is expected to be thermodynamically uphill, it is contemplated that the liberated hydrogen gas will shift the equilibrium and will drive the reaction.

Scheme 2

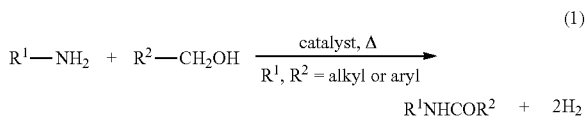

wherein $R^1$ and $R^2$ can be the same or different from each other.

The applicants of the present invention have unexpectedly discovered that Ruthenium complexes catalyze the reaction of alcohols with amines to form amides and $H_2$.

In one embodiment, the Ruthenium complex is represented by any one of formulae A1, A2 or A3:

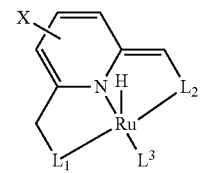

A1

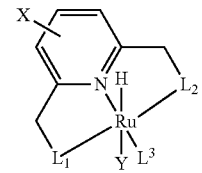

A2

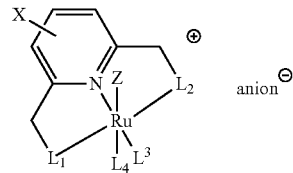

A3 wherein
$L_1$ and $L_2$ are each independently selected from the group consisting of nucleophilic carbene (:CR$_2$), P(R)$_2$, P(OR)$_2$, N(R)$_2$, imine, SR, SH, S(=O)R, heteroaryl wherein the heteroatom is selected from nitrogen and sulfur, As(R)$_2$, Sb(R)$_2$ and an N-heterocyclic carbene represented by the structure:

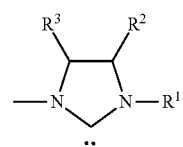

wherein each of R, $R^1$, $R^2$ and $R^3$ is independently selected from the group consisting of alkyl, cycloalkyl, aryl, alkylaryl, heterocyclyl and heteroaryl;

$L_3$ is a mono-dentate two-electron donor selected from the group consisting of CO, $P(R)_3$, $P(OR)_3$, $NO^+$, $As(R)_3$, $Sb(R)_3$, $S(R)_2$, nitrile (RCN) and isonitrile (RNC) wherein R is as defined above;

$L_4$ is absent or is $L_3$;

Y and Z are each independently H or an anionic ligand such as halogen, OCOR, $OCOCF_3$, $OSO_2R$, $OSO_2CF_3$, CN, OH, OR, $N(R)_2$, RS or SH, wherein R is as defined above;

X represents zero, one, two or three substituents selected from the group consisting of alkyl, aryl, halogen, nitro, amide, ester, cyano, alkoxy, cycloalkyl, alkylaryl, heterocyclyl, heteroaryl, an inorganic support (e.g., silica) and a polymeric moiety (e.g., polystyrene); and anion represents a group bearing a single negative charge.

Embodiments wherein two substituents are connected to form a fused ring system (including fused aromatic structures), are also included within the scope of the invention.

In one embodiment, the Ruthenium complex is represented by the structure of formula A1:

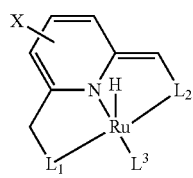

A1

In a particular embodiment of formula A1, the Ruthenium complex is represented by the structure of formula B1:

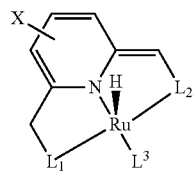

B1

In another particular embodiment of formula A1, the Ruthenium complex is represented by the structure of formula C1:

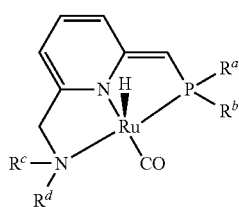

C1 wherein each of $R^a$, $R^b$, $R^c$ and $R^d$ is independently selected from the group consisting of alkyl, cycloalkyl, aryl, alkylaryl, heterocyclyl and heteroaryl.

In one currently preferred embodiment, each of $R^a$ and $R^b$ is tert-butyl. In another currently preferred embodiment, each of $R^c$ and $R^d$ are ethyl. In a particularly preferred embodiment, the Ruthenium complex is represented by the structure of formula 1 (FIG. 1).

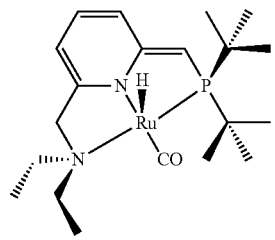

1

When the Ruthenium complex is a compound of formula A1, the process of the invention does not require the addition of any base or acid promoters.

In another embodiment of the present invention, the Ruthenium complex is represented by the structure of formula A2:

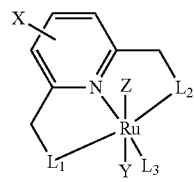

A2 wherein Y and Z are each independently H or an anionic ligand such as halogen, OCOR, $OCOCF_3$, $OSO_2R$, $OSO_2CF_3$, CN, OH, OR, $N(R_2)$, SR or SH, and R is alkyl, cycloalkyl, aryl, alkylaryl, heterocyclyl or heteroaryl.

In one particular embodiment, Z is H and Y is other than H in formula A2. In accordance with this embodiment, the process of the invention is conducted in the presence of at least one equivalent of a base relative to the Ruthenium complex. In another particular embodiment, each of Z and Y is other than H in formula A2. In accordance with this embodiment, the process of the invention is conducted in the presence of at least two equivalents of a base relative to the Ruthenium complex. In another particular embodiment, Z and Y are both H in formula A2. In accordance with this embodiment, no base is required for the process of the invention.

In one embodiment of formula A2, the Ruthenium complex is represented by the structure of formula B2:

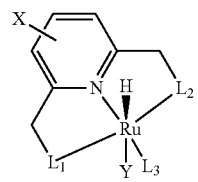

B2 wherein Y is H or an anionic ligand such as halogen OCOR, $OCOCF_3$, $OSO_2R$, $OSO_2CF_3$, CN, OH, OR, $N(R)_2$, SR or SH, and R is alkyl, cycloalkyl, aryl, alkylaryl, heterocyclyl or heteroaryl.

In another particular embodiment of formula A2, the Ruthenium complex is represented by the following structure of formula C2:

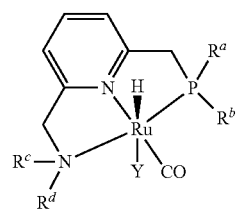

C2 wherein each of $R^a$, $R^b$, $R^c$ and $R^d$ is independently selected from the group consisting of alkyl, cycloalkyl, aryl, alkylaryl, heterocyclyl and heteroaryl.

In one currently preferred embodiment, Y is halogen, such as chloro. A currently preferred complex is a Ruthenium complex is represented by the structure of formula 2:

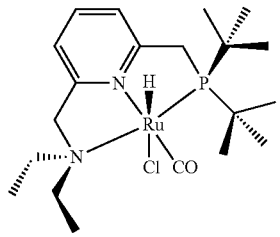

2

In another embodiment of the present invention, the Ruthenium complex is represented by the structure of formula A3:

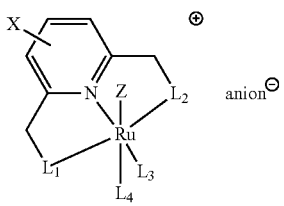

A3 wherein Z is H or an anionic ligand such as halogen, OCOR, OCOCF$_3$, OSO$_2$R, OSO$_2$CF$_3$, CN, OH, OR, N(R)$_2$, SH or SR, R is alkyl, cycloalkyl, aryl, alkylaryl, heterocyclyl or heteroaryl; and L$_4$ is either absent or is a mono-dentate two-electron donor selected from the group consisting of CO, PR$_3$, P(OR)$_3$, NO$^+$, As(R)$_3$, Sb(R)$_3$, S(R)$_2$, nitrile (RCN) and isonitrile (RNC) wherein R is as defined above.

In one particular embodiment, Z is H in formula A3. In accordance with this embodiment, the process is conducted in the presence of at least one equivalent of a base relative to the Ruthenium complex. In another particular embodiment, Z is other than H in formula A3. In accordance with this embodiment, the process is conducted in the presence of at least two equivalents of a base relative to the Ruthenium complex.

Compounds of formula A2 (of which Compound 2 is a representative) and formula A3 are precursors of compounds of formula A1. Additional exemplary precursors of the complexes of formula A1 include, but are not limited to:

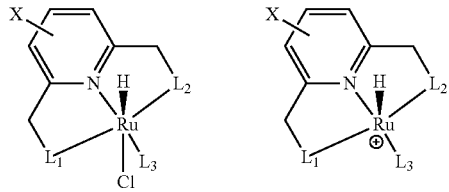

plus at least one equivalent
of base relative to Ru
(e.g. alkoxide, hydroxide)

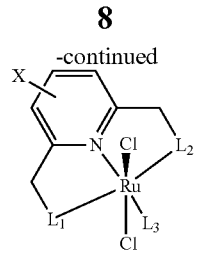

plus at least two equivalents
of base relative to Ru
(e.g. alkoxide, hydroxide)

It is understood that any one or more of the precursors can themselves function as catalysts in the process of the present invention.

A variety of primary alcohols can be used in the process of the invention. In one embodiment, the alcohol is represented by the formula $R^4CH_2OH$ wherein $R^4$ is selected from the group consisting of alkyl, alkoxyalkyl, cycloalkyl, aryl, alkylaryl, heterocyclyl and heteroaryl. In several exemplary embodiments, the alcohol is selected from the group consisting of ethanol, propanol, butanol, pentanol, hexanol, 2-methoxyethanol, and 2-methyl-1-butanol.

A variety of primary amines may be used in the process of the invention. In one embodiment, the amine is represented by the formula $R^5CH_2NH_2$ wherein $R^5$ is selected from the group consisting of alkyl, alkoxyalkyl, cycloalkyl, aryl, alkylaryl, heterocyclyl and heteroaryl. In several exemplary embodiments, the amine is selected from the group consisting of benzylamine, 1-(2-furyl)methylamine, aniline, pentylamine, 2-methylhexylamine, and cyclohexylamine.

In another embodiment, the process of the invention can also be applied to bis-acylation reactions with diamines. Upon reacting alcohols and diamines, the corresponding bis-amides are produced in high yields. In exemplary embodiments, the diamine is ethylenediamine or 1,6-diaminohexane.

Furthermore, it has been discovered that the amidation reactions have a high preference to primary amines. The high selectivity of the dehydrogenative amidation reaction to primary amine functionalities enables the direct bis-acylation of triamines such as diethylelentriamine to produce a diamide by reaction of the two primary amine functionalities.

The reaction between the amine and alcohol can be intermolecular (i.e., the amine and the alcohol are present in separate molecules). Alternatively, the reaction between the amine and alcohol can be intra-molecular, i.e., the amine and alcohol functionalities can be present in the same molecule, resulting in intra-molecular cyclization to generate a lactam. Without wishing to be bound by any theory or mechanism, it is contemplated that the mechanism of the amidation process involves dehydrogenation of hemiaminal intermediates formed by reaction of an aldehyde intermediate with the amine.

In another aspect, the present invention further provides a process for preparing polyamides and polypeptides, by reacting amines and an alcohol in the presence of the Ruthenium complexes described herein, to generate the polyamide or polypeptide and molecular hydrogen (H$_2$).

The aforementioned amidation or polyamidation reactions (including the coupling of beta-amino alcohols to form polypeptides or cyclic peptides), are catalyzed by the Ruthenium complexes of formula A1, A2 and A3, wherein L$_1$ is N(R)$_2$ (designated herein compounds A1', A2' and A3', respectively). One embodiment of such compounds is a pincer complex represented by the structure of formula 1 (FIG. 1). In some embodiments, beta-amino alcohols can be dehydrogenated to form cyclic dipeptides in the presence of Ruthenium complexes of formula A1', A2' and A3' as described herein. Each possibility represents a separate embodiment of the present invention.

In another aspect, the present invention provides a process for hydrogenating amides (including polyamides and polypeptides) by reacting the amide with molecular hydrogen ($H_2$) in the presence of the Ruthenium complex described herein, to generate the corresponding alcohol and amine. As contemplated herein, the inventors have discovered a novel process for converting amides to alcohols and amines in high yields and high turnover numbers. This reaction is catalyzed by the Ruthenium complexes of formula A1', A2' and A3' as described herein. One embodiment of such compounds is a pincer complex represented by the structure of formula 1 (FIG. 1). In a similar manner, lactams (cyclic amides) can be hydrogenated to the corresponding amino alcohols. In addition, polyamides and/or polypeptides can be hydrogenated to the corresponding alcohols and amines. Each possibility represents a separate embodiment of the present invention.

Similar to the hydrogenation of amides, the Ruthenium complexes of the present invention can also catalyze the hydrogenation of organic carbonates to alcohols, or the hydrogenation of carbamates to the corresponding amines and alcohols, or the hydrogenation of urea derivatives to the corresponding amines and methanol. Thus, in other embodiments, the present invention further provides a process for hydrogenating an organic carbonate, carbamate or urea derivative, with molecular hydrogen ($H_2$) in the presence of the Ruthenium complexes described herein. As contemplated herein, the inventors have further discovered a novel process for converting organic carbonates, carbamates or urea derivatives to alcohols and/or amines in high yields and high turnover numbers. Polycarbonates, polycarbamates and/or polyureas can be hydrogenated in a similar manner. These reactions are catalyzed by any of the Ruthenium complexes of formula A1', A2' and A3' as described herein. One embodiment of such compounds is a pincer complex represented by the structure of formula 1 (FIG. 1). Each possibility represents a separate embodiment of the present invention.

In other embodiments, beta-amino alcohols can be dehydrogenated in the presence of Ruthenium complexes to form pyrazines. These reactions are catalyzed by any of the Ruthenium complexes of formula A1, A2 and A3, which contain two phosphine ligands or N-heterocyclic carbene ligands (designated herein compounds A1", A2" and A3", respectively). One embodiment of such compounds is a pincer complex represented by the structure of formula 3 (FIG. 3). Each possibility represents a separate embodiment of the present invention.

The present invention further provides a process for preparing amides, by reacting an amine and an ester in the presence of a Ruthenium complex, to generate the amide compound and molecular hydrogen ($H_2$). This reaction is catalyzed by a Ruthenium complex which is represented by any one of formulae A1', A2' or A3' as defined herein. One embodiment of such compounds is a pincer complex represented by the structure of formula 1 (FIG. 1). In a similar manner, reactions of esters with diamines leads to diamides.

The present invention further provides a process for preparing esters by acylation of alcohols using esters in the presence of a Ruthenium complex, to generate the ester compound and molecular hydrogen. In one embodiment, the process involves reaction of primary alcohols and esters. In another embodiment, the process involves reaction of a secondary alcohols and esters. These reactions are catalyzed by a Ruthenium complex which is represented by any one of formulae A1, A2 or A3 as defined herein. One embodiment of such compounds is a pincer complex represented by the structure of formula 1 (FIG. 1).

The present invention further relates to a process for the coupling of alcohols with water and a base to form carboxylic acid salts, by contacting the alcohol and a base with water in the presence of the Ruthenium complex of formula A1, A2 and A3, and especially Pincer complex of Formula 1 (FIG. 1). Each possibility represents a separate embodiment of the present invention.

The present invention further relates to a process for preparing a ketone by dehydrogenation of a secondary alcohol, by reacting the secondary alcohol in the presence of the Ruthenium complex, thereby generating the ketone and molecular hydrogen. These reactions are catalyzed by a Ruthenium complex which is represented by any one of formulae A1, A2 or A3 as defined herein. One embodiment of such compounds is a pincer complex represented by the structure of formula 1 (FIG. 1).

Depending on the complex being used in each of the aforementioned processes, the reaction permits the optional use of one or more equivalents of a base. Each possibility represents a separate embodiment of the present invention.

In some embodiments, the process of any of the embodiments of the present invention as described herein is conducted under neat conditions in the absence of a solvent. In other embodiments, however, the process is conducted in the presence of an organic solvent such as, but not limited to benzene, toluene, o-, m- or p-xylene, mesitylene (1,3,5-trimethyl benzene), dioxane, THF, DME, anisole and cyclohexane.

In some embodiments the process is conducted under heat. In other embodiments, the process is conducted under inert gas. In other embodiments, the process is conducted under heat and under inert gas. However, the reactions of the invention can, when appropriate, also be conducted in the open air.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will be understood and appreciated more fully from the following detailed description taken in conjunction with the appended figures:

FIG. 4: shows MALDI-TOF mass spectra of polyamides synthesized by the processes of the present invention.

DETAILED DESCRIPTION OF THE PRESENT INVENTION

Figure 1:
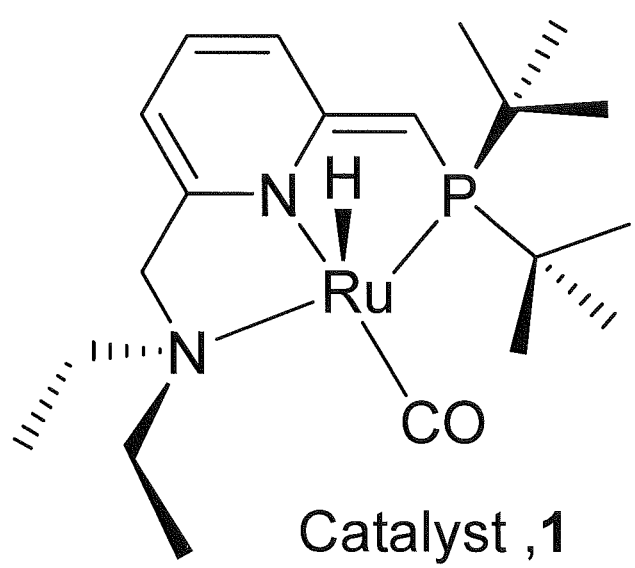
FIG. 1: shows the structure of dearomatized PNN pincer complex 1.

The present invention relates to processes for (1) preparing amides by reacting alcohols with amines (including the preparation of polyamides (e.g., polypeptides) by reacting dialcohols and diamines and/or by polymerization of amino alcohols); (2) hydrogenation of amides (including polyamides) to alcohols and amines; (3) hydrogenation of organic carbonates (including polycarbonates) to alcohols and hydrogenation of carbamates (including polycarbamates) or urea derivatives to alcohols and amines; (4) amidation of esters (i.e., synthesis of amides from esters and amines); (5) acylation of alcohols using esters (6) coupling of alcohols with water and a base to form carboxylic acids; (7) dehydrogenation of beta-amino alcohols to form pyrazines; and (8) dehydrogenation of secondary alcohols to ketones. The aforementioned processes are conducted in the presence of Ruthenium complexes as described herein.

Ruthenium Complexes

In one embodiment, the Ruthenium complex is represented by any one of formulae A1, A2 or A3:

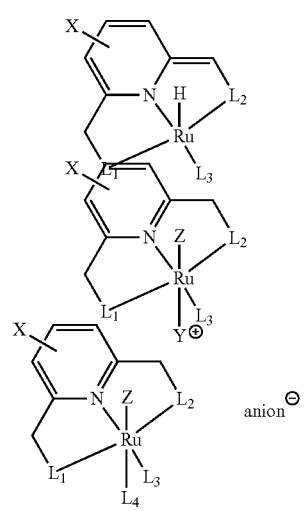

wherein
$L_1$ and $L_2$ are each independently selected from the group consisting of nucleophilic carbene (:CR$_2$), phosphide (P(R)$_2$), P(OR)$_2$, amine (N(R)$_2$), imine, sulfide (SR), thiolate (SH), sulfoxide (S(=O)R), heteroaryl wherein the heteroatom is selected from nitrogen and sulfur, arsine (As(R)$_2$), stibine (Sb(R)$_2$) and an N-heterocyclic carbene represented by the structure:

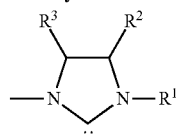

wherein each of R, $R^1$, $R^2$ and $R^3$ is independently selected from the group consisting of alkyl, cycloalkyl, aryl, alkylaryl, heterocyclyl and heteroaryl;
$L_3$ is a mono-dentate two-electron donor selected from the group consisting of CO, P(R)$_3$, P(OR)$_3$, NO$^+$, As(R)$_3$, Sb(R)$_3$, S(R)$_2$, nitrile (RCN) and isonitrile (RNC) wherein R is as defined above;
$L_4$ is absent or is $L_3$;

Y and Z are each independently H or an anionic ligand such as (but not limited to) halogen, OCOR, OCOCF$_3$, OSO$_2$R, OSO$_2$CF$_3$, CN, OH, OR, N(R)$_2$, RS or SH, wherein R is as defined above;

X represents zero, one, two or three substituents selected from the group consisting of alkyl, aryl, halogen, nitro, amide, ester, cyano, alkoxy, cycloalkyl, alkylaryl, heterocyclyl, heteroaryl, an inorganic support (e.g., silica) and a polymeric moiety (e.g., polystyrene); and anion represents a group bearing a single negative charge.

It is understood that when a phosphide group (P(R)$_2$) as defined above is attached to the carbon atom in the Ruthenium complex of the invention, it is designated a "phosphine" group.

It is further understood that Y and Z are not limited to the aforementioned groups, and that any other anionic ligands can be used and would be encompassed within the scope of the invention.

Embodiments wherein two substituents are connected to form a fused ring system (including fused aromatic structures), are also included within the scope of the invention.

In one embodiment, the Ruthenium complex is represented by the structure of formula A1:

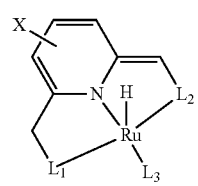

In a particular embodiment of formula A1, the Ruthenium complex is represented by the structure of formula B1:

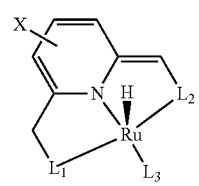

In another particular embodiment of formula A1, the complex is represented by the structure of formula C1:

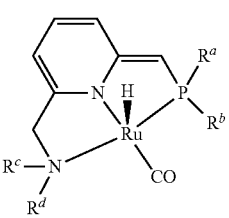

wherein each of $R^a$, $R^b$, $R^c$ and $R^d$ is independently selected from the group consisting of alkyl, cycloalkyl, aryl, alkylaryl, heterocyclyl and heteroaryl.

Figure 3:
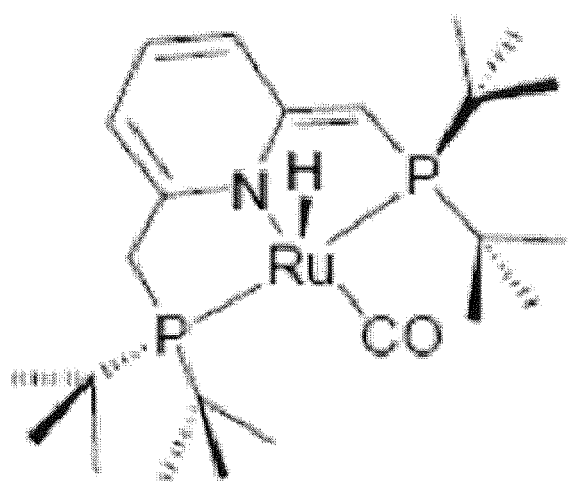
FIG. 3: shows the structure of an aromatized PNP pincer complex 3.

In one currently preferred embodiment, each of $R^a$ and $R^b$ is tert-butyl. In another currently preferred embodiment, each of $R^c$ and $R^d$ are ethyl. In one preferred embodiment, the Ruthenium complex is represented by the structure of formula 1 (FIG. 1). In another preferred embodiment, the Ruthenium complex is represented by the structure of formula 3 (FIG. 3).

In some embodiments, the Ruthenium complex acts as a catalyst (and is thus designated "Ruthenium catalyst").

The Ruthenium complex of formula A1 is neutral. Furthermore, when a Ruthenium complex of formula A1 is used, the process of the invention does not require the addition of any base or acid promoters.

In another embodiment of the present invention, the Ruthenium complex is represented by the structure of formula A2:

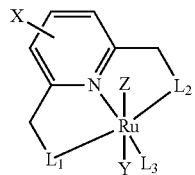

A2 wherein Y and Z are each independently H or an anionic ligand such as (but not limited to) halogen, OCOR, OCOCF$_3$, OSO$_2$R, OSO$_2$CF$_3$, CN, OH, OR, N(R)$_2$, SR or SH, and R is alkyl, cycloalkyl, aryl, alkylaryl, heterocyclyl or heteroaryl.

In one particular embodiment, Z is H and Y is other than H in formula A2. In accordance with this embodiment, the process of the invention is conducted in the presence of at least one equivalent of a base relative to the Ruthenium complex. In another particular embodiment, each of Z and Y is other than H in formula A2. In accordance with this embodiment, the process of the invention is conducted in the presence of at least two equivalents of a base relative to the Ruthenium complex. In another particular embodiment, Z and Y are both H in formula A2. In accordance with this embodiment, no base is required for the process of the invention.

The Ruthenium complex of formula A2 is neutral.

In one embodiment of formula A2, the Ruthenium complex is represented by the structure of formula B2:

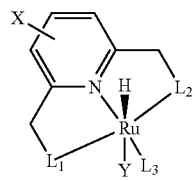

B2 wherein Y is independently H or an anionic ligand such as (but not limited to) halogen, OCOR, OCOCF$_3$, OSO$_2$R, OSO$_2$CF$_3$, CN, OH, OR, N(R)$_2$, SR or SH, and R is alkyl, cycloalkyl, aryl, alkylaryl, heterocyclyl or heteroaryl.

In another particular embodiment of formula A2, the Ruthenium complex is represented by the following structure of formula C2:

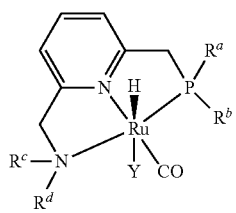

C2 wherein each of R$^a$, R$^b$, R$^c$ and R$^d$ is independently selected from the group consisting of alkyl, cycloalkyl, aryl, alkylaryl, heterocyclyl and heteroaryl.

Figure 2:
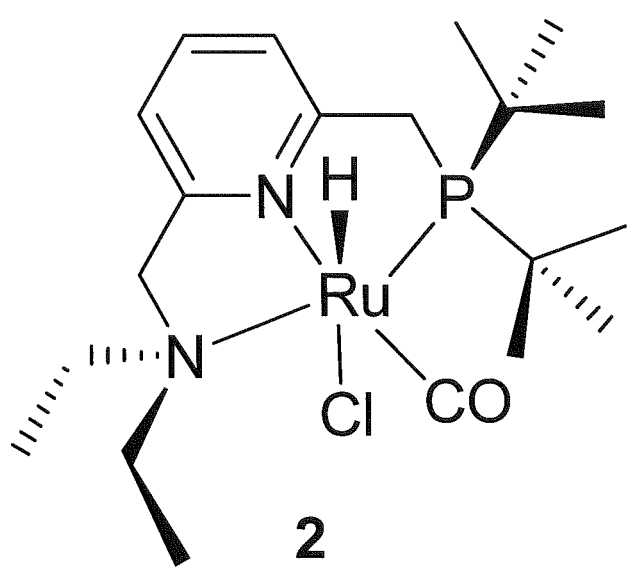
FIG. 2: shows the structure of an aromatized PNN pincer complex 2.

In one currently preferred embodiment, Y is halogen, such as chloro. A preferred complex is Ruthenium complex is represented by the structure of formula 2 (FIG. 2).

In another embodiment of the present invention, the Ruthenium complex is represented by the structure of formula A3:

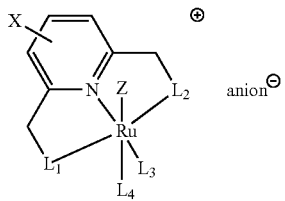

A3 wherein Z is H or an anionic ligand such as (but not limited to) halogen, OCOR, OCOCF$_3$, OSO$_2$R, OSO$_2$CF$_3$, CN, OH, OR, N(R)$_2$, SR or SH wherein R is alkyl, cycloalkyl, aryl, alkylaryl, heterocyclyl or heteroaryl; and L$_4$ is either absent or is a mono-dentate two-electron donor selected from the group consisting of CO, P(R)$_3$, P(OR)$_3$, NO$^+$, As(R)$_3$, Sb(R)$_3$, S(R)$_2$, nitrile (RCN) and isonitrile (RNC) wherein R is as defined above.

In one particular embodiment, Z is H in formula A3. In accordance with this embodiment, the process is conducted in the presence of at least one equivalent of a base relative to the Ruthenium complex. In another particular embodiment, Z is other than H in formula A3. In accordance with this embodiment, the process is conducted in the presence of at least two equivalents of a base relative to the Ruthenium complex.

Compounds of formula A2 (of which Compound 2 is a representative) and formula A3 are precursors of compounds of formula A1. Additional exemplary precursors of the complexes of formula A1 include, but are not limited to:

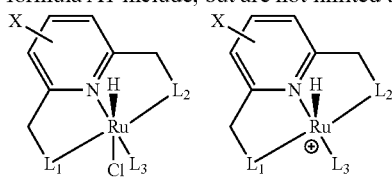

plus at least one equivalent
of base relative to Ru
(eg alkoxide, hydroxide)

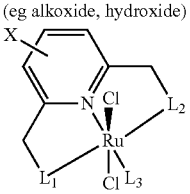

plus at least two equivalents
of base relative to Ru
(eg alkoxide, hydroxide)

It is understood that any one or more of the precursors can themselves function as complexes in the process of the present invention.

Other suitable Ruthenium complexes that can be used in the process of the invention are the complexes disclosed by Zhang et al. (20-23), the contents of each of which are incorporated by reference herein.

It is understood that when the complex includes one or more chiral centers, all stereoisomers can be utilized for the processes of the present invention.

CHEMICAL DEFINITIONS

As used herein, the term alkyl, used alone or as part of another group, refers to linear or branched saturated hydrocarbon groups. Preferred are alkyl groups containing from 1 to 12 carbon atoms (C$_1$ to C$_{12}$ alkyl), 1 to 6 carbon atoms (C$_1$ to $C_6$ alkyl), or alkyl groups containing from 1 to 4 carbon atoms ($C_1$ to $C_4$ alkyls). Examples of alkyl groups include, but are not limited to, methyl, ethyl, n-propyl, isopropyl, n-butyl, iso-butyl, sec-butyl, tert-butyl, amyl, tert-amyl, hexyl, and the like. Similarly, the term "$C_1$ to $C_{12}$ alkylene" denotes a bivalent radical of 1 to 12 carbons.

The alkyl group can be unsubstituted, or substituted with one or more substituents selected from the group consisting of halogen, hydroxy, alkoxy, aryloxy, alkylaryloxy, heteroaryloxy, oxo, cycloalkyl, phenyl, heteroaryls, heterocyclyl, naphthyl, amino, alkylamino, arylamino, heteroarylamino, dialkylamino, diarylamino, alkylarylamino, alkylheteroarylamino, arylheteroarylamino, acyl, aryloxy, nitro, carboxy, carbamoyl, carboxamide, cyano, sulfonyl, sulfonylamino, sulfinyl, sulfinylamino, thiol, alkylthio, arylthio, or alkylsulfonyl groups. Any substituents can be unsubstituted or further substituted with any one of these aforementioned substituents. By way of illustration, an "alkoxyalkyl" is an alkyl that is substituted with an alkoxy group.

The term "cycloalkyl" used herein alone or as part of another group, refers to a cyclic moiety, preferably containing 3 to 8 carbon atoms ($C_3$ to $C_8$ cycloalkyl), and can be monocyclic or polycyclic. Nonlimiting examples of cycloalkyl groups are cyclopropyl, cyclobutyl, cyclopentyl, cyclohexyl or cycloheptyl. The cycloalkyl group can be unsubstituted or substituted with any one or more of the substituents defined above for alkyl. Similarly, the term "cycloalkylene" means a bivalent cycloalkyl, as defined above, where the cycloalkyl radical is bonded at two positions connecting together two separate additional groups.

The term "aryl" used herein alone or as part of another group denotes an aromatic ring system containing from 6-14 ring carbon atoms. The aryl ring can be a monocyclic, bicyclic, tricyclic and the like. Non-limiting examples of aryl groups are phenyl, naphthyl including 1-naphthyl and 2-naphthyl, and the like. The aryl group can be unsubstituted or substituted through available carbon atoms with one or more groups defined hereinabove for alkyl. An alkylaryl group denotes an alkyl group bonded to an aryl group (e.g., benzyl).

The term "heteroaryl" used herein alone or as part of another group denotes a heteroaromatic system containing at least one heteroatom ring atom selected from nitrogen, sulfur and oxygen. The heteroaryl contains 5 or more ring atoms. The heteroaryl group can be monocyclic, bicyclic, tricyclic and the like. Also included in this expression are the benzo-heterocyclic rings. If nitrogen is a ring atom, the present invention also contemplates the N-oxides of the nitrogen containing heteroaryls. Nonlimiting examples of heteroaryls include thienyl, benzothienyl, 1-naphthothienyl, thianthrenyl, furyl, benzofuryl, pyrrolyl, imidazolyl, pyrazolyl, pyridyl, pyrazinyl, pyrimidinyl, pyridazinyl, indolyl, isoindolyl, indazolyl, purinyl, isoquinolyl, quinolyl, naphthyridinyl, quinoxalinyl, quinazolinyl, cinnolinyl, pteridinyl, carbolinyl, thiazolyl, oxazolyl, isothiazolyl, isoxazolyl and the like. The heteroaryl group can be unsubstituted or substituted through available atoms with one or more groups defined hereinabove for alkyl.

The term "heterocyclic ring" or "heterocyclyl" used herein alone or as part of another group denotes a five-membered to eight-membered rings that have 1 to 4 heteroatoms, such as oxygen, sulfur and/or nitrogen. These five-membered to eight-membered rings can be saturated, fully unsaturated or partially unsaturated. Non-limiting examples of heterocyclic rings include piperidinyl, piperidinyl, pyrrolidinyl pyrrolinyl, pyrazolinyl, pyrazolidinyl, piperidinyl, morpholinyl, thiomorpholinyl, pyranyl, thiopyranyl, piperazinyl, indolinyl, dihydrofuranyl, tetrahydrofuranyl, dihydrothiophenyl, tetrahydrothiophenyl, dihydropyranyl, tetrahydropyranyl, and the like. The heterocyclyl group can be unsubstituted or substituted through available atoms with one or more groups defined hereinabove for alkyl.

The inorganic support which is attached to the pyridine ring in formula A1, A2 or A3 can be, for example, silica, silica gel, glass, glass fibers, titania, zirconia, alumina and nickel oxide.

The polymer which is attached to the pyridine ring in formula A can be, for example, selected from polyolefins, polyamides, polyethylene terephthalate, polyvinylchloride, polyvinylidenechloride, polystyrene, polymethracrylate, natural rubber, polyisoprene, butadiene-styrene random copolymers, butadiene acrylonitrile copolymers, polycarbonate, polyacetal, polyphenylenesulfide, cyclo-olefin copolymers, styrene-acrylonitrile copolymers, ABS, styrene-maleic anhydride copolymers, chloroprene polymers, isobutylene copolymers, polystyrene, polyethylene, polypropylene, and the like.

The term "anion" as used herein refers to any moiety or group bearing a negative charge. Examples of anionic moieties include, but are not limited to halogen (e.g., F, Cl, Br, I), $OCOR$, $OCOCF_3$, $OSO_2R$, $OSO_2CF_3$, $BF_4$, $PF_6$, $SbF_6$, $B(R)_4$, $ClO_4$, $AlCl_4$, CN, OH, OR or $N(R)_2$ wherein R is selected from alkyl, cycloalkyl, aryl, alkylaryl, heterocyclyl and heteroaryl, wherein each of the alkyl, cycloalkyl, aryl, alkylaryl, heterocyclyl and heteroaryl is as defined above.

Novel Processes

The present invention provides various processes which utilize the Ruthenium complexes of formula A1, A2 or A3, as described herein.

In general, the processes of the present invention can be conducted in the absence or in the presence of a solvent. When a solvent is present, it can be an organic solvent, including but not limited to benzene, toluene, o-, m- or p-xylene mesitylene (1,3,5-trimethyl benzene), dioxane, THF, DME, anisole and cyclohexane.

The stoichiometric ratios of reagents can vary, and depend on the particular alcohol, amine, amide, etc., being used, as well as solvent used for the reaction. The reactions of the present invention can be performed for as long as needed so as to effect desired transformation, for example 1 hr to 24 hr or longer than 24 hr. The temperature range can vary from room temperature to heated conditions, for example up to 200° C. Exemplary processes of the invention are described hereinbelow.

1. Dehydrogenative Coupling of Alcohols and Amines with Liberation of $H_2$ to Form Amides In one aspect, the present invention relates to a process for preparing an amide, comprising the step of reacting a primary amine and an alcohol in the presence of a Ruthenium complex, to generate the amide and molecular hydrogen. According to the invention, primary amines are directly acylated by equimolar amounts of alcohols to produce amides and molecular hydrogen in high yields and high turnover numbers.

This reaction is catalyzed by a Ruthenium complex, which is preferably based on a dearomatized PNN-type ligand, requiring no base or acid promoters, or is based on an aromatized precursor of the dearomatized PNN-type ligand, with the optional use of one or more equivalents of a base.

A variety of alcohols can be used in the process of the present invention. In one embodiment, the alcohol is represented by the formula $R^4CH_2OH$ wherein $R^4$ is selected from the group consisting of alkyl, alkoxyalkyl, cycloalkyl, aryl, alkylaryl, heterocyclyl and heteroaryl. In several exemplary and non-limiting embodiments, the alcohol is selected from the group consisting of ethanol, propanol, butanol, pentanol, hexanol, 2-methoxyethanol, and 2-methyl-1-butanol.

A variety of amines can be used in the process of the present invention. In one embodiment, the amine is represented by the formula $R^5CH_2NH_2$ wherein $R^5$ is selected from the group consisting of alkyl, alkoxyalkyl, cycloalkyl, aryl, alkylaryl, heterocyclyl and heteroaryl In several exemplary and non-limiting embodiments, the amine is selected from the group consisting of benzylamine, 1-(2-furyl)methylamine, aniline, pentylamine, 2-methylhexylamine, and cyclohexylamine.

Use of diamines or dialcohols in the reaction leads to diamides, whereas when diamines and dialcohols are used together, the process results in a polyamide. Furthermore, reactions of amino-alcohols results in cyclic amides (lactams). For example, reaction of $H_2N(CR^1R^2)_nCH_2OH$ results in lactams for n=4, 5 or 6, such as caprolactam for n=6 and $R^1=R^2=H$. For n>6, the reaction typically results in polymers. In another embodiment, when amino alcohols such as R—CH(NH$_2$)CH$_2$OH are used, peptides or polypeptides are formed (e.g., dehydrogenation of alaninol with the Ruthenium complexes of the present invention results in polyalanine).

In another embodiment, the process of the invention can also be applied to bis-acylation reactions with diamines. Upon reacting alcohols and diamines, the corresponding bis-amides are produced in high yields. In some embodiments, the diamine is ethylenediamine, diethylenetriamine or 1,6-diaminohexane.

Similarly, when diamines and dialcohols are used, polyamides or peptides are obtained. The applicants have surprisingly discovered that Ruthenium complexes catalyze the synthesis of polyamides directly from diols and diamines. This polyamidation reaction is general, environmentally benign and atom economical. It proceeds under neutral reaction conditions without the use of activators, condensing agents or other additives. A preferable solvent for use in this reaction is 1,4-dioxane, however other solvents can be used as apparent to a person of skill in the art. Moreover, these methods produce $H_2$ as the only byproduct (Scheme 3):

Scheme 3

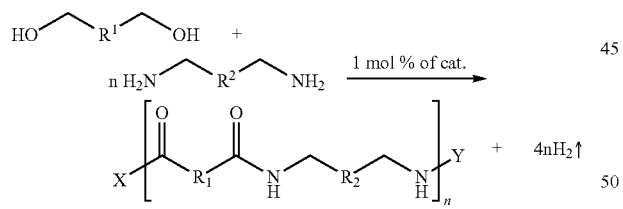

wherein $R^1$ and $R^2$ are, e.g., alkyl or aryl.

A variety of dialcohols can be used for this reaction, non-limiting examples of which include hexane-1,2-diol, octane-1,8-diol, 1,3-phenylenedimethanol, (5-methoxy-1,3-phenylene)dimethanol, 1,4-phenylenedimethanol, pyridine-2,6-diyldimethanol, pentane-1,5-diol, cyclohexane-1,4-diyldimethanol, and (5-(hexyloxy)-1,3-phenylene)dimethanol.

A variety of diamines can be used for this reaction, non-limiting examples of which include hexane-1,6-diamine, ethane-1,2-diamine, 1,3-phenylenedimethanamine, and 1,4-phenylenedimethanamine. The reaction between the amine and alcohol can be inter-molecular (i.e., the amine and the alcohol are present in separate molecules). Alternatively, the reaction between the amine and alcohol can be intra-molecular, i.e., the amine and alcohol functionalities can be present in the same molecule, resulting in intra-molecular cyclization to generate a lactam.

In some embodiments, beta-amino alcohols can be dehydrogenated in the presence of Ruthenium complexes to form cyclic dipeptides.

The aforementioned amidation and polyamidation reactions are catalyzed by the Ruthenium complexes of formula A1, A2 or A3 wherein $L_1$ is $N(R)_2$ (designated herein compounds of formulae A1', A2' or A3'):

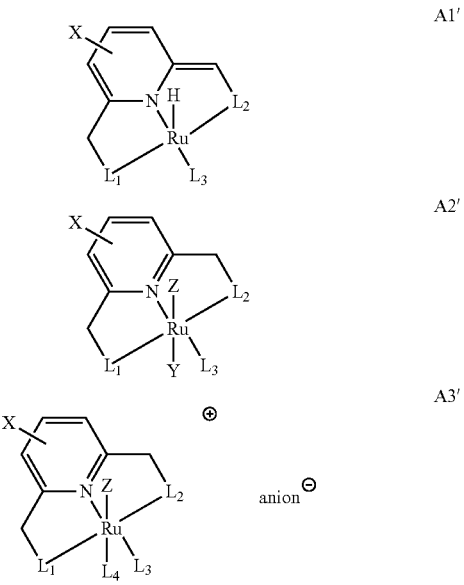

wherein $L_1$ is $N(R)_2$;

$L_2$ is selected from the group consisting of nucleophilic carbene (:CR$_2$), P(R)$_2$, P(OR)$_2$, N(R)$_2$, imine, SR, SH, S(=O)R, heteroaryl wherein the heteroatom is selected from nitrogen and sulfur, As(R)$_2$, Sb(R)$_2$ and an N-heterocyclic carbene represented by the structure:

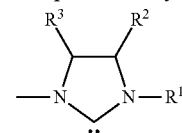

wherein each of R, $R^1$, $R^2$ and $R^3$ are independently selected from the group consisting of alkyl, cycloalkyl, aryl, alkylaryl, heterocyclyl and heteroaryl;

$L_3$ is a mono-dentate two-electron donor selected from the group consisting of CO, P(R)$_3$, P(OR)$_3$, NO$^+$, As(R)$_3$, Sb(R)$_3$, S(R)$_2$, nitrile (RCN) and isonitrile (RNC) wherein R is as defined above;

$L_4$ is absent or is $L_3$;

Y and Z are each independently H or an anionic ligand selected from the group consisting of halogen, OCOR, OCOCF$_3$, OSO$_2$R, OSO$_2$CF$_3$, CN, OH, OR, N(R$_2$), RS and SH; wherein R is as defined above;

X represents zero, one, two or three substituents selected from the group consisting of alkyl, aryl, halogen, nitro, amide, ester, cyano, alkoxy, cycloalkyl, alkylaryl, heterocyclyl, heteroaryl, an inorganic support and a polymeric moiety; and anion represents a group bearing a single negative charge One embodiment of such compounds is a pincer complex represented by the structure of formula 1 (FIG. 1).

2. Dehydrogenative Coupling of Beta-Amino Alcohols with Liberation of H$_2$ to Form Pyrazines In another embodiment, beta-amino alcohols can be dehydrogenated to form pyrazines in the presence of Ruthenium complexes. The process is illustrated in Scheme 4:

Scheme 4

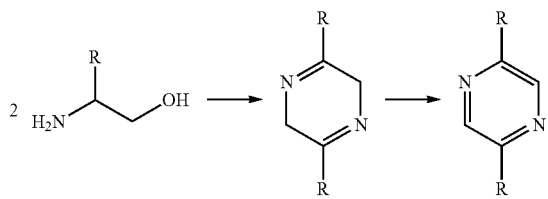

wherein R is selected from the group consisting of H, an unsubstituted or substituted alkyl, alkoxyalkyl, cycloalkyl, aryl, alkylaryl, heterocyclyl and heteroaryl.

Ruthenium complexes which catalyze the dehydrogenation of beta-amino alcohols to pyrazines are Ruthenium complexes of formula A1, A2 or A3 which contain two phosphine ligands or N-heterocyclic carbene ligands (designated herein compounds of formula A1'', A2'' and A3''):

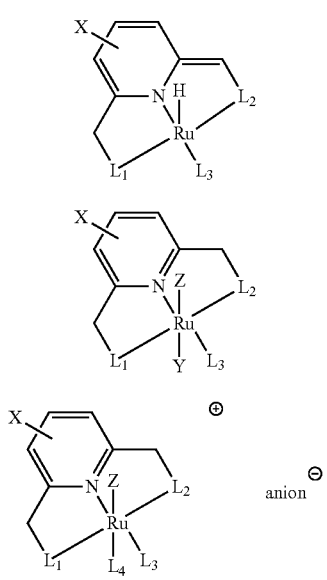

wherein

L$_1$ and L$_2$ are each independently selected from the group consisting of phosphine (P(R)$_2$), and an N-heterocyclic carbene represented by the structure:

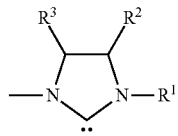

wherein each of R, R$^1$, R$^2$ and R$^3$ are independently selected from the group consisting of alkyl, cycloalkyl, aryl, alkylaryl, heterocyclyl and heteroaryl;

L$_3$ is a mono-dentate two-electron donor selected from the group consisting of CO, P(R)$_3$, P(OR)$_3$, NO$^+$, As(R)$_3$, Sb(R)$_3$, S(R)$_2$, nitrile (RCN) and isonitrile (RNC) wherein R is as defined above;

L$_4$ is absent or is L$_3$;

Y and Z are each independently H or an anionic ligand selected from the group consisting of halogen, OCOR, OCOCF$_3$, OSO$_2$R, OSO$_2$CF$_3$, CN, OH, OR, N(R)$_2$, RS and SH; wherein R is as defined above;

X represents zero, one, two or three substituents selected from the group consisting of alkyl, aryl, halogen, nitro, amide, ester, cyano, alkoxy, cycloalkyl, alkylaryl, heterocyclyl, heteroaryl, an inorganic support and a polymeric moiety; and anion represents a group bearing a single negative charge.

In one currently preferred embodiment, the Ruthenium complex is represented by the structure of formula 3 (FIG. 3).

3. Hydrogenation of Amides to Alcohols and Amines

The present invention provides a process for hydrogenating amides (including polyamides and polypeptides) by reacting the amide with molecular hydrogen (H$_2$) in the presence of the Ruthenium complexes described herein to yield the corresponding alcohol and amine. As contemplated herein, the inventors have discovered a novel process for converting amides to alcohols and amines in high yields and high turnover numbers. This reaction is catalyzed by Ruthenium complexes of formula A1', A2' and A3', wherein L$_1$ is N(R)$_2$ (as exemplified above for the reverse amidation reaction).

The process of the invention, i.e., the direct catalytic conversion of amides to alcohols and amides is illustrated in Scheme 5. This novel, environmentally benign reaction can be used to prepare alcohols and amines from any type of amide, with high atom economy and in some embodiments no stoichiometric activating agents, thus generating no waste. Thus, in one embodiment, the present invention provides a process for hydrogenating an amide represented by the formula R$^4$C(=O)—N—R$^5$R$^{5'}$ to an alcohol of formula R$^4$CH$_2$OH and amine of formula R$^5$R$^{5'}$NH:

Scheme 5

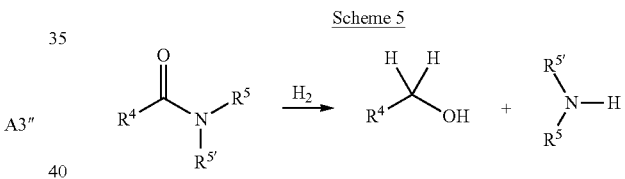

wherein R$^4$, R$^5$ and R$^{5'}$ are each independently selected from the group consisting of H, an unsubstituted or substituted alkyl, alkoxyalkyl, cycloalkyl, aryl, alkylaryl, heterocyclyl and heteroaryl.

A variety of amides can be used in the process of the invention. In some embodiments, the amide is selected from the group consisting of N-benzyl-2-methoxyacetamide, N-hexyl-2-methoxyacetamide, N-hexyl-3-methyloxetane-3-carboxamide, N-hexyl-2-furanylcarboxamide, N-benzylbenzamide, N-ethylacetamide, N-methylpropionamide, N-cyclohexyl-2-methoxyacetamide, N-phenylacetamide, N-phenylhexylamide, 2-methoxy-N-phenylacetamide, N-phenylbenzamide, Ethylenediamine-N,N'-(2-methoxyacetamide), N-hexanoylmorpholine, N-butanoylmorpholine, N-2-metoxyacetylpyrrolidine, N-formylmorpholine, N,N-dimethylformamide, N,N-diethylbenzamide, benzamide, 4-methylbenzamide, cyclohexanecarboxamide, hexanamide, acetamide, acrylamide and pivalamide. Each possibility represents a separate embodiment of the present invention.

In a similar manner, cyclic amides (lactams) can be hydrogenated to the corresponding amino alcohols. In one embodiment, the lactam is a cyclic peptide, which can be hydrogenated with the Ruthenium complex of the present invention to the respective amino alcohol. In a similar manner, polyamides can be hydrogenated to amines and alcohols, and polypeptides can be hydrogenated to amino alcohols.

4. Hydrogenation of Organic Carbonates, Carbamates and Urea Derivatives

Similar to the hydrogenation of amides, the novel Ruthenium complexes of the present invention can also catalyze the hydrogenation of organic carbonates, hydrogenation of carbamates, or hydrogenation of urea derivatives (i.e., urea substituted at one or more positions on the nitrogen atom(s))) to the corresponding amines and/or alcohols. Thus, in some embodiments, the present invention further provides a process for hydrogenating an organic carbonate, carbamate or urea derivative with molecular hydrogen ($H_2$) in the presence of the Ruthenium complex of the present invention. As contemplated herein, the inventors have discovered a novel process for converting organic carbonates, carbamates and/or urea derivatives to alcohols and/or amines in high yields and high turnover numbers. This reaction is catalyzed by Ruthenium complexes of formula A1', A2' and A3' as described above, wherein $L_1$ is $N(R)_2$, as described above with respect to processes for hydrogenation of amides to amines and alcohols and the reverse amidation/polyamidation reaction. One embodiment of such compounds is a pincer complex represented by the structure of formula 1 (FIG. 1).

In one embodiment, direct catalytic hydrogenation of organic carbonates, is illustrated in Scheme 6, whereby a carbonate represented by the formula $R^{80}$—C(=O)—$OR^{8'}$ is hydrogenated to the corresponding alcohols(s) and methanol:

Scheme 6

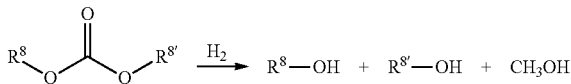

wherein $R^8$ and $R^{8'}$ are the same or different and are selected from the group consisting of an unsubstituted or substituted alkyl, alkoxyalkyl, cycloalkyl, aryl, alkylaryl, heterocyclyl and heteroaryl.

It is apparent to a person of skill in the art that when the organic carbonate is symmetric (i.e., $R^8$=$R^{8'}$) the reaction yields two equivalents of the same alcohol, and one equivalent of methanol. However, when the organic carbonate is asymmetric (i.e., $R^8$ is different from $R^{8'}$), the reaction yields a mixture of two alcohols, and methanol.

A variety of organic carbonates can be used in the process of the invention. In some embodiments, the carbonate is dimethyl carbonate, diethyl carbonate, dipropyl carbonate or dibutyl carbonate. In another embodiment, the carbonate is a polycarbonate, such as polyethylene carbonate or polypropylene carbonate. Each possibility represents a separate embodiment of the present invention.

Another embodiment of the process of the present invention, i.e., the direct catalytic hydrogenation of carbamates, is illustrated in Scheme 7, whereby a carbamate represented by the formula $R^9O$—C(=O)—$NHR^{10}$ is hydrogenated to the corresponding amine, alcohol and methanol:

Scheme 7

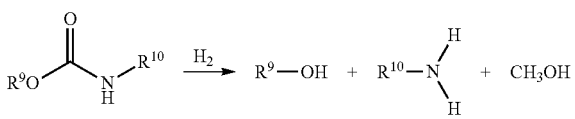

wherein $R^9$ is selected from the group consisting of an unsubstituted or substituted alkyl, alkoxyalkyl, cycloalkyl, aryl, alkylaryl, heterocyclyl and heteroaryl; and $R^{10}$ is selected from the group consisting of H or an unsubstituted or substituted alkyl, alkoxyalkyl, cycloalkyl, aryl, alkylaryl, heterocyclyl and heteroaryl.

A variety of organic carbamates can be used in the process of the invention. In some embodiments, the carbamate is methyl benzylcarbamate or methyl 4-methoxybenzylcarbamate. In another embodiment, the carbamate is a polycarbamate. Each possibility represents a separate embodiment of the present invention.

Another embodiment of the process of the present invention, i.e., the direct catalytic hydrogenation of urea derivatives, is illustrated in Scheme 8, whereby a urea derivative is hydrogenated to the corresponding amine(s) and methanol:

Scheme 8

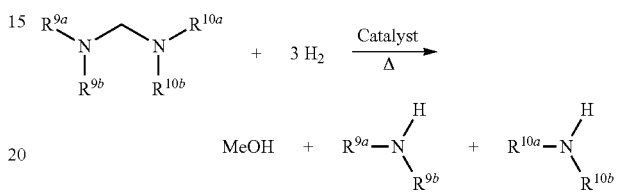

wherein each of $R^{9a}$ and $R^{10a}$, which may be the same or different, is selected from the group consisting of an unsubstituted or substituted alkyl, alkoxyalkyl, cycloalkyl, aryl, alkylaryl, and heterocyclyl, and each of $R^{9b}$ and $R^{10b}$, which may be the same or different, is selected from the group consisting of H, an unsubstituted or substituted alkyl, alkoxyalkyl, cycloalkyl, aryl, alkylaryl, and heterocyclyl. Alternatively, at least one of $R^{9a}$ and $R^{10a}$, and/or $R^{9b}$ and $R^{10b}$ together with the nitrogen to which they are attached form a heterocyclic ring.

A variety of symmetrical ($R^{9a}$=$R^{10a}$, $R^{9b}$=$R^{10b}$) and asymmetrical ($R^{9a}$≠$R10^a$, $R^{9b}$≠$R10^b$) urea derivatives can be used in the process of the invention, with each possibility representing a separate embodiment of the present invention. In some embodiments, the urea derivative is 1,3-dimethylurea, and the product of the reaction is methanol and two molecules of methylamine. In another embodiment, the urea derivative is selected from the group consisting of 1,3-dipropylurea, 1,3-dihexylurea, 1,3-bis(2-methoxyethyl)urea, 1,3-dicyclohexylurea, 1,3-dibenzylurea, 1,3-bis(4-methylbenzyl)urea, 1,3-bis(4-methylbenzyl)urea, 1,3-diphenylurea, 1,3-bis(4-(tert-butyl)phenyl)urea, 1,1,3,3-tetramethylurea, and di(piperidin-1-yl)methanone. Polyureas can also be hydrogenated in a similar manner. Each possibility represents a separate embodiment of the present invention.

5. Dehydrogenation of Secondary Alcohols:

The present invention further relates to a process for preparing a ketone by dehydrogenation of a secondary alcohol, comprising the step of reacting the secondary alcohol in the presence of the Ruthenium complex, thereby generating the ketone and molecular hydrogen. This reaction is catalyzed by Ruthenium complexes of formula A1, A2 and A3 as described above.

The process of the invention, i.e., the direct catalytic conversion of secondary alcohols into ketones and dihydrogen is illustrated in Scheme 9A. In accordance with this process, a secondary alcohol represented by formula $R^{14}CH(OH)R^{14'}$ is converted to a ketone represented by the structure $R^{14}$—C(=O)—$R^{14'}$:

Scheme 9A

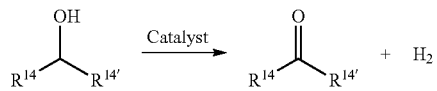

A variety of alcohols can be used in the process of the invention. In some embodiments, the alcohol is selected from the group consisting of 1-phenyl-1-ethanol, 2-hexanol, cyclohexanol and 2-propanol. Each possibility represents a separate embodiment of the present invention.

6. Synthesis of Amides from Esters and Alcohols

The present invention further provides a process for preparing amides, by reacting an amine and an ester in the presence of a Ruthenium complex, to generate the amide and molecular hydrogen ($H_2$). As contemplated herein, the inventors have further discovered a novel process for preparing amides in which primary and secondary amines are directly reacted with esters to produce amides and molecular hydrogen in high yields and high turnover numbers. This reaction is catalyzed by Ruthenium complexes of formula A1', A2' and A3' as described above, wherein $L_1$ is $N(R)_2$. One embodiment of such compounds is a pincer complex represented by the structure of formula 1 (FIG. 1). Depending on the complex being used, the reaction permits the optional use of one or more equivalents of a base. Reactions of esters with diamines leads to diamides.

The process of the invention, i.e., the direct catalytic reaction of esters and amines into amides and dihydrogen is illustrated in Scheme 9B. In accordance with this process, an amine represented by formula $R^{15}R^{15'}NH$ is reacted with an ester represented by the formula $R^{16}$—C(=O)—$OCH_2R^{16'}$ to generate an amide represented by the structure $R^{16}$—C(=O)—$NR^{15}R^{15'}$. This novel, environmentally benign reaction can be used to produce various amides from very simple substrates, with high atom economy and in some embodiments no stoichiometric activating agents, thus generating no waste.

Scheme 9B

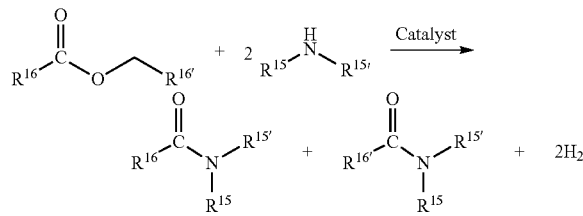

wherein $R^{15}$, $R^{15'}$, $R^{16}$ and $R^{16'}$ are each independently selected from the group consisting of H, an unsubstituted or substituted alkyl, alkoxyalkyl, cycloalkyl, aryl, alkylaryl, heterocyclyl and heteroaryl, wherein $R^{15}$, $R^{15'}$ and $R^{16}$ can be the same or different from each other.

A variety of esters can be used in the process of the invention. In some embodiments, the ester is selected from the group consisting of ethyl acetate, butyl butyrate, pentyl pentanoate and hexyl hexanoate. Each possibility represents a separate embodiment of the present invention.

A variety of primary and secondary amines (as well as ammonia) may be used in the process of the invention. In some embodiments, the amine is selected from the group consisting of pyrrolidine, morpholine, 1-methyl piperazine, piperidine, piperazine, 1-hexylamine and p-tolylmethanamine.

In another embodiment, the process of the invention can also be applied to bis-acylation reactions with diamines. Upon reacting alcohols and diamines, the corresponding bis-amides are produced in high yields.

7. Acylation of Alcohols Using Esters with Liberation of $H_2$

The present invention further provides a process for preparing esters by acylation of alcohols using esters in the presence of a Ruthenium complex, to generate the ester compound and molecular hydrogen. In one embodiment, the process involves reaction of primary alcohols and esters. In another embodiment, the process involves reaction of a secondary alcohols and esters. This reaction is catalyzed by Ruthenium complexes of formula A1, A2 and A3 as described above. One embodiment of such compounds is a pincer complex represented by the structure of formula 1 (FIG. 1). Depending on the complex being used, the reaction permits the optional use of one or more equivalents of a base.

In one embodiment, the process of the invention, i.e., the direct catalytic acylation of alcohols using esters to yield an ester and dihydrogen is illustrated in Scheme 10. In accordance with this process, two equivalents of a primary or secondary alcohol represented by formula $R^{17}R^{17'}CHOH$ reacts with one equivalent an ester by the structure $R^{18}$—C(=O)—$OCH_2R^{18'}$ as shown in Scheme 10. This novel, environmentally benign reaction, can be used to produce various esters from very simple substrates, with high atom economy and in some embodiments no stoichiometric activating agents, thus generating no waste.

Scheme 10

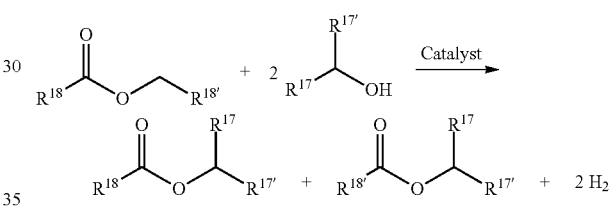

wherein $R^{17}$, $R^{17'}$, $R^{18}$ and $R^{18'}$ are each independently selected from the group consisting of H, an unsubstituted or substituted alkyl, alkoxyalkyl, cycloalkyl, aryl, alkylaryl, heterocyclyl and heteroaryl.

A variety of alcohols can be used in the process of the invention. In some embodiments, the alcohol is selected from the group consisting of cyclohexanol, cyclopentanol, 1-phenylethanol, isopropanol and 3-pentanol. Each possibility represents a separate embodiment of the present invention.

A variety of esters can be used as the starting materials. In some embodiments, the ester is selected from the group consisting of ethyl acetate, hexyl hexanoate, pentyl pentanoate, butyl butyrate, ethyl butyrate and methyl hexanoate.

8. Coupling of Alcohols with Water to Form Carboxylic Acid with Liberation of $H_2$ The present invention further provides a process for preparing carboxylic acids by contacting primary alcohols with water in the presence of a Ruthenium complex and a base, to generate the carboxylic acid salt and molecular hydrogen and, if desired, followed by conversion of the carboxylic acid salt to the corresponding carboxylic acid. These reactions are catalyzed by Ruthenium complexes of formula A1, A2 and A3, as described hereinabove. Preferred complexes for this reaction are Pincer complexes represented by the structure of Formula 1.

In one embodiment, the process of the invention, i.e., the direct catalytic conversion of primary alcohols to carboxylic acids and dihydrogen is illustrated in Scheme 11. In accordance with this process, a primary alcohol represented by formula $R^{17}CH_2OH$ is contacted with water and a base (e.g., NaOH) as shown in Scheme 11. This novel, environmentally benign reaction, can be used to produce various carboxylic acids and their salts from very simple substrates, with high atom economy and in some embodiments no stoichiometric activating agents, thus generating no waste. If desired, the salt is neutralized with the appropriate acid to provide the corresponding carboxylic acid.

Scheme 11

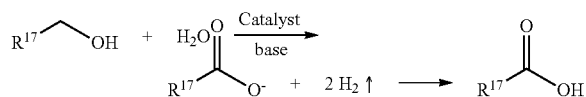

wherein $R^{17}$ is selected from the group consisting of H, an unsubstituted or substituted alkyl, alkoxyalkyl, cycloalkyl, aryl, alkylaryl, heterocyclyl and heteroaryl.

A variety of bases can be used for this reaction, non-limiting examples of which include an inorganic or organic base selected from sodium carbonate, potassium carbonate, sodium hydroxide, potassium hydroxide, sodium ethoxide, potassium tert-butoxide, sodium methoxide. The acid used to neutralize the salt can be, e.g. a mineral acid such as hydrochloric acid, hydrobromic acid, and the like. Each possibility represents a separate embodiment of the invention.

A variety of alcohols can be used in the process of the invention. In some embodiments, the alcohol is selected from the group consisting of butanol, pentanol, decanol, 2-methoxyethanol, 2-phenylethanol, cyclohexylmethanol, 3-phenylbutan-1-ol, but-3-en-1-ol, (4-methoxyphenyl)methanol, and (2,4-dimethoxyphenyl)methanol. Each possibility represents a separate embodiment of the present invention.

The disclosures of all cited references are incorporated by reference as if fully set forth herein.

The principles of the present invention are demonstrated by means of the following non-limiting processes.

Exemplary Processes:

A. Catalysis with Ruthenium Complex 1:

When a toluene solution of Ruthenium complex 1 (0.2 mol %) with 1:1 benzylamine and 1-hexanol was refluxed in a closed system for 6 h, 63% conversion of 1-hexanol to N-benzyl hexanamide was observed. Continuing the reaction up to 40 h resulted in a mixture of products. In order to facilitate formation of the product amide by hydrogen removal, 1-hexanol and benzyl amine were heated with 1 (0.1 mol %) under a flow of argon in refluxing toluene for 7 h. This setup resulted in the formation of N-benzyl hexanamide in 96% yield and a trace of N-benzyl-hexyl-1-amine (1%). Interestingly, no formation of hexyl hexanoate, which forms quantitatively in the absence of amine, was observed (Table 1, entry 1). Repeating the reaction with 1-pentanol under identical conditions led to selective direct amidation, providing N-benzyl pentanamide in 97% yield (Table 1, entry 2). 2-Methoxyethanol underwent clean dehydrogenative acylation by reaction with the primary amines benzylamine, pentylamine, and cyclohexylamine to give methoxy acetylated amides in almost quantitative yields (entries 3, 8, and 10).

TABLE 1

Direct dehydrogenative acylation of amines with alcohols catalyzed by the ruthenium complex 1. Complex 1 (0.01 mmol), alcohol (10 mmol), amine (10 mmol), and toluene (3 mL) were refluxed under Argon flow (29). Conversion of alcohols was 100% (by GC analysis).

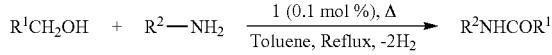

| Entry | $R^1CH_2OH$ | $R^2NH_2$ | Time (h) | Amides | Yield* (%) |
|---|---|---|---|---|---|
| 1 | pentyl-CH$_2$OH | PhCH$_2$NH$_2$ | 7 | PhCH$_2$NHC(O)-pentyl | 96 |
| 2 | butyl-CH$_2$OH | PhCH$_2$NH$_2$ | 7 | PhCH$_2$NHC(O)-butyl | 97 |
| 3 | MeOCH$_2$CH$_2$OH | PhCH$_2$NH$_2$ | 9 | PhCH$_2$NHC(O)CH$_2$OMe | 99 |

TABLE 1-continued

Direct dehydrogenative acylation of amines with alcohols catalyzed by the ruthenium complex 1. Complex 1 (0.01 mmol), alcohol (10 mmol), amine (10 mmol), and toluene (3 mL) were refluxed under Argon flow (29). Conversion of alcohols was 100% (by GC analysis).

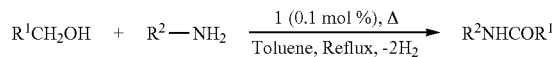

$R^1CH_2OH + R^2-NH_2 \xrightarrow[\text{Toluene, Reflux, -2H}_2]{1\ (0.1\ \text{mol \%}),\ \Delta} R^2NHCOR^1$

| Entry | $R^1CH_2OH$ | $R^2NH_2$ | Time (h) | Amides | Yield* (%) |
|---|---|---|---|---|---|
| 4 | (isobutanol) | PhCH₂NH₂ | 12 | PhCH₂NHC(O)CH(CH₃)CH₂CH₃ | 70† |
| 5 | n-hexanol | furfurylamine | 8 | furfuryl hexanamide | 78† |
| 6 | n-hexanol | Ph₂CH₂NHCH₂Ph (dibenzylamine) | 8 | N,N-dibenzyl hexanamide | 0† |
| 7 | n-pentanol | aniline | 8 | N-phenyl pentanamide | 58† |
| 8 | methoxyethanol | n-pentylamine | 8 | N-pentyl methoxyacetamide | 99 |
| 9 | n-hexanol | 2-hexylamine | 8 | N-(hex-2-yl) hexanamide | 72† |
| 10 | methoxyethanol | cyclohexylamine | 8 | N-cyclohexyl methoxyacetamide | 99 |

*Isolated yields.
†The remaining alcohol was converted into the corresponding ester. In the reactions involving hexanol and pentanol, trace amount of the corresponding secondary amines were detected (GC-MS).

It has further been discovered that the amidation reactions are sensitive to steric hindrance at the α positions of either the alcohol or the amine. Thus, when 2-methyl-1-butanol reacted with benzyl amine, the corresponding amide was obtained in 70% yield, the rest of the alcohol being converted to the ester 2-methylbutyl 2-methylbutanoate (Table 1, entry 4). A similar pattern was also observed when 2-methyl hexamine reacted with hexanol, leading to 72% yield of the corresponding amide (Table 1, entry 9). 1-(2-furyl)methylamine provided 78% yield of amide when reacted with 1-hexanol (Table 1, entry 5). When aniline was subjected to acylation with 1-pentanol, the amide was obtained in 58% yield (Table 1, entry 5). The lower reactivity of aniline may be attributed to its lower nucleophilicity as compared with alkylamines. Secondary amines do not react. Thus, heating dibenzyl amine with 1-hexanol under the experimental conditions resulted in a quantitative yield of hexyl hexanoate (Table 1, entry 6).

The inventors also examined bis-acylation processes with diamines. Upon refluxing a slight excess of a primary alcohol and complex 1 with diamines (500 equiv relative to 1) in toluene under argon, bis-amides were produced in high yields. Thus, reaction of 2-methoxyethanol with ethylene diamine, and 1-hexanol with 1,6-hexamethylene diamine resulted in quantitative yields of the corresponding bis-amides (Table 2, entries 1,3). The high selectivity of the dehydrogenative amidation reaction to primary amine functionalities enabled the direct bis-acylation of diethylenetriamine with 1-hexanol to provide the bis-amide in 88% yield without the need to protect the secondary amine functionality (Table 2, entry 2).

(1.25 mmol) and benzyl amine (2.5 mmol) under argon for 8 h, either in the presence or absence of complex 1, resulted in no N-benzylhexanamide. Thus, it is contemplated that the reaction proceeds via the hemiaminal pathway.

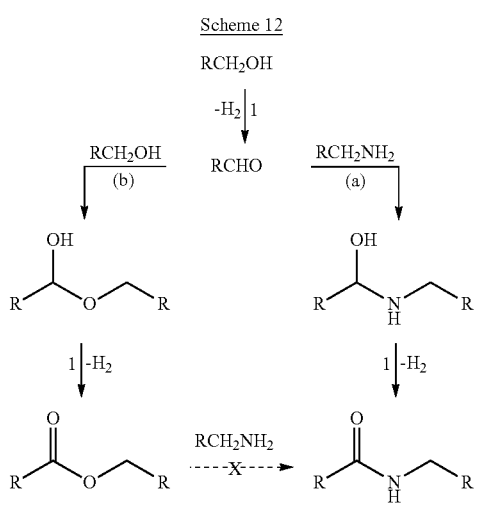

Scheme 12

On the basis of the above results and the known chemistry of PNN-type pincer complexes (31), the mechanism depicted in Scheme 13 is tentatively proposed. Following a catalytic

TABLE 2

Bis-acylation of diamines with alcohols catalyzed by 1. Complex 1(0.01 mmol), alcohol (10.5 mmol), diamine (5 mmol), and toluene (5 mL) were refluxed under Ar flow (23).

| Entry | Diamine | Time (h) | Bis-amide | Yield (%) |
|---|---|---|---|---|
| 1 | Ethylenediamine | 9 | (structure) | 99 |
| 2 | Diethylenetriamine | 8 | (structure) | 88 |
| 3 | 1,6-Diaminohexane | 9 | (structure) | 95 |

Though not wishing to be bound by any particular mechanism or theory, it is contemplated that the direct acylation of alcohols to amides with $H_2$ liberation may in principle proceed in two ways as shown in Scheme 12: (a) dehydrogenation of the alcohol to the aldehyde followed by its reaction with a primary amine to form a hemiaminal that is subsequently dehydrogenated to the amide; or (b) formation of a hemiacetal from the aldehyde and alcohol, followed by its dehydrogenation to the ester (20) which reacts with the amine to form the amide (30). The latter possibility is less likely to occur because refluxing a toluene solution of hexyl hexanoate cycle for dehydrogenation of the alcohol to the corresponding aldehyde, reaction with the amine can form the hemiaminal B, which upon reaction with 1 can lead to the aromatic intermediate C. β-H elimination from C can form the observed product amide and generate the known (20,24) trans Ru dihydride complex 2. Elimination of dihydrogen from 2 (20,24) would regenerate complex 1, completing the catalytic cycle. Interestingly, the dehydrogenation of the hemiaminal B to the amide prevails relative to the expected facile water elimination to give an imine, which on hydrogenation would provide the secondary amine (32-34), observed only in trace amounts.

Scheme 13

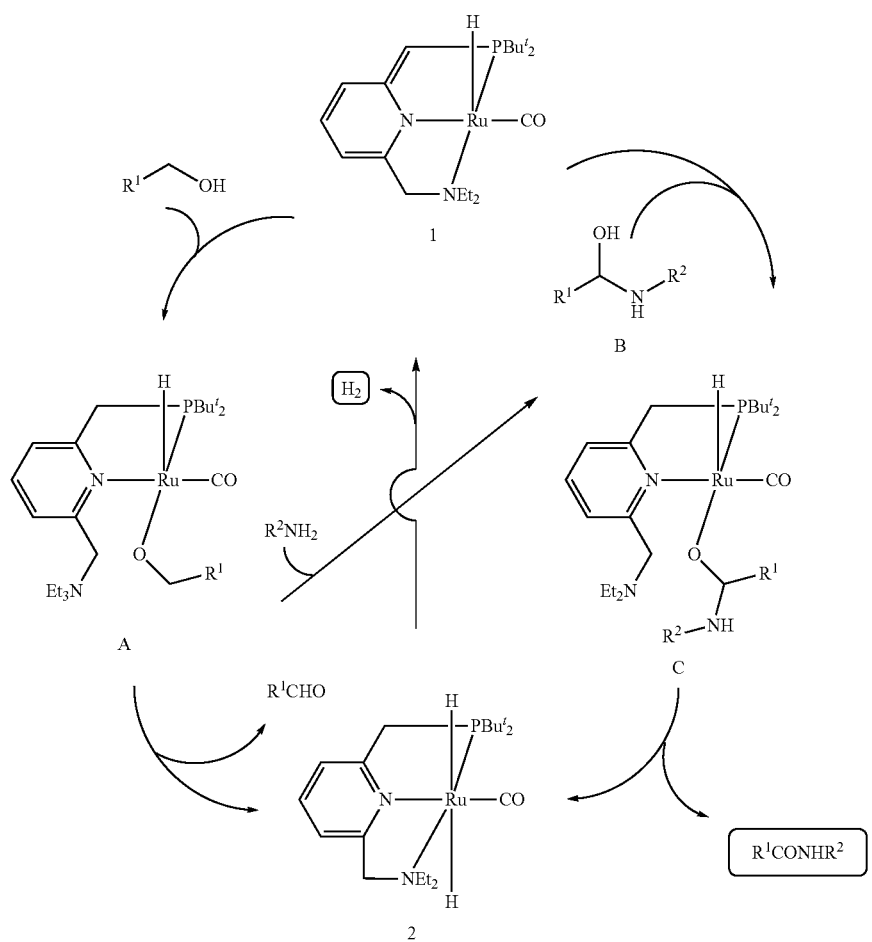

It is apparent to a person of skill in the art that the mechanism by which the reaction takes imposes no limitations on the scope of the invention.

B. Catalysis with Ruthenium Complex 2:

Scheme 14

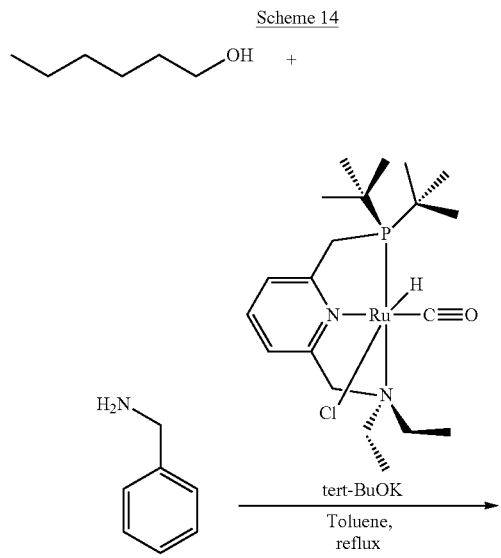

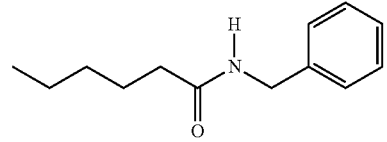

Complex RuH(Cl)(CO)(PNN) (PNN=[2-(di-tert-butylphosphinomethyl)-6-diethylaminomethyl)pyridine] (0.01 mmol), 1-hexanol (1.02 g, 10 mmol), Benzyl amine (1.07 g, 10 mmol) and toluene (3 mL) were taken in a Schlenk flask under an atmosphere of nitrogen. To the above mixture was added the base potassium-$^t$butoxide (1.1 mg, 0.01 mmol). The reaction mixture was pale yellow in color. Then, the flask was equipped with a condenser and the solution was refluxed with stirring under argon for 12 hrs. The color of the reaction mixture became brown. After cooling to room temperature, the consumption of starting materials was checked by GC using a Carboxen 1000 column on a HP 690 series GC system (100% conversion of alcohol was observed). Then, the solvent was evaporated in vacuum to obtain a white solid. The solid obtained was washed with hexane and dried in vacuum for 2-3 hrs.

Wt of the product N-benzylhexanoamide: 1.94 g Yield: 93.7%

MP: 55° C.

These results highlight the substantial scope for the preparation of the fundamental amide motif by direct acylation of amines with alcohols, a clear departure from the conventional synthetic procedures.

The disclosures of all cited references are incorporated by reference as if fully set forth herein.

Experimental Details Section

General Experimental

All experiments with metal complexes and phosphine ligands were carried out under an atmosphere of purified nitrogen in a Vacuum Atmospheres glove box equipped with a MO 40-2 inert gas purifier or using standard Schlenk techniques. All solvents were reagent grade or better. All non-deuterated solvents were refluxed over sodium/benzophenone ketyl and distilled under argon atmosphere. Deuterated solvents were used as received. All solvents were degassed with argon and kept in the glove box over 4 Å molecular sieves. The ligand PNN (2-(di-tert-butylphosphinomethyl)-6-diethylaminomethyl)pyridine) and the complex 1 were prepared by reported methods (20). RuHCl(CO)(PPh$_3$)$_3$ was prepared according to a literature procedure (35). Satisfactory spectral and physical data were obtained for all amides.

Melting points are uncorrected. Thin layer chromatography (TLC) was performed on Merck 1.05554 aluminum sheets precoated with silica gel 60 F$_{254}$ and the spots visualized with UV light at 254 nm or under iodine. Column chromatography purifications were performed by flash chromatography using Merck silica gel 60 (0.063-0.200 mm). $^1$H, $^{13}$C and $^{31}$P NMR spectra were recorded at 500, 100, and 162 MHz, respectively, using a Bruker AMX-500 NMR spectrometer. $^1$H and $^{13}$C{$^1$H} NMR chemical shifts are reported in ppm downfield from tetramethylsilane. $^{31}$P NMR chemical shifts are reported in parts per million downfield from H$_3$PO$_4$ and referenced to an external 85% solution of phosphoric acid in D$_2$O. Abbreviations used in the NMR follow-up experiments: b, broad; s, singlet; d, doublet; t, triplet; q, quartet; m, multiplet. IR spectra were recorded on a Nicolet FT-IR spectrophotometer. Mass spectra were recorded on Micromass Platform LCZ 4000, using Electro Spray Ionization (ESI) mode.

Example 1

Representative Procedure for Catalytic Dehydrogenative Mono-Acylation of Primary Amines and Alcohols This example provides a typical procedure for the catalytic dehydrogenative mono-acylation of primary amines with alcohols (Table 1): Complex RuH(CO)(PNN*) 1 (0.01 mmol), an alcohol (10 mmol), an amine (10 mmol) and toluene (3 mL) were taken in a Schlenk flask under an atmosphere of purified nitrogen in a Vacuum Atmospheres glove box. The flask was equipped with a condenser and the solution was refluxed with stirring in an open system under argon for the specified time (Table 1). After cooling to room temperature, the consumption of starting materials was checked by GC using a Carboxen 1000 column on a HP 690 series GC system.
Purification of Amides in Entries 1-3, and 10:

After completion of reaction, the reaction mixture was cooled and allowed to stand at room temperature, during which the product amides crystallized from the solution. The solution was decanted and the solids were washed with a mixture of hexane/toluene (1:1). The amides were dried under vacuum for overnight.
Purification of Amides in Entries 4-5 and 7-9:

After completion of the reaction, the solvent was removed under vacuum and the resulting residue was purified by the column chromatography on silica gel using EtOAc/n-hexane.
Entry 6:

After completion of reaction, the reaction mixture was cooled to room temperature and dibenzyl amine and hexyl hexanoate were determined by GC with mesitylene as an internal standard, using a Carboxen 1000 column on a HP 690 series GC system.

N-(2-furylmethyl)hexanoamide (entry 5)

Colorless solid. mp 54-55° C. IR (KBr): 3296, 3065, 2953, 2930, 2871, 2870, 1634, 1545, 1456, 1426, 1383, 1150, 1079, 911, 728 cm$^{-1}$. $^1$H NMR (CDCl$_3$): 0.88 (t, $^3J_{H,H}$=7.0 Hz, 3H, CH$_3$), 1.24-1.35 (m, 4H, 2×CH$_2$), 1.63 (m, 2H, CH$_2$), 2.19 (t, $^3J_{H,H}$=7.9 Hz, 2H, COCH$_2$), 4.42 (d, $^3J_{H,H}$=5.3 Hz, 2H, NCH$_2$), 5.94 (bs, 1H, NH), 6.21 (d, $^3J_{H,H}$=2.5 Hz, 1H, CH), 6.31 (overlapping dd, $^3J_{H,H}$=3.0, 1.5 Hz, 1H, CH), 7.34 (s, 1H, OCH). $^{13}$C{$^1$H}NMR (CDCl$_3$): 13.87 (CH$_3$), 22.33 (CH$_2$), 25.28 (CH$_2$), 31.37 (CH$_2$), 36.35 (CH$_2$), 36.52 (CH$_2$), 107.25 (CH), 110.37 (CH), 142.04 (OCH), 151.44 (OCCH$_2$), 172.89 (NCO). Assignment of signals was confirmed by DEPT-135 NMR studies. MS (ESI) 218.24 (100%, (M+Na)$^+$). Anal. Calcd for C$_{11}$H$_{17}$NO$_2$: C, 67.66; H, 8.78; N, 7.17. Found: C, 67.92; H, 8.69; N, 7.24.

2-Methoxy-N-pentylacetamide (entry 8)

Colorless oil. IR (neat): 3311, 2936, 1660, 1540.4, 1472.3 cm$^{-1}$. $^1$H NMR (CDCl$_3$): 0.90 (t, $^3J_{H,H}$=7.0 Hz, 3H, CH$_3$), 1.30-1.35 (m, 4H, 2×CH$_2$), 1.53 (quintet, $^3J_{H,H}$=7.0 Hz, 2H, CH$_2$), 3.28 (dt, $^3J_{H,H}$=7.0 Hz, 2H, NCH$_2$), 3.42 (s, 3H, OCH$_3$), 3.88 (s, 2H, OCH$_2$), 6.62 (bs, 1H, NH). $^{13}$C{$^1$H}NMR (CDCl$_3$): 13.68 (CH$_3$), 22.06 (CH$_2$), 28.77 (CH$_2$), 29.01 (CH$_2$), 38.49 (CH$_2$), 58.85 (OCH$_3$), 71.74 (CH$_2$), 169.08 (NCO). Assignment of signals was confirmed by DEPT-135 NMR studies. MS (ESI) 182.22 (100%, (M+Na)$^+$). HRMS calcd for C$_8$H$_{16}$NO$_2$: 158.1181. found 158.1176. Anal. Calcd for C$_8$H$_{17}$NO$_2$: C, 60.35; H, 10.76; N, 8.80. Found: C, 60.21; H, 10.83; N, 8.75.

N-(1-methylhexyl)hexanoamide (entry 9)

Colorless oil. IR (neat): 3294, 2970, 2936, 2851, 1652, 1549, 1455 cm$^{-1}$. $^1$H NMR (CDCl$_3$): 0.84 (overlapping t, $^3J_{H,H}$=6.7 Hz, 6H, 2×CH$_3$), 1.08 (d, $^3J_{H,H}$=6.7 Hz, 3H, CH$_3$), 1.21-1.33 (m, 10H, 5×CH$_2$), 1.36-1.41 (m, 2H, CH$_2$), 1.60 (quintet, $^3J_{H,H}$=7.5 Hz, 2H, CH$_2$), 2.12 (t, $^3J_{H,H}$=7.5 Hz, 2H, CH$_2$), 3.93 (m, 1H), 5.83 (bs, 1H, NH). $^{13}$C{$^1$H}NMR (CDCl$_3$): 13.64 (CH$_3$), 13.7 (CH$_3$), 20.66 (CH$_3$), 22.18 (CH$_2$), 22.31 (CH$_2$), 25.43 (CH$_2$), 25.56 (CH$_2$), 31.24 (CH$_2$), 31.47 (CH$_2$), 36.57 (CH$_2$), 44.68 (CH), 172.29 (NCO). Assignment of signals was confirmed by DEPT-135 NMR studies. MS (ESI) 236.62 (100%, (M+Na)$^+$), 214.6 (13%, (M+1)$^+$). Anal. Calcd for C$_{13}$H$_{27}$NO: C, 73.18; H, 12.76; N, 6.56. Found: C, 72.89; H, 12.83; N, 6.53.

Typical Procedure for the Catalytic Dehydrogenative Bis-Acylation of Diamines with Alcohols (Table 2)

Complex 1 (0.01 mmol), an alcohol (10.5 mmol), an diamine (5 mmol), and toluene (5 mL) were placed in a Schlenk flask under an atmosphere of purified nitrogen in a Vacuum Atmospheres glove box. The flask was equipped with a condenser and the solution was refluxed with stirring in an open system under argon flow for the specified time (Table 2). The reaction mixture was cooled to room temperature and the consumption of starting materials was checked by GC using a Carboxen 1000 column on a HP 690 series GC system. The reaction mixture was allowed to stand at room temperature and the bis-amides crystallized from the solution. The liquid was removed by decantation and the solids were washed with a mixture of dichoromethane/toluene (2:8). The resulting bis-amides were dried under vacuum overnight.

N,N'-ethane-1,2-diylbis(2-methoxyacetamide)(36) (entry 1)

Colorless solid, mp 142-143° C. IR (CH$_2$Cl$_2$): 3294, 3063, 2987, 2460, 1685, 1429, 1285, 1131 cm$^{-1}$. $^1$H NMR (CDCl$_3$): 3.43 (s, 6H, OCH$_3$), 3.48 (s, 4H, 2×NCH$_2$), 3.91 (s, 4H, 2×OCH$_2$), 6.96 (bs, 2H, NH). $^{13}$C{$^1$H}NMR (CD$_3$OD): 39.59 (NCH$_2$), 59.55 (OCH$_3$), 72.59 (OCH$_2$), 172.99 (quat-C, NCO). Assignment of signals was confirmed by DEPT-135 NMR studies. MS (ESI) 227.58 (100%, (M+Na)$^+$). Anal. Calcd for C$_8$H$_{16}$N$_2$O$_4$: C, 47.05; H, 7.90; N, 13.72. Found: C, 47.23; H, 7.97; N, 13.62.

N,N'-(iminodiethane-2,1-diyl)dipentanoamide (entry 2)

Colorless solid, mp 85-87° C. IR (neat): 3251, 3089, 2970, 2927, 2876, 1651, 1566, 1480, 1268, 1140 cm$^{-1}$. $^1$H NMR (CDCl$_3$): 0.92 (t, $^3J_{H,H}$=7.0 Hz, 6H, 2×CH$_3$), 1.36 (m, $^3J_{H,H}$=7.5, 7.0 Hz, 4H, 2×CH$_3$CH$_2$CH$_2$), 1.62 (overlapping two t, $^3J_{H,H}$=8.0, 7.5 Hz, 4H, 2×CH$_2$), 1.71 (s, 1H, NH), 2.20 (t, $^3J_{H,H}$=7.5 Hz, 4H, CH$_2$), 2.77 (t, $^3J_{H,H}$=6.0 Hz, 4H, CH$_2$), 3.35 (overlapping dt, $^3J_{H,H}$=6.0, 5.5 Hz, 4H), 5.99 (bs, 2H, CONH). $^{13}$C{$^1$H}NMR (CD$_3$OD): 14.15 (CH$_3$), 23.40 (CH$_2$), 29.10 (CH$_2$), 36.87 (CH$_2$), 39.84 (CH$_2$), 49.37 (CH$_2$), 176.51 (NCO). Assignment of signals was confirmed by DEPT-135 NMR studies. MS (ESI) 294.66 (100%, (M+Na)$^+$), 272.62 (43%, (M+1)$^+$). HRMS Calcd for C$_{14}$H$_{28}$N$_3$O$_2$: 270.2182. found 270.2177.

N,N'-hexane-1,6-diyldihexanoamide (37) (entry 3)

Colorless solid. mp 140-142° C. IR (neat): 3311, 3063, 2945, 2868, 1642, 1549, 1481, 1438, 1379, 1226 cm$^{-1}$. $^1$H NMR (CDCl$_3$): 0.90 (t, $^3J_{H,H}$=7.0 Hz, 6H, 2×CH$_3$), 1.29-1.36 (m, 12H, 6×CH$_2$), 1.50 (m, 4H, 2×CH$_2$), 1.64 (quintet, $^3J_{H,H}$=7.0 Hz, 4H, 2×CH$_2$), 2.17 (t, $^3J_{H,H}$=7.5 Hz, 4H, 2×CH$_2$), 3.25 (overlapping 2 triplets, $^3J_{H,H}$=7.0 Hz, 4H, 2×CH$_2$), 5.6 (bs, 2H, NH). $^{13}$C{$^1$H}NMR (CD$_3$OD): 14.32 (CH$_3$), 23.44 (CH$_2$), 26.82 (CH$_2$), 27.59 (CH$_2$), 30.35 (CH$_2$), 32.52 (CH$_2$), 37.11 (CH$_2$), 40.19 (CH$_2$), 176.19 (NCO). Assignment of signals was confirmed by DEPT-135 NMR studies. MS (ESI) 648.44 (38%, (2M+Na)$^+$), 335.87 (100%, (M+Na)$^+$). Anal. Calcd for C$_{18}$H$_{36}$N$_2$O$_2$: C, 69.18; H, 11.61; N, 8.96. Found: C, 69.39; H, 11.56; N, 8.91

Example 2

Hydrogenation of Amides to the Corresponding Alcohols and Amines

Scheme 15

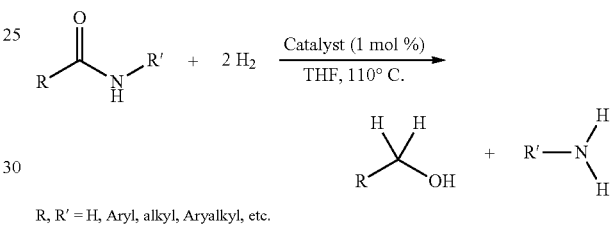

R, R' = H, Aryl, alkyl, Aryalkyl, etc.

Complex 1 was tested as a catalyst for the hydrogenation of amides. Thus, upon treatment of N-benzyl-2-methoxyacetamide with dihydrogen (10 atm) at 110° C. (bath temperature) in dry THF for 48 h with a catalytic amount of 1 (1 mol %), 62.7% of 2-methoxyethanol and 62.0% of benzyl amine were obtained. Performing the reaction at 140° C. using 1,4-dioxane as solvent did not significantly improve the yield (alcohol yield 66.3%). It was significant that the reaction was selective and the corresponding secondary amine was not observed. Results of some typical processes are shown in Table 3.

TABLE 3

Selective Hydrogenation of Amides to Alcohols and Amines Using H$_2$ catalyzed by pincer complex 1

Reaction condition[a]

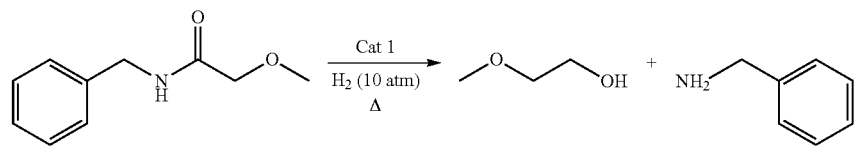

| | Yield (%)[b] | |
| Entry | Alcohol | Amine |
| --- | --- | --- |
| 1 | 62.7 | 62.0 |
| 2 | 66.3 | 66.8[c] |

[a]Complex 1 (0.01 mol), amide (1 mmol), H$_2$ (10 atm), and dry THF (2 ml) were heated in a Fischer-Porter tube at 110° C. (bath temperature) for 48 h.
[b]Yields of products were analyzed by GC (m-xylene as internal standard).
[c]1,4-dioxane (2 mL) at 140° C. after 48 h.

Thus, amides can be selectively hydrogenated to alcohols and amines for the first time. The reaction proceeds under mild pressure, neutral, homogeneous conditions using Ruthenium complexes as catalysts according to the invention and dihydrogen by metal-ligand cooperation. This new catalytic protocol exhibits a broad substrate scope providing a variety of amines and alcohols in good to excellent yield.

Example 3

Hydrogenation of Cyclic Di-Peptides

The process of the present invention can also be used for catalytic hydrogenation of di-peptides. For example, cyclic di-peptides can be hydrogenated to amino alcohols. In a general procedure, a 100 mL Fischer-Porter tube was charged with the catalyst 1 (0.02 mmol), the cyclic di-peptides (1.0 mmol) and THF (2 mL) under an atmosphere of purified nitrogen in a Vacuum Atmospheres glove box. The pressure tube was taken out of the glove box, and subjected to three successive cycles of pressurization/venting with $H_2$ (3 atm), then pressurized with $H_2$ (12 atm) and closed. The tube was placed behind a protective shield and the reaction mixture was heated in an oil bath at 110° C. with constant stirring for 60 h. After cooling to room temperature, excess $H_2$ was vented off carefully and the product was determined by GC and GC-MS. Some representative results are presented in Table 4 hereinbelow.

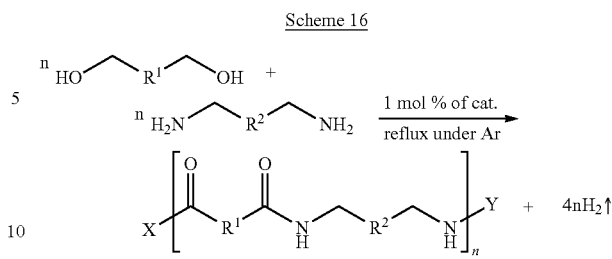

Scheme 16

Upon refluxing a 1,4-dioxane solution containing equimolar amounts of 1,6-hexanediol and 1,6-hexanediamine in the presence of 1 mol % of complex 1 under an argon atmosphere for 3 days, a white solid separated out in the reaction mixture. The solid was filtered off and successively washed with THF: EtOAc (1:1), dichloromethane and 20% methanol in water. The resultant white solid was dried under high vacuum at 80° C. for 12 hrs to afford polymer 3a in 82% yield (Table 5, entry 1). The solid was insoluble in MeOH, THF, 1,4-dioxane and chlorinated solvents, partially soluble in dimethylsulfoxide and dimethylformamide upon warming. The polyamide obtained was dissolved in deuterated trifluoroacetic acid (TFA) or trifluoroethanol (TFE) and characterized by NMR. The presence of $CH_2$ attached to the carbonyl group was confirmed by $^1H$ NMR, showing a broad singlet at 2.39 ppm for the four hydrogen atoms. A peak at 180.4 ppm in the

TABLE 4

Hydrogenation of cyclic di-peptides to amino alcohols selectively catalyzed by complex 1

| Entry | Cyclic di-peptides | Conditions | Amino alcohols (Yield (%)) |
|---|---|---|---|
| 1 | [structure: cyclic dipeptide with two benzyl groups] | Solvent = THF (2 mL)<br>$PH_2$ = 10 atm<br>Temperature = 110° C. (bath)<br>Time = 60 h | [structure: phenylalaninol] (58%) |
| 2 | [structure: bicyclic diketopiperazine from proline] | | [structure: prolinol] (67%) |

Example 4

Polyamides Synthesis from Diols and Diamines

The applicants have unexpectedly discovered that the catalysts of the present invention also catalyze the synthesis of polyamides directly from diols and diamines. In some preferred embodiments, 1,4-dioxane is used as a solvent. This polyamidation reaction is general, environmentally benign and atom economical. It proceeds under neutral reaction conditions without the use of activators, condensing agents or other additives. Moreover, these methods produce $H_2$ as the only byproduct (Scheme 16).

Figure 4A:
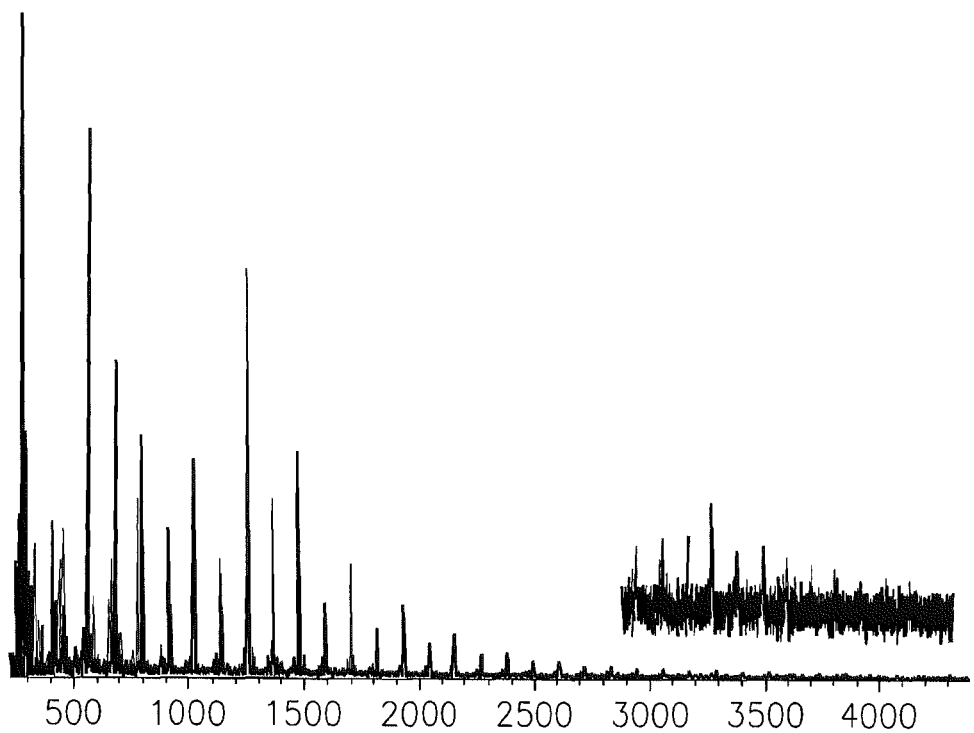
FIG. 4A: polyamide 3a in TFA using HBA matrix.

$^{13}C\{^1H\}$ NMR spectrum and an IR band at 1633 $cm^{-1}$ confirm the presence of the amide C=O group. The average molecular weight $M_n$ of the polyamide 3a was 16.6 kDa as measured by $^1H$ NMR using trifluoroethanol (TFE) as a solvent. The obtained solid was dissolved in TFA:$CH_3CN$ (1:1) and MALDI-TOF mass spectrum was recorded using DHB (2,5-dihydroxybenzoic acid) as the matrix (FIG. 4A). The polyamide has three possible types of end groups (amine-amine, amine-alcohol or alcohol-alcohol, compounds 3aa, 3ab and 3ac, respectively) and it also might result in a cyclic form. The spectrum revealed the highest molecular weight of 4195 Da, which corresponds to a polyamide having 18 monomers with OH/OH end groups. Due to insolubility of the polymer in DMF, GPC (gel permeation chromatography) was not performed.

Different Types of End Groups in Polyamide 3a:

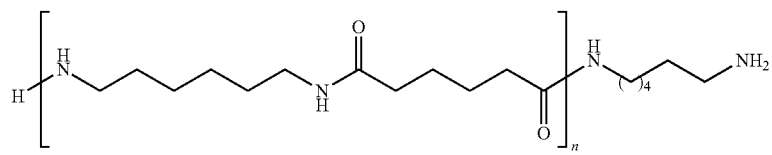

3aa

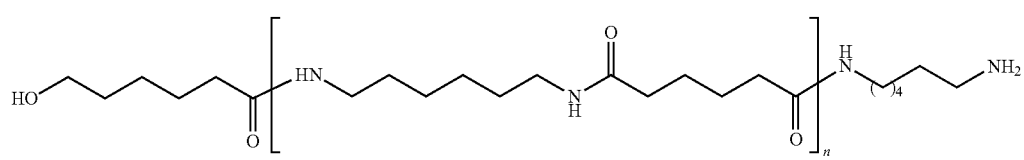

3ab

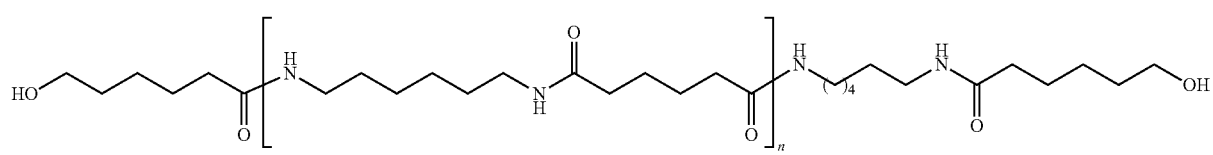

3ac

Refluxing of 1,10-decanediol and 1,6-hexanediamine in 1,4-dioxane in the presence of 1 mol % of complex 1 resulted in 88% yield of the polyamide 3b (Table 5, entry 2). The presence of the amide functional group of 3b was confirmed by IR, showing an absorption frequency at 1637 cm$^{-1}$ and a signal at 181.6 ppm in the $^{13}$C{$^1$H} NMR spectrum. The number average molecular weight of 3b was found to be 10.3 kDa based on $^1$H NMR spectra using trifluoroethanol (TFE) as a solvent. A MALDI-TOF mass spectrum indicated a molecular weight up to 4965 Da, which corresponds to a polyamide comprised of 18 monomers. Due to insolubility in DMF, GPC was not performed.

Figure 4B:
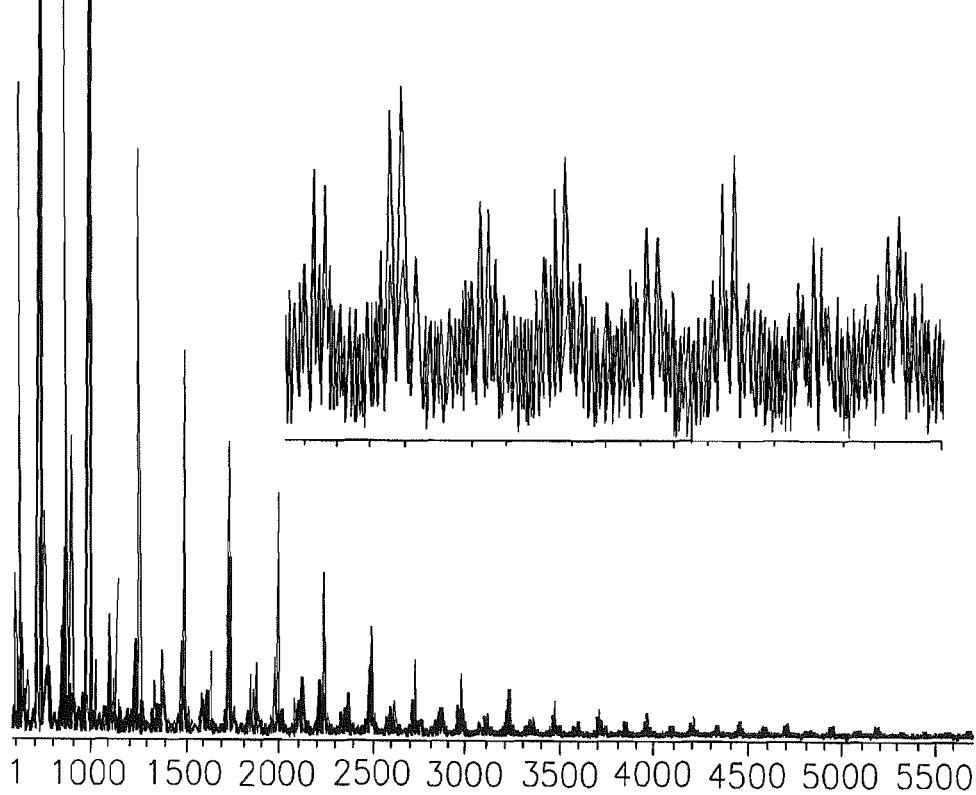
FIG. 4B: polyamide 3c in TFA using HBA matrix.

To further investigate the polyamidation reaction, various combinations of diols and diamines were studied. Thus, polyamidation reaction of 1,3-phenylenedimethanol and 1,6-hexanediamine with 1 mol % of complex 1 under argon atmosphere for 3 days resulted in a solid which was isolated by filtration. The solid was washed successively with THF: EtOAC (1:1), dichloromethane and 20% MeOH in water, and finally dried under high vacuum at 80° C. to afford 82% of compound 3c (Table 5, entry 3). The IR spectrum of the polyamide 3c showed the presence of the NH group as broad peak at 3297 cm$^{-1}$ and the amide C=O peak at 1631 cm$^{-1}$. The $^{13}$C{$^1$H} NMR spectrum exhibited the C=O carbon at 165.8 ppm. Polyamide 3c was further analyzed by MALDI-TOF by dissolving it in 80% TFA in acetonitrile using DHB as matrix (FIG. 4B). It gave a series of peaks in the range of 700-5932 Da. In an attempt to get a higher molecular weight, polyamide 3c was refluxed with- or without 1,3-phenylenedimethanol in the presence of the complex 1. However, a higher molecular weight was not observed. This might be due to the insolubility of 3c in 1,4-dioxane. Due to insolubility in DMF, GPC analysis was not performed.)

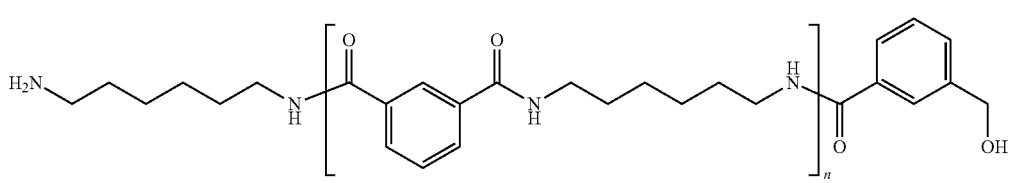

3c

Figure 4C:
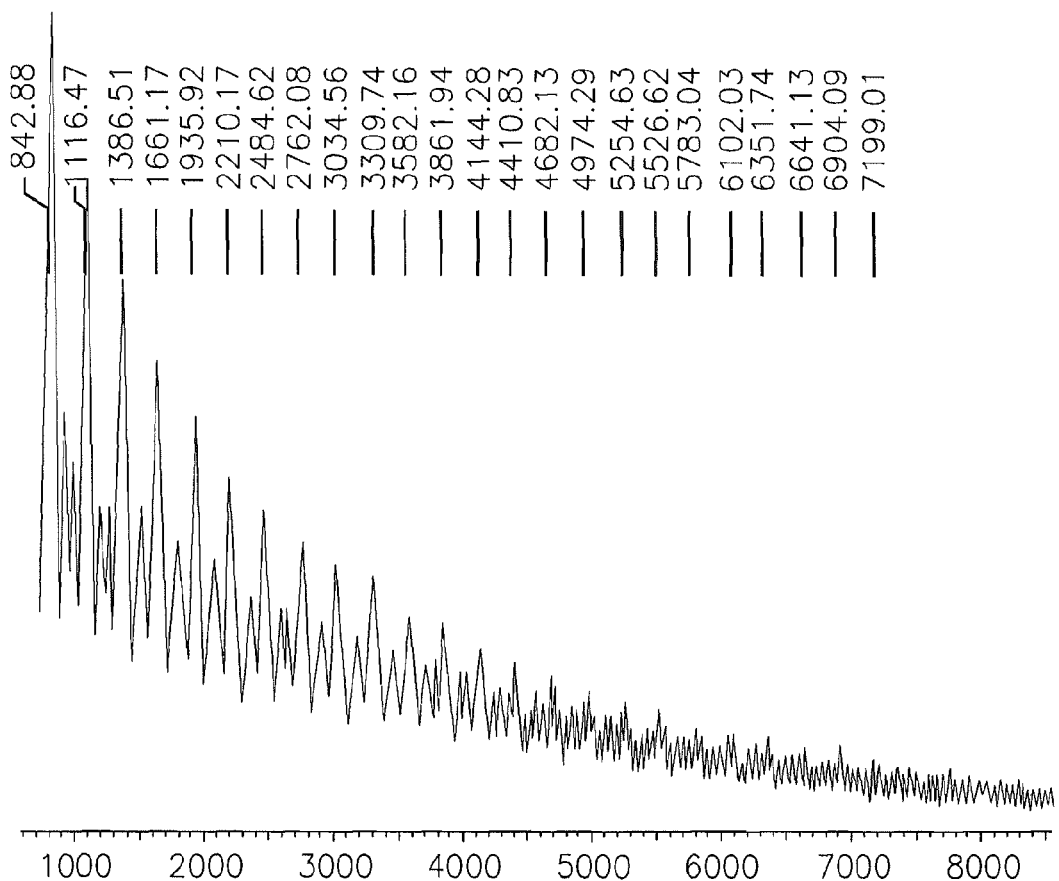
FIG. 4C: polyamide 3d in 50% TFA/DCM using HBA-NaI.

In order to increase the solubility of the polyamides, ether substituted aromatic diols were employed for the polymerization reactions. Thus, the reaction of (5-methoxy-1,3-phenylene)dimethanol and 1,6-hexanediamine gave 86% of compound 3d (Table 5, entry 4) as a gummy solid and exhibited a mass peak at 7199 Da in the MALDI-TOF spectrum using HBA+NaI as a matrix and a solution of the polyamide 3d in TFA: dichloromethane 1:1 (FIG. 4C). The polyamide 3d was dissolved completely in warm DMF and the molecular weight was measured using gel-permeation chromatography (GPC) using DMF with 0.1% LiBr (wt/v) as the eluent at a flow rate of 1.0 mL/min with column temperature at 50° C., yielding Mn=18.7 kDa with PDI of 2.08. The significantly lower molecular weight in MALDI-TOF when compared with GPC is likely to be a result of the high PDI. As previously reported, in case of polydispersities higher than PDI=1.2, MALDI-TOF leads to under-represented high-mass components with respect to the lower mass components, resulting in significantly lower average molecular weight values.

Figure 4D:
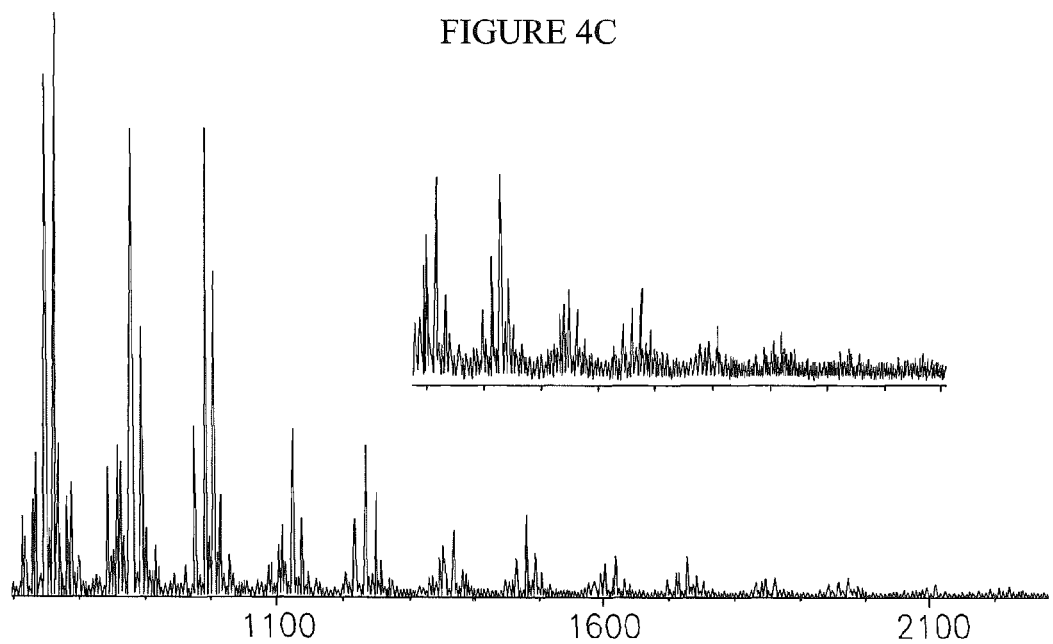
FIG. 4D: polyamide 3e in TFA using HBA matrix.

Exploring the scope of the polyamidation reaction, equivalent amounts of 1,4-phenylenedimethanol and 1,6-hexanediamine were refluxed with 1 mol % of complex 1 for 3 days, leading to 88% yield of the crude compound 3e (Table 5, entry 6). Successive washings with THF:EtOAC (1:1), dichloromethane, and 20% MeOH in water resulted in 80% yield of the solid after drying under vacuum. IR (peak at 1626 cm$^{-1}$) and NMR spectra confirm the presence of amide functionality. MALDI-TOF spectrum of the compound 3e in TFA:CH$_3$CN (1:1) revealed only oligomeric mixtures in the range of 700-2500 Da (FIG. 4D). The mass unit of 2322 Da corresponds to only 9 monomer units. Reaction of the shorter diamine 1,2-ethylenediamine with 1,4-phenylenedimethanol did not result in significant progress of the polyamidation reaction, giving the polyamide 3f in 63% yield (Table 5, entry 6), comprised of low molecular weight oligomeric mixtures in the range of 600-1900.

Next, the polyamidation reaction was examined using heteroaromatic diols. Thus, reaction of equivalent amounts of pyridine-2,6-diyldimethanol and 1,6-hexanediamine catalyzed by 1 mol % 1, furnished after 3 days of reflux in 1,4-dioxane the polyamide 3g (Table 5, entry 7) as a gummy insoluble solid which separated out from the reaction mixture and after work up gave a yield of 74%. The NMR and IR spectra confirm the presence of the amide carbonyl group. GPC analysis was performed for polyamide 3g using DMF as a solvent upon heating at 80° C. The Mn calculated from the GPC was 26.9 kDa with PDI of 1.98. The polyamide 3g was also analyzed by MALDI-TOF. The MALDI-TOF mass spectrum shows a series of peaks in the range of 600-4700 Da and the highest mass peak at 4583 appeared with low intensity and corresponds to 18 monomer units.

Figure 4E:
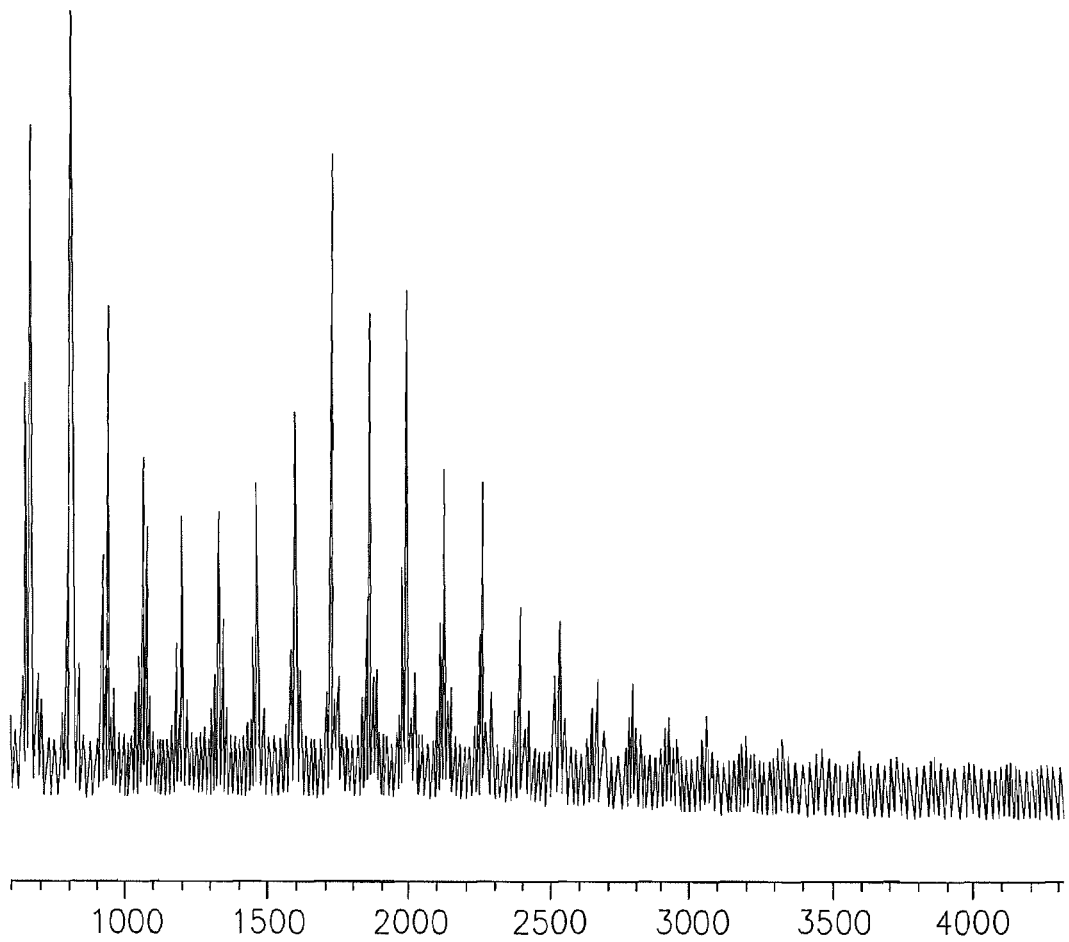
FIG. 4E: polyamide 3h in TFA using HBA matrix.

Next, aromatic diamines were studied for polyamidation reactions. Upon refluxing 1,4-phenylenedimethanol and 1,3-phenylenedimethanamine, a white solid was obtained after 3 days and was filtered off and dried under vacuum to provide 86% of polyamide 3h (Table 5, entry 8). The NMR and MALDI-TOF of 3h (FIG. 4E) reveal high molecular weight oligomeric mixtures. The highest mass unit obtained for the polyamide 3h was 3861 Da, having amine end groups and corresponding to 14 monomer units in the chain. The other oligomer peaks appear at 3594, 3328, 3062, 2796, 2530, 2264, 1732, 1466, 1200, 668 mass units. Further, heating the compound 3h in refluxing 1,4-dioxane in the presence of 1 mol % of the catalyst 1 did not result in progress of the polymer chain (due to insolubility in DMF, GPC analysis was not performed).

The polyamidation reaction of 1,4-phenylenedimethanol and 1,4-phenylenedimethanamine afforded a mixture of oligomers 3i in 84% isolated yield (Table 5, entry 9). The MALDI-TOF spectrum showed the highest mass unit of 3747 Da, indicating the presence of 14 monomer units. The reaction of 1,3-phenylenedimethanol and 1,3-phenylenedimethanamine led to 3j (Table 5, entry 10) in 78% yield after workup, with a maximum mass unit of 1467, corresponding to 5.5 monomer units. The reaction of 1,5-pentanediol and 1,4-phenylenedimethanamine gave 80% of compound 3k (Table 5, entry 11). Interestingly, 3k showed a series of mass peaks in the range of 500-5200 Da corresponding to 22 monomer units. Reaction of cyclohexane-1,4-diyldimethanol and 1,4-phenylenedimethanamine gave 66% of compound 3l (Table 5, entry 12), with peaks at 1912 Da corresponding to only 7 monomeric units in MALDI-TOF spectrum. (Due to insolubility in DMF, GPC analysis was not performed.)

Polyamidation of (5-methoxy-1,3-phenylene)dimethanol, 1,4-phenylenedimethanamine using 1 mol % catalyst 1 afforded compound 3m (Table 5, entry 13) in 76% yield, with the mass obtained at 4450 Da by MALDI-TOF, corresponding to 15 monomer units. The GPC analysis of 3m showed a molecular weight Mn=5.3 kDa. Similarly, the reaction of (5-(hexyloxy)-1,3-phenylene)dimethanol and 1,3-phenylenedimethanamine gave 88% of the polyamide 3n (Table 5, entry 14). The number average molecular weight Mn of 3n was 11.3 kDa based on GPC analysis. Reaction of (5-(hexyloxy)-1,3-phenylene)dimethanol and 1,4-phenylenedimethanamine gave 77% of the polyamide 3o (Table 5, entry 15) with a mass of 3052 Da corresponding to 8 monomers based on the MALDI-TOF spectrum.

Thus, a variety of polyamides have been synthesized having different spacers in good yield. The synthesis of polyamides using non-activated/non-ether linked substrates was demonstrated. The synthesized polyamides were characterized by spectroscopic techniques. The molecular weight was determined by $^1$H NMR and GPC analysis. The heteroaromatic polyamide 3g gave the highest number average molecular weight compared to the corresponding aliphatic and aromatic derived polyamides (3a and 3d respectively). MALDI-TOF spectra of insoluble polyamides was also obtained. The results are summarized in Table 5.

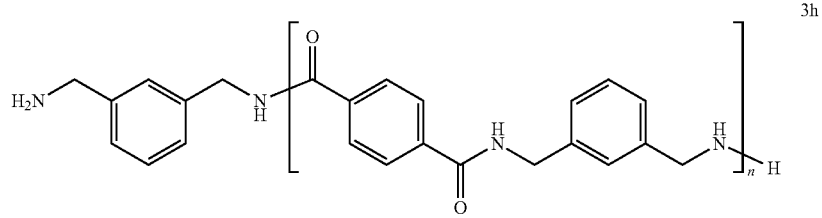

TABLE 5

Catalytic polyamidation using diols and diamines.[a]

| Entry | Diols | Diamines | Polyamides | Isolated Yield (%) |
|---|---|---|---|---|
| 1 | HO-(CH₂)₄-OH | H₂N-(CH₂)₄-NH₂ | 3a | 82 |
| 2 | HO-(CH₂)₈-OH | H₂N-(CH₂)₄-NH₂ | 3b | 88 |
| 3 | 1,3-benzenedimethanol | H₂N-(CH₂)₄-NH₂ | 3c | 82 |
| 4 | 5-methoxy-1,3-benzenedimethanol | H₂N-(CH₂)₄-NH₂ | 3d | 86 |
| 5 | 1,4-benzenedimethanol | H₂N-(CH₂)₄-NH₂ | 3e | 80 |
| 6 | 1,4-benzenedimethanol | H₂N-(CH₂)₂-NH₂ | 3f | 63 |
| 7 | 2,6-pyridinedimethanol | H₂N-(CH₂)₄-NH₂ | 3g | 74 |

TABLE 5-continued

| # | Diol | Diamine | Polymer | Yield (%) |
|---|---|---|---|---|
| 8 | HO-CH2-C6H4-CH2-OH (para) | H2N-CH2-C6H4-CH2-NH2 (meta) | 3h | 86 |
| 9 | HO-CH2-C6H4-CH2-OH (para) | H2N-CH2-C6H4-CH2-NH2 (para) | 3i | 84 |
| 10 | HO-CH2-C6H4-CH2-OH (meta) | H2N-CH2-C6H4-CH2-NH2 (meta) | 3j | 78 |
| 11 | HO-(CH2)4-OH | H2N-CH2-C6H4-CH2-NH2 (para) | 3k | 80 |
| 12 | HO-CH2-C6H10-CH2-OH | H2N-CH2-C6H4-CH2-NH2 (para) | 3l | 66 |
| 13 | HO-CH2-C6H3(OCH3)-CH2-OH | H2N-CH2-C6H4-CH2-NH2 (para) | 3m | 76 |
| 14 | HO-CH2-C6H3(OCH3)-CH2-OH | H2N-CH2-C6H4-CH2-NH2 (meta) | 3n | 88 |

TABLE 5-continued

| | | | | |
|---|---|---|---|---|
| 15 | 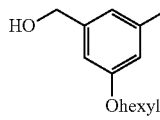 Ohexyl | 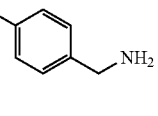 | 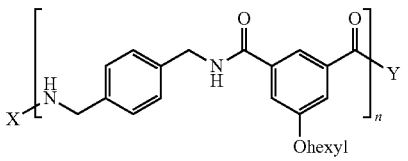 Ohexyl 3o | 77 |

| Entry | Highest molecular weight by MALDI-TOF (Da) | Mn (10³) | PDI |
|---|---|---|---|
| 1 | 4195 | 16.6[b] | — |
| 2 | 5000 | 10.3[b] | — |
| 3 | 5932 | — | — |
| 4 | 7199 | 18.7[c] | 2.08 |
| 5 | 2322 | — | — |
| 6 | 1849 | — | — |
| 7 | 4583 | 26.9[c] | 1.98 |
| 8 | 3861 | — | — |
| 9 | 3734 | — | — |
| 10 | 1467 | — | — |
| 11 | 5200 | — | — |
| 12 | 1912 | — | — |
| 13 | 4450 | 5.3[c] | 3.20 |
| 14 | — | 11.3[c] | 2.18 |
| 15 | 3052 | 5.4[c] | 2.51 |

Figure 5:
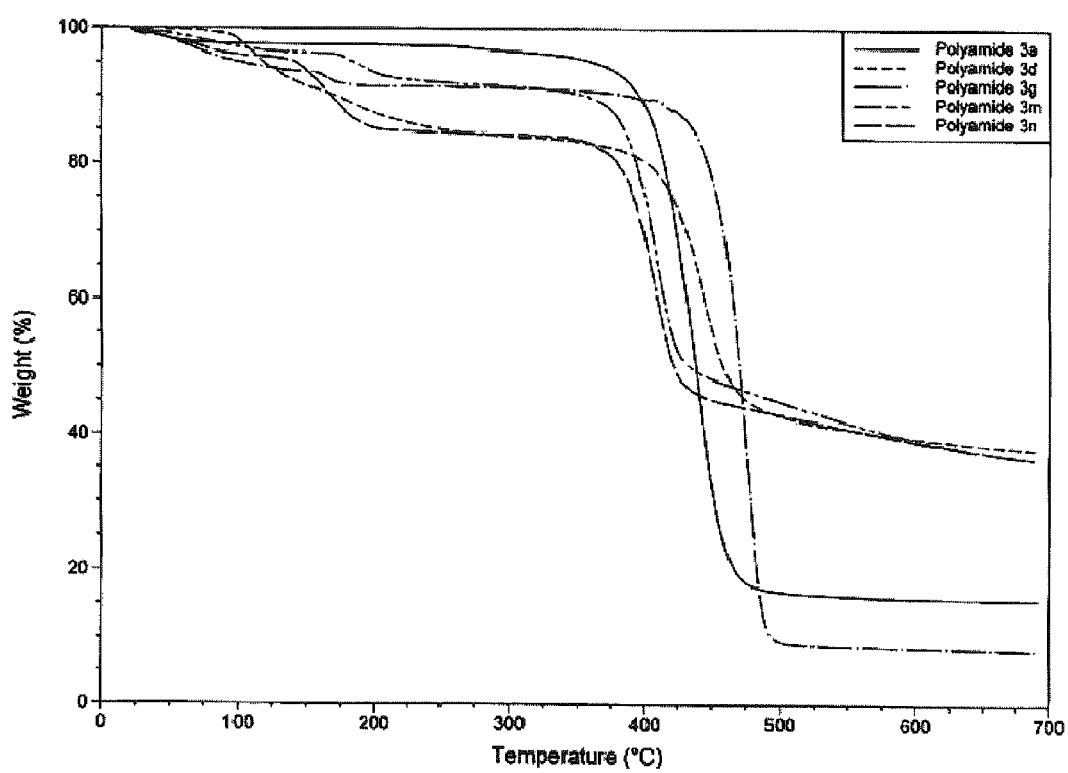
FIG. 5: TGA of polyamides 3.

[a]Complex 1 (0.01 mmol), diol (1 mmol), diamine (1 mmol) and 1,4-dioxane (2 mL) were refluxed at an oil bath temperature of 135° C. in a Schlenk tube under Argon for 3 days.
[b]Mn was calculated from ¹H NMR
[c]Mn was obtained from GPC analysis Thermogravimetric analyses (TGA) of the synthesized polyamides were performed. Weight losses of 30% and 50% occurred at similar temperatures and were not significantly dependent on polymer structure (FIG. 5, Table 6). However, the aliphatic polyamide 3a was less thermally stable and exhibited 83% weight loss at 495° C., while the arene-based polyamides 3d,m,n (except 3g) exhibited 62-70% weight loss at 680° C. (Table 6). The pyridine-based polyamide 3g was less stable, and exhibited 92% weight loss at 520° C.

TABLE 6

Thermal studies of polyamides 3 at various temperatures by TGA.

| Polyamides | Mn (10³) | T (° C. at 5% weight loss) | T (° C. at 10% weight loss) | T (° C. at 30% weight loss) | T (° C. at 50% weight loss) | T (° C. at 70% weight loss) |
|---|---|---|---|---|---|---|
| 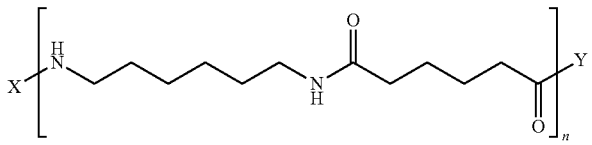 3a | 16.6 | 360 | 395 | 425 | 437 | 451 (70%) 495 (83%) |
| 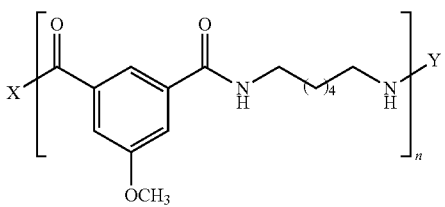 3d | 18.7 | 120 | 170 | 430 | 458 | 680 (62%) |

TABLE 6-continued

Thermal studies of polyamides 3 at various temperatures by TGA.

| Polyamides | Mn (10³) | T (° C. at 5% weight loss) | T (° C. at 10% weight loss) | T (° C. at 30% weight loss) | T (° C. at 50% weight loss) | T (° C. at 70% weight loss) |
|---|---|---|---|---|---|---|
| 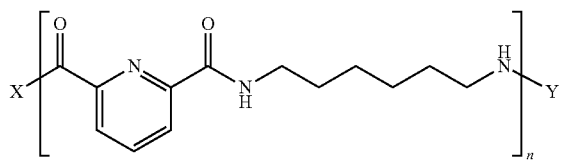 3g | 26.9 | 100 | 380 | 458 | 470 | 478 (70%) 520 (92%) |
| 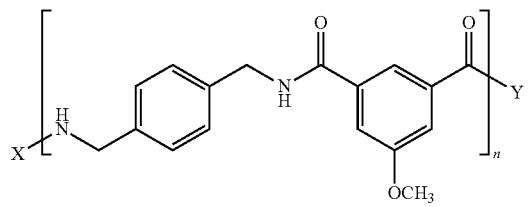 3m | 5.3 | 180 | 350 | 402 | 430 | 680 (64%) |
| 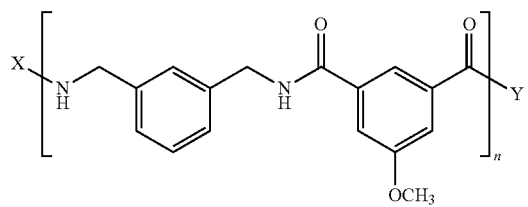 3n | 11.3 | 140 | 170 | 400 | 420 | 680 (64%) |

In conclusion, polyamidation based on coupling of non-activated diols and diamines, with extrusion of $H_2$, catalyzed by complex 1 was developed. Zeng et al. (38) published after the priority date of the present invention, have also reported the utilization of the amidation reaction catalyzed by complex 1 for the preparation of other polyamides, bearing ether-functionalized spacers.

The polyamidation reaction proceeds under neutral conditions, with liberation of molecular hydrogen and with no preactivation of the substrate being required. The reaction can be applied to a variety of diols and diamines for the synthesis of functional polyamides. The number average molecular weight of the polymers obtained in the processes of the present invention was measured by $^1$H NMR, MALDI-TOF and, in case of the DMF-soluble polymers, by GPC analysis. Mean molecular weights up to 26.9 kDa were obtained, with polydispersities in the range of PDI=1.98-3.2. The variation in chain lengths for different substrate combinations is probably influenced by the different solubilities of the polymers. The insoluble polyamides were characterised spectroscopically and by MALDI-TOF. It was observed that molecular weights determined by GPC were significantly higher than those obtained by MALDI-TOF. This is another example of the MALDI-TOF method favoring lower molecular weights in case of PDI>1.2 The thermal properties of the polyamides with different spacers were studied and it was found that aliphatic/pyridinic spacer-based polyamides are less stable at high temperature as compared with aromatic derived polyamides. This simple, environmentally benign and general polymerization reaction provides a new approach to the important area of polyamide synthesis.

General Procedure for the Catalytic Direct Polyamidation of Diols with Diamines Catalyzed by Complex 1

Complex 1 (0.01 mmol), diol (1 mmol), amine (1 mmol), and 1,4-dioxane (2 mL) were added to schlenk flask under an atmosphere of purified nitrogen in a glove box. The flask was equipped with a condenser and the solution was refluxed with stirring in an open system under argon flow for 3 days. During the course of the reaction, a white colored solid separated out for 24 hrs. The reflux was continued for 3 days. After cooling to room temperature, the solid obtained was filtered and washed successively with methanol and dichloromethane, or with THF:ethylacetate (1:1), dichloromethane and 20% methanol in water to give the product polyamide. T. The solid obtained was dried under vacuum at 80° C. for 8-12 hrs. The products were analyzed by NMR, IR and MALDI TOF.

Spectral Data for Polyamides:
Polyamide 3a:

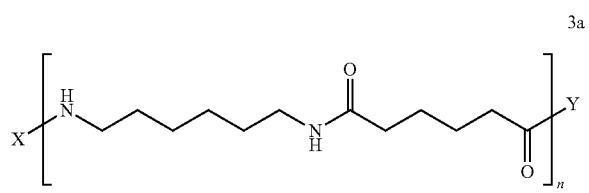

IR (KBr pellet): 3304, 2935, 2859, 1633, 1536, 1474, 1276 cm$^{-1}$; $^1$H NMR (TFA-d): 1.08 (broad s, 4H), 1.34 (broad s, 4H), 1.52 (broad s, 4H), 2.39 (broad s, 4H), 3.17 (broad s, 4H); $^{13}$C{$^1$H}NMR (TFA-d): 26.8, 27.8, 29.5, 35.0, 44.5, 180.4.

MALDI-TOF (matrix: HBA (2,5-dihydroxybenzoic acid), solvent acetonitrile: TFA): m/z=569 to 4195 Da. The spectrum of polyamide 3a shows a series of peaks at 569 (3aa+H$^+$ (n=2)), 795 (3aa+H$^+$ (n=3)), 909 (3ab+H$^+$ (n=3)), 1022 (3c (n=4)), 1135 (3ab+H$^+$ (n=4)), 1247 (3aa+H$^+$ (n=5)), 1361 (3ab+H$^+$ (n=5)), 1474 (3ac (n=6)), 1588 (3ab+2H$^+$ (n=6)), 1700 (3ac (n=7)), 1814 (3ab+2H$^+$ (n=7)), 1926 (3ac (n=8)), 2041 (3ab+3H$^+$ (n=8)), 2153 (3ac+H$^+$ (n=9)), 2266 (3ab+2H$^+$ (n=9)), 2379 (3ac+H$^+$ (n=10)), 2494 (3ab+4H$^+$ (n=10)), 2606 (3ac+2H$^+$ (n=11)), 2720 (3ab+4H$^+$ (n=11)), 2832 (3ac+2H$^+$ (n=12)), 2947 (3ab+5H$^+$ (n=12)), 3058 (3ac+2H$^+$ (n=13)), 3170 (3ab+H$^+$ (n=13)), 3288 (3ac+6H$^+$ (n=14)), 3402 (3ab+8H$^+$ (n=14)), 3515 (3ac+7H$^+$ (n=15)), 3625, 3739 (3ac+5H$^+$ (n=16)), 3840, 3853, 3966 (3ac+5H$^+$ (n=17)), 4079 (3ab+6H$^+$ (n=13)), 4195 (3ac+9H$^+$ (n=18)).

Polyamide 3b:

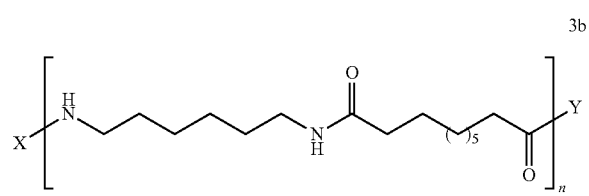

IR (KBr pellet): 3306, 2933, 2854, 1637, 1540, 1437, 1383, 1239 cm$^{-1}$; $^1$H NMR (TFA-d): 1.28 (broad s, 12H), 1.63 (broad s, 8H), 2.61 (broad s, 4H), 3.46 (broad s, 4H); $^{13}$C{$^1$H}NMR (TFA-d): 27.6, 29.3, 30.4, 35.5, 44.7, 181.6. MALDI-TOF (matrix: HBA (2,5-dihydroxybenzoic acid)+NaI, solvent dichloromethane: TFA): m/z=1258 to 4965 Da.

Polyamide 3c:

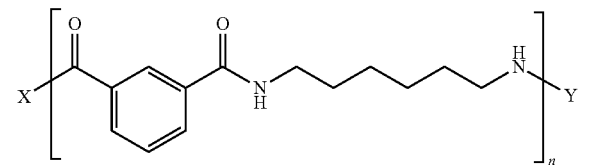

IR (KBr pellet): 3297, 2935, 2857, 1631, 1532, 1274 cm$^{-1}$; $^1$H NMR (DMSO-d$_6$): 1.32 (broad s, 4H, CH$_2$), 1.51 (broad s, 4H, CH$_2$), 3.23-3.32 (m, 4H, NCH$_2$), 7.50 (t, 1H, =CH), 7.91 (d, 2H, =CH), 8.26 (s, 1H, =CH), 8.54 (broad s, 2H, NH). $^{13}$C{$^1$H}NMR (DMSO-d$_6$): 26.2, 29.1, 39.2, 126.1, 128.2, 129.5, 134.9, 165.8. MALDI-TOF (matrix: 2,5-dihydroxybenzoic acid, solvent acetonitrile:TFA): m/z=700 to 5932 Da. The following peaks were observed: 5932 (3c (n=23)+24), 5918 (3c (n=23)+10), 5685 (3c (n=22)+23), 5671 (3c (n=22)+9), 5439 (3c (n=21)+23), 5425 (3c (n=21)+9), 5192 (3c (n=20)+22), 5178 (3c (n=20)+8), 4946 (3c (n=19)+22), 4932 (3c (n=19)+8), 4699 (3c (n=18)+21), 4685 (3c (n=18)+7), 4453 (3c (n=17)+21), 4439 (3c (n=17)+7), 4207 (3c (n=16)+21), 4193 (3c (n=16)+7), 3961 (3c (n=15)+21), 3947 (3c (n=15)+7), 3714 (3c (n=14)+20), 3700 (3c (n=14)+6), 3468 (3c (n=13)+20), 3454 (3c (n=13)+6), 3219 (3c (n=12)+17), 3205 (3c (n=12)+3), 2973 (3c (n=11)+17), 2959 (3c (n=11)+3), 2727 (3c (n=10)+17), 2713 (3c (n=10)+3), 2481 (3c (n=9)+17), 2467 (3c (n=9)+3), 2234 (3c (n=8)+16), 2220 (3c (n=8)+2), 1988 (3c (n=7)+16), 1974 (3c (n=7)+2), 1742 (3c (n=6)+16), 1728 (3c (n=6)+2), 1496 (3c (n=5)+16), 1482 (3c (n=5)+2). The excess mass units are due to the protonation of the amine functionality in TFA.

Polyamide 3d:

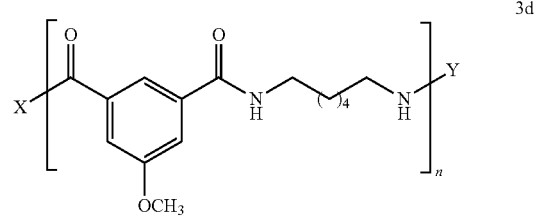

$^1$H NMR (DMSO-d$_6$): 1.32 (broad s, 4H, CH$_2$), 1.51 (broad s, 4H, CH$_2$), 3.15 (s, 2H, NCH$_2$), 3.38 (broad s, 2H, NCH$_2$), 3.82 (s, 3H, OCH$_3$), 7.48 (s, 2H, =CH), 7.88 (s, 1H, =CH), 8.53 (broad s, 2H, NH); $^{13}$C{$^1$H}NMR (DMSO-d$_6$): 26.3, 29.1, 48.6, 55.6, 66.4, 115.0, 119.1, 136.3, 159.1, 165.6;

GPC (0.1% LiBr in DMF): Mn=18.7×10$^3$ g/mol, Mw=39.1×10$^3$ g/mol

MALDI-TOF (matrix: 2,5-dihydroxybenzoic acid+NaI, solvent dichloromethane:TFA): m/z=1116 to 7199 Da. The MALDI-TOF exhibited a series of oligomeric peaks at 1116 (3d (n=4)+8H$^+$, NH$_2$/OH), 1386 (3d (n=5)+2H$^+$, NH$_2$/OH), 1661 (3d (n=6)+H$^+$, NH$_2$/OH), 1935 (3c (n=7)+3H$^+$, cyclic), 2210 (3d (n=8)+2H$^+$, cyclic), 2484 (3d (n=9), cyclic), 2762 (3d (n=10)+2H$^+$, cyclic), 3034, 3309, 3582, 3861, 4144 (3d (n=15), NH$_2$/OH), 4410, 4682, 4974 (3d (n=18)+2H$^+$, NH$_2$/OH), 5254 (3d (n=19)+6H$^+$, NH$_2$/OH), 5526 (3d (n=20)+2H$^+$, NH$_2$/OH), 6102 (3d (n=22)+Na+3H$^+$, NH$_2$/OH), 6351 (3d (n=23)+3, cyclic), 6641 (3d (n=24)+13, NH$_2$/OH), 6904 (3d (n=25), NH$_2$/OH) and 7199 (3d (n=26)+23, cyclic).

Polyamide 3e:

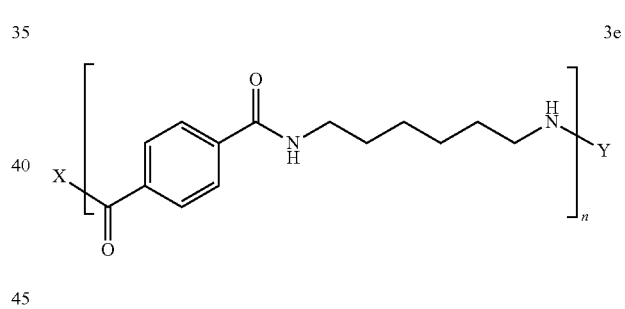

IR (KBr pellet): 3312, 2936, 2857, 1626, 1540, 1498, 1287 cm$^{-1}$. $^1$H NMR (DMSO-d$_6$): 1.29-1.51 (m, 8H), 3.23 (broad s, 4H), 4.52 (s), 5.32 (broad s), 7.36 (d), 7.78 (d), 7.87 (s), 8.38 (t), 8.54 (broad s).

MALDI-TOF (matrix=DHB, solvent acetonitrile: TFA): m/z=743 to 2322 Da. The oligomeric peaks are 743 (3e (n=3)+H$^+$), 989 (3e (n=4)+H$^+$), 1235 (3e (n=5)+H$^+$), 1482 (3e (n=6)+2H$^+$), 1728 (3e (n=7)+H$^+$), 1973 (3e (n=8)+H$^+$), 2221 (3e (n=9)+3H$^+$), 2464 (3e (n=10)+3H$^+$).

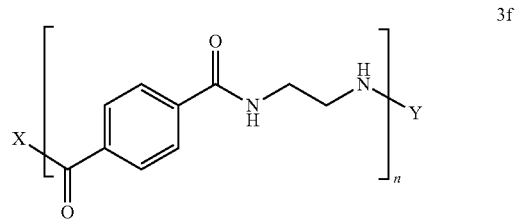

Polyamide 3f:

$^1$H NMR (DMSO-$d_6$): 2.67 (t), 3.44 (broad s), 4.53 (s), 7.37 (d), 7.80 (d), 7.90 (s), 8.56 (broad s), 8.71 (broad s). MALDI-TOF (matrix: 2,5-dihydroxybenzoic acid, solvent: acetonitrile: TFA): m/z=765 to 1835 Da. Oligomeric peaks were observed at 765 (3f(n=4)+H$^+$), 955 (3f(n=5)+H$^+$), 1145 (3f (n=6)+H$^+$), 1335 (3f (n=7)+H$^+$), 1525 (3f (n=8)+H$^+$), 1715 (3f(n=9)+H$^+$), 1849 (3f(n=9)+H$^+$, ending with OH/OH groups).

Polyamide 3g:

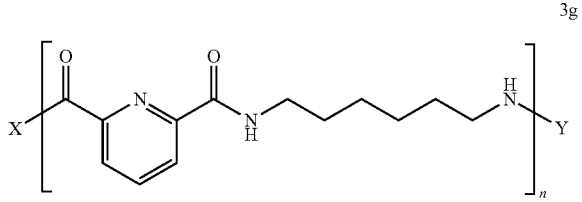

IR (KBr pellet): 3325, 2932, 2859, 1662, 1538, 1445, 1243 cm$^{-1}$; $^1$H NMR (DMSO-$d_6$): 1.27 (broad m, 4H, CH$_2$), 1.50 (broad m, 4H, CH$_2$), 3.29 (broad s, 4H, NCH$_2$), 8.13 (m, 3H, =CH), 9.28 (broad s); $^{13}$C NMR (DMSO-$d_6$): 13.9, 22.1, 26.1, 29.4, 30.9, 40.1, 124.1, 139.3, 148.8, 163; GPC (0.1% LiBr in DMF): Mn=26.9×10$^3$g/mol, Mw=53.3×10$^3$g/mol MALDI-TOF (matrix: 2,5-dihydroxybenzoic acid, solvent acetonitrile: TFA): m/z=610 to 4583 Da. The spectrum exhibits a series of oligomeric peaks at 610 (3g (n=2), NH$_2$/NH$_2$), 742 (3g (n=3)+H$^+$, cyclic), 907 (3g (n=3)+Na$^+$+3H$^+$, OH/OH), 989 (3g (n=4)+H$^+$, cyclic), 1203, 1236 (3g (n=5)+H$^+$, cyclic), 1484 (3g (n=6)+2H$^+$, cyclic), 1500, 1732 (3g (n=7)+3H$^+$, cyclic), 1781, 1796, 1914, 1978 (3g (n=8)+2H$^+$, cyclic), 2063, 2079, 2092, 2210, 2226 (3g (n=9)+3H$^+$, cyclic), 2242, 2360, 2374, 2389, 2473 (3g (n=10)+3H$^+$, cyclic), 2492, 2507, 2657, 2671, 2685, 2789, 2803, 2836, 2953, 2968, 2981, 3085, 3100, 3132, 3250, 3264, 3278, 3396 (3g (n=13)+3Na$^+$, NH$_2$/NH$_2$), 3427 (3g (n=13)+KK, OK/OH), 3561, 3576 (3g (n=14)+2H$^+$, NH$_2$/NH$_2$), 3679, 3709 (3g (n=15)+3H$^+$, cyclic), 3726, 3844 (3g (n=15)+Na$^+$, NH$_2$/NH$_2$), 3975 (3g (n=16)+Na$^+$, cyclic), 4449 (3g (n=18)+3H$^+$, cyclic), 4569 (3g (n=18)+7H$^+$, NH$_2$/NH$_2$).

Polyamide 3h:

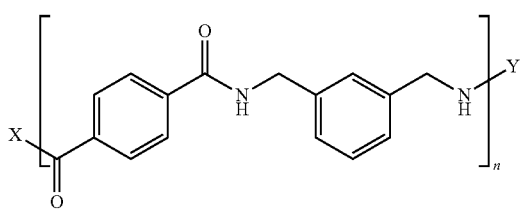

IR (KBr pellet): 3285, 2921, 1638, 1540, 1439, 1318 cm$^{-1}$. $^1$H NMR (DMSO-$d_6$): 3.68 (s), 4.47 (broad s), 7.21-7.37 (broad m), 7.92-7.94 (m), 9.15 (broad s); $^{13}$C{$^1$H}NMR (DMSO-$d_6$): 42.7, 45.5, 62.6, 125.2, 125.8, 126.1, 127.2, 136.6, 139.6, 165.6; MALDI-TOF (matrix: 2,5-dihydroxybenzoic acid, solvent acetonitrile: TFA): m/z=668 to 3861 Da.

Polyamide 3i:

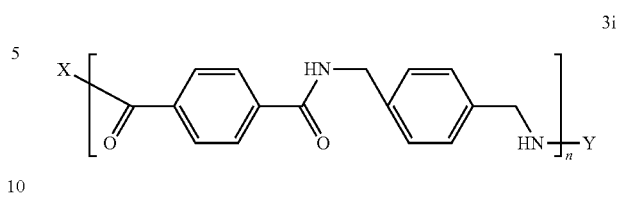

IR (KBr pellet): 3346, 3056, 2923, 1640, 1540, 1496, 1317 cm$^{-1}$; $^1$H NMR (DMSO-$d_6$): 3.59 (s), 4.43 (broad m), 7.23-7.27 (broad m), 7.37 (d), 7.83 (d), 7.94 (m), 9.13 (broad s); $^{13}$C{$^1$H}NMR (DMSO-$d_6$): 42.4, 45.1, 62.4, 126.0, 127.1, 132.7, 137.5, 137.9, 138.0, 138.3, 142.1, 145.9, 165.5, 166.1; MALDI-TOF (matrix: 2,5-dihydroxybenzoic acid, solvent ACETONITRILE: TFA): m/z=400 to 3734 Da Polyamide 3j:

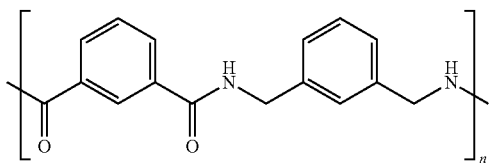

IR (KBr pellet): 3290, 3061, 2920, 1640, 1533, 1478, 1272 cm$^{-1}$; $^1$H NMR (DMSO-$d_6$): 4.45-4.47 (m, 4H), 7.17-7.28 (m, 4H), 7.50 (t, 1H), 7.97 (d, 2H), 8.36 (s, 1H), 9.13 (broad m, 2H); $^{13}$C{$^1$H}NMR (DMSO-$d_6$): 42.8, 66.4, 125.6, 126.5, 126.7, 128.5, 128.7, 129.9, 134.6, 139.7, 165.9.

GPC (0.1% LiBr in DMF): Mn=1.4×10$^3$g/mol, Mw=5.01×10$^3$ g/mol

MALDI-TOF (matrix: 2,5-dihydroxybenzoic acid, solvent acetonitrile: TFA): m/z=500 to 1467 Da Polyamide 3k:

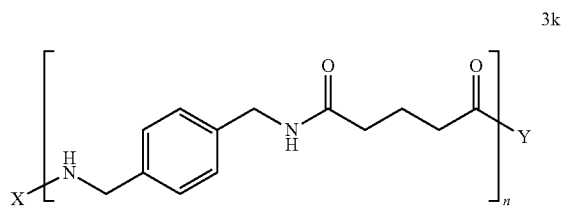

IR (KBr pellet): 3245, 3069, 2964, 2944, 1629, 1556, 1424, 1262 cm$^{-1}$; $^1$H NMR (DMSO-$d_6$): 1.35-1.79 (m, 2H), 2.07-2.15 (m, 4H), 4.19-4.21 (broad m, 4H), 7.16 (broad s, 4H), 8.27 (broad m); $^{13}$C{$^1$H}NMR (DMSO-$d_6$): 21.3, 21.9, 32.9, 35.0, 41.7, 46.8, 61.1, 127.0, 127.3, 138.1, 171.6. MALDI-TOF (matrix=DHB, solvent acetonitrile: TFA): m/z=500 to 5200 Da Polyamide 3l:

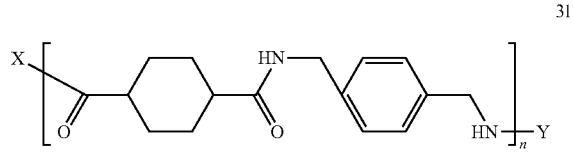

IR (KBr pellet): 3282, 3060, 2934, 2860, 1633, 1551, 1443, 1386 cm$^{-1}$; $^1$H NMR (TFA-d): 7.26 (d), 7.19 (d), 7.11 (broad s), 4.44 (broad s), 4.18 (s), 3.83 (s), 2.56 (broad s), 2.00 (broad s), 0.92-1.82 (m); $^{13}$C{$^1$H}NMR (TFA-d): 29.3, 45.2, 46.9, 130.6, 131.0, 131.9, 139.2, 182.7. MALDI-TOF (matrix=DHB, solvent acetonitrile: TFA): m/z=400 to 1912 Da Polyamide 3m:

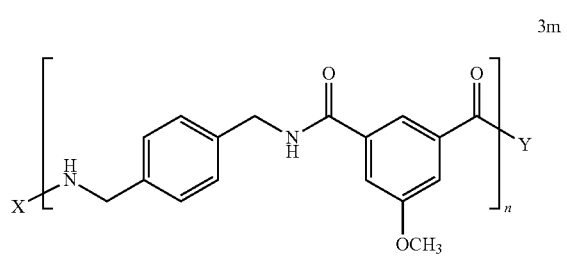

3m

IR (KBr pellet): 3294, 3063, 2935, 1642, 1593, 1536, 1423, 1283, 1061 cm$^{-1}$. $^1$H NMR (DMSO-d$_6$): 3.56 (s), 3.81 (s), 4.42 (broad s), 7.24 (broad s), 7.54 (s), 7.96 (s), 9.11 (broad s); $^{13}$C{$^1$H}NMR (DMSO-d$_6$): 42.5, 55.6, 66.3, 115.3, 118.7, 127.3, 135.9, 138.0, 159.1, 165.5, 165.8;

GPC (0.1% LiBr in DMF): Mn=5.39×10$^3$ g/mol, Mw=17.3737×10$^3$ g/mol

MALDI-TOF (matrix: 2,5-dihydroxybenzoic acid, solvent acetonitrile: TFA): m/z=600 to 4450 Da

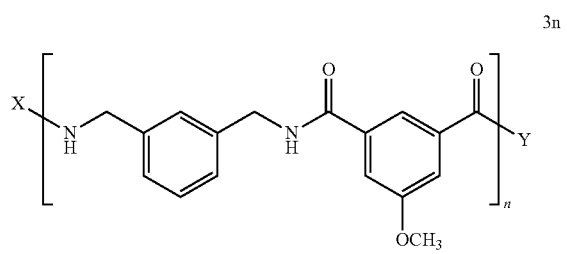

3n $^1$H NMR (TFA-D): 3.74 (s, 2H, NCH$_2$), 3.88 (s, 2H, NCH$_2$), 4.60 (s, 3H, OCH$_3$), 7.19-7.23 (m, 4H, Arom-H); 7.44 (s, 2H, Arom-H), 7.77 (s, 1H, Arom-H); $^{13}$C{$^1$H}NMR (TFA-D): 47.2, 57.6, 68.7, 119.7, 121.1, 129.0, 129.8, 131.9, 136.3, 138.5, 162.3, 173.0; GPC (0.1% LiBr in DMF): Mn=11.3×10$^3$ g/mol, Mw=24.71×10$^3$ g/mol Polyamide 3o:

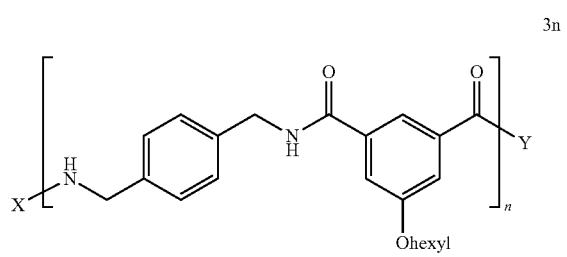

3n

IR (KBr pellet): 3325, 3079, 2929, 2869, 1644, 1592, 1532, 1434, 1333, 1062 cm$^{-1}$; $^1$H NMR (TFA-d): 7.78 (s, 1H), 7.46 (s, 2H), 7.21 (s, 4H), 4.56 (broad s, 4H), 3.94 (broad s, 2H), 1.65 (broad s, 2H), 1.26 (broad s, 2H), 1.15 (broad s, 4H), 0.70 (broad s, 3H); $^{13}$C{$^1$H}NMR (TFA-d): 14.5, 24.1, 27.1, 30.5, 33.2, 47.0, 72.1, 120.4, 121.0, 130.5, 136.0, 137.8, 162.1, 173.0.

GPC (0.1% LiBr in DMF): Mn=5.4×10$^3$ g/mol, Mw=13.76×10$^3$ g/mol

MALDI-TOF (matrix=DHB, solvent acetonitrile: TFA): up to m/z=3052 Da

Example 5

Dehydrogenation of L-Alaninol to Form Poly(Alanine)

Scheme 17

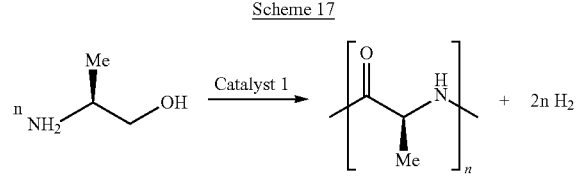

Complex 1 (0.01 mmol), L-alaminol (1 mmol), and 1,4-dioxane (2 mL) were taken in a Schlenk flask under an atmosphere of purified nitrogen in a glove box. The flask was taken out the glove box, and equipped with a condenser. The solution was refluxed with stirring in an open system under argon for 48 h. After cooling to room temperature, the solvent was concentrated (~0.5 mL) under reduced vacuum followed by addition of CH$_2$Cl$_2$ (in order to remove the unreacted starting material). The white solid precipitated out from the solution at ~5° C. (after 30 min) and was collected by simple filtration and washed with toluene and dried under vacuum at 80° C. for about 14 h to yield the desired polypeptide in 72% yield.

Poly(Alanine):

mp: 190-194° C. (decompose) $^1$H NMR (400 MHz, DMSO-d$_6$): 0.93 (broad s, 3H, CH$_3$), 4.22-4.26 (m, 1H, NCH), 8.00 (1H, CONH). $^{13}$C{$^1$H}NMR (300 MHz, TFA-d$_4$): 20.0 (CH$_3$), 21.7 (CH$_3$), 53.1 (NCH), 53.4 (NCH), 174.9 (C=O).

MS (ES$^+$): 165.3 (100%, cycloala-ala+Na$^+$), 240 (18%, M (n=1)+Na), 311 (65%, M (n=2)+Na), 382 (32%, M (n=3)+Na)), 453 (10%, M (n=4)+Na)), 524 (6%, M (n=5)+Na)). Maldi-T of: 754 ((M (n=8)+K+H)), 903 ((M (n=10)+2Na+H)), 1001 ((M (n=12)+3H)), 1150 ((M (n=14)+10H)), 1248, 1396 ((M (n=17)+K+3H)), 1494 ((M (cyclic, n=21)+3H), 1644 ((M (n=23)+7H)). [α]=−105° (50 mg/5 mL, Acetic Acid)

Example 6

Direct Synthesis of Amides from Esters Using Ruthenium-Pincer Catalyst with Liberation of H$_2$ Under Neutral Conditions PNN-type pincer ruthenium complexes used for catalytic conversion of esters and amines into amides:

Scheme 18

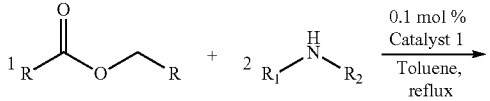

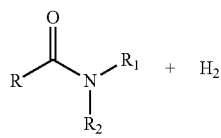

The applicants of the present invention have discovered that amide synthesis from esters and amines can be achieved using the ruthenium PNN catalyst 1. The reaction is general, efficient, environmentally benign and atom economical. It proceeds under neutral conditions without acid/base/activators/promoters. Notably, this reaction affords with amide in high TON (1000) and $H_2$ as the only byproduct (Scheme 18).

When a benzene solution containing 10 mmol of pyrrolidine, 10 mmol of ethyl acetate and 0.01 mmol of complex 1 was refluxed under Argon atmosphere, quantitative conversion of pyrrolidine was observed by GC after 28 hrs, to yield 98% of N-acetyl pyrrolidine after column purification (Table 7, entry 1). The N-acetyl pyrrolidine was characterized by NMR and GC-MS. Similar results were obtained in toluene. Reaction of ethyl acetate with morpholine in benzene under reflux resulted after 36 hrs in 79% conversion with the isolation of the corresponding amide in 77% yield (Table 7, entry 2). Refluxing of 1-methyl piperazine, ethyl acetate and benzene in the presence of complex 1 provides the corresponding amide in 56% yield with the conversion of the ester being 59% (Table 7, entry 3).

Various esters and amines reacted similarly. Refluxing a toluene solution containing butyl butyrate (5 mmol), piperidine (10 mmol) and 0.1 mol % of the PNN complex 1 under argon atmosphere for 19 hrs resulted in 100% conversion of piperidine as observed by GC analysis, with the exclusive formation of the 1-(piperidin-1-yl)butan-1-one in 94% yield after isolation from alumina column chromatography (Table 7, entry 4). The product was completely characterized by NMR spectroscopy. Unlike the traditional methods, this reaction does not form any alcohol as by-product, resulting in the irreversible, unique incorporation of both the acyl and alkoxo parts of the starting ester into the product amide. Significantly the TON of ester-amide exchange reaction was high (1000). Similarly, refluxing the toluene solution containing butyl butyrate, morpholine or N-methyl piperazine in the presence of complex 1 resulted in 100% conversion of the amine with the isolation of the amides in 95 and 94% yields, respectively. Refluxing of excess of butyl butyrate and piperazine in toluene led to bis-acylation of the piperazine, providing the corresponding amide in 61% yield.

To explore the synthetic utility of this reaction, pentyl pentanoate was reacted with various amines. The reaction of pentyl pentanoate with piperidine gave 100% conversion with the isolation of the amide in 96% yield. Morpholine and N-methyl piperazine furnished the respective amide in 96 and 94% isolated yield.

Next, reactions were studied with primary amines. The reaction of ethyl butyrate and hexyl amine in the presence of 0.1 mol % of 1 in refluxing toluene led to 100% conversion of the hexyl amine with the isolation of 97% of the corresponding amide as the only product. Similarly, reaction of pentyl pentanoate and 4-methylbenzyl amine in refluxing toluene resulted in 100% conversion with isolation of corresponding amide in 98% yield. These reactions did not lead any alcohol as waste product.

The reactions were also studied in absence of solvent. Thus, heating pentylpentanoate, piperidine and complex 1 at 135° C. resulted in 52% conversion.

TABLE 7

Amination of esters catalyzed by the ruthenium complex 1[a]

| Entry | Ester | Amine | Time (hrs) | Conv. of amine | Isolated Yield (%) |
|---|---|---|---|---|---|
| 1 | | | 26 | 100 | 99 |
| 2 | | | 36 | 79 | 77 |

TABLE 7-continued

Amination of esters catalyzed by the ruthenium complex 1[a]

| Entry | Ester | Amine | Time (hrs) | Conv. of amine | Isolated Yield (%) |
|---|---|---|---|---|---|
| 3 | ethyl acetate | 1-methylpiperazine | 24 | 59 | 1-acetyl-4-methylpiperazine<br>56 |
| 4 | butyl butyrate | piperidine | 19 | 100 | 1-butyrylpiperidine<br>94 |
| 5 | butyl butyrate | morpholine | 21 | 100 | 4-butyrylmorpholine<br>95 |
| 6 | butyl butyrate | 1-methylpiperazine | 24 | 100 | 1-butyryl-4-methylpiperazine<br>94 |
| 6 | butyl butyrate | piperazine | 36 | 100 | 1,4-dibutyrylpiperazine<br>61 |

TABLE 7-continued

Amination of esters catalyzed by the ruthenium complex 1[a]

| Entry | Ester | Amine | Time (hrs) | Conv. of amine | Isolated Yield (%) |
|---|---|---|---|---|---|
| 7 | pentyl pentanoate | piperidine | 19 | 100 | 1-(piperidin-1-yl)pentan-1-one, 96 |
| 8 | pentyl pentanoate | morpholine | 26 | 100 | 1-morpholinopentan-1-one, 92 |
| 9 | pentyl pentanoate | N-methylpiperazine | 24 | 100 | 1-(4-methylpiperazin-1-yl)pentan-1-one, 94 |
| 10 | hexyl hexanoate | pyrrolidine | 18 | 100 | 1-(pyrrolidin-1-yl)hexan-1-one, 97 |
| 11 | hexyl hexanoate | piperidine | 26 | 100 | 1-(piperidin-1-yl)hexan-1-one, 94 |

TABLE 7-continued

Amination of esters catalyzed by the ruthenium complex 1[a]

| Entry | Ester | Amine | Time (hrs) | Conv. of amine | Isolated Yield (%) |
|---|---|---|---|---|---|
| 12 | (pentyl pentanoate structure) | morpholine | 18 | 100 | (1-morpholino-hexan-1-one) 93 |
| 13 | (butyl butanoate structure) | hexylamine | 24 | 100 | (N-hexylbutanamide) 97 |
| 14 | (pentyl pentanoate structure) | 4-methylbenzylamine | 18 | 100 | (N-(4-methylbenzyl)pentanamide) 98 |

[a]Complex 1 (0.01 mmol), ester (5 mmol), amine (10 mmol) and toluene/benzene (3 ml) were refluxed at an oil bath temperature of 135° C. in a Schlenk tube. Conversion of amine was analyzed by GC using m-xylene as internal standard.

In summary, acylation of amines using esters as the acylating partner is efficiently catalyzed by complex 1 under neutral conditions. The use of symmetrical esters results in the incorporation of both the acyl and alkoxo parts of the substrate ester into the product amide with liberation of $H_2$. This offers an environmentally benign, atom economical method for amide synthesis from esters without any waste generation. This catalytic cycle produces a high turnover number (1000) and both primary and secondary amines can be used.

Example 7

Ruthenium-Pincer Catalyzed Acylation of Alcohols Using Esters with Liberation of $H_2$ Under Neutral Conditions The acylation of esters with secondary alcohols can be carried out selectively to give the mixed ester using the PNN catalyst 1. The reaction is general, efficient, and environmentally benign. It proceeds under neutral conditions without acids or bases, activators, or molecular sieves. Uniquely, when a symmetrical ester (such as ethyl acetate) is reacted with a secondary alcohol, the only co-product is molecular hydrogen, unlike the generally employed transesterification reaction which gives an alcohol co-product (or its derivative) (Scheme 19).

Scheme 19. Acylation of alcohols using esters.

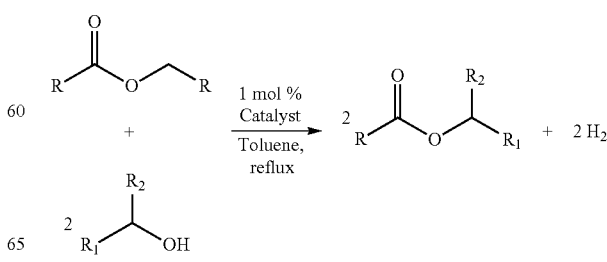

When a benzene solution containing 15 mmols of cyclohexanol, 5 mmols of ethyl acetate and 0.05 mmols of complex 1 was refluxed under argon atmosphere, GC analysis after 28 hrs showed that all of the ethyl acetate disappeared and cyclohexyl acetate was formed as a single product (Table 8, entry 1). $^1$H NMR and GC-MS of the isolated product were identical to cyclohexyl acetate prepared by refluxing neat acetic anhydride with cyclohexanol.

Likewise, refluxing a toluene solution containing one equivalent of hexyl hexanoate, 2 equivalents of cyclohexanol and 1 mol % of the PNN complex 1 under argon atmosphere for 20 h resulted in 84% conversion of hexyl hexanoate as determined by GC analysis, with the exclusive formation of the ester cyclohexyl hexanoate in 83% yield (Table 8, entry 2). Notably, unlike the traditional transesterification methods, this reaction does not form an alcohol product; rather, an irreversible incorporation of both the acyl and alkoxo parts of the starting ester into the product ester takes place. While 2 equivalents of the alcohol with respect to the ester are sufficient, somewhat higher yields are obtained when 3 equivalents of alcohol were used. Thus, reaction of 3 equivalents of cyclohexanol with hexyl hexanoate resulted after 26 h in 96% conversion with 95% yield of cyclohexyl hexanoate, as observed by GC, and confirmed by GC-MS by comparison with an authentic sample (Table 8, entry 3). The pure product was isolated by evaporation of the solvent followed by passing through a basic alumina plug and analysis by NMR and GC-MS. Use of the PNP complexes 2 or 3 resulted after 20 h in 58% or 17% yield of cyclohexyl hexanoate, respectively. Studying the scope of this new reaction with regard to the secondary alcohol, reaction of hexyl hexanoate with cyclopentanol in the presence of 1 mol % 1 was carried out. After 26 h reflux in toluene, cyclopentyl hexanoate (70% yield) was formed, with 71% conversion of hexyl hexanoate (Table 8, entry 4). Similarly, upon reaction of hexyl hexanoate with excess of 1-phenylethanol, 50% conversion of hexyl hexanoate with the formation of 49% of the acylated product was observed (Table 8, entry 5). The lower conversion of the ester is a result of facile dehydrogenation of 1-phenylethanol to acetophenone (49%). Because of the expected easy dehydrogenation of the isopropyl alcohol to acetone, transesterification with this alcohol was performed in a closed vessel, to retard this dehydrogenation process. Thus, heating hexyl hexanoate with excess of isopropyl alcohol resulted after 19 h in 83% conversion of hexyl hexanoate with the formation of isopropyl hexanoate in 67% yield (entry 6). The reaction of hexyl hexanoate and 3-pentanol led to 91% conversion of the ester with formation of 3-pentyl hexanoate in 90% yield after 26 h reflux (entry 7).

Exploring further the scope with regard to the ester substrate, pentyl pentanoate was reacted with cyclohexanol, resulting in 93% conversion with the formation of 93% cyclohexyl pentanoate (entry 8). Like in the case of hexyl hexanoate, the presumably formed pentanol intermediate is converted into pentyl pentanoate with the liberation of $H_2$. Similarly, treatment of pentyl pentanoate with cyclopentanol, 1-phenylethanol and 3-pentanol, furnished 87, 51, 91% conversion of pentyl pentanoate, respectively, with the predominant formation of the corresponding cross-ester as the product in 85, 49, 90% yields, respectively (entries 9-11).

Next we studied the reaction of butyl butyrate with various secondary alcohols. Reaction of 5 mmol of butyl butyrate with 15 mmol of cyclohexanol led to 93% conversion of the ester with the formation of 92% of cyclohexyl butyrate after 34 h (entry 12). Upon refluxing of butyl butyrate with cyclopentanol, after 28 hrs 75% conversion of the ester, with formation of 74% cyclopentyl butyrate were observed (entry 13). In a similar reaction with 1-phenylethanol or 3-pentanol, 41 and 77% conversion, respectively, into the product was noted by GC analysis after 36 h (entries 14 and 15).

These reactions were also studied with unsymmetrical esters. The reaction of ethyl butyrate with 3-pentanol in the presence of 1 mol % of 1 under refluxing toluene led to 75% conversion of ethyl butyrate with the formation of 73% of 3-pentyl butyrate as the exclusive product (entry 16). Traces of 3-pentyl acetate, resulting from reaction with the formed ethanol, were also observed. The remaining ethanol probably evaporated from the reaction mixture under the reflux conditions. Similarly, the reaction of methyl hexanoate with cyclohexanol results in 42% conversion after 17 h with the formation of 42% of cyclohexyl hexanoate (entry 17).

Since the dehydrogenation of the secondary alcohol to ketone is slower than the dehydrogenative coupling of the primary alcohol to ester, most of the secondary alcohol reacts with the ester, although some ketone resulting from excess alcohol was observed. The slow reaction of the secondary alcohol with PNN complex may be due to the steric hindrance.

TABLE 8

Acylation of alcohols catalyzed by the ruthenium complex 1[a]

| Entry | Ester | alcohol | Time (hrs) | Conv. of ester % | Yield % |
|---|---|---|---|---|---|
| 1[b] | ethyl acetate | cyclohexanol | 28 | 100 | cyclohexyl acetate, 95 |
| 2[c] | hexyl hexanoate | cyclohexanol | 20 | 84 | cyclohexyl hexanoate, 83 |

TABLE 8-continued

Acylation of alcohols catalyzed by the ruthenium complex 1[a]

| Entry | Ester | alcohol | Time (hrs) | Conv. of ester % | Yield % |
|---|---|---|---|---|---|
| 3 | pentyl pentanoate | cyclohexanol | 26 | 96 (cat 1) 58 (cat. 2) 17 (cat. 3) | cyclohexyl pentanoate 95 (cat 1) |
| 4 | hexyl hexanoate | cyclopentanol | 26 | 71 | cyclopentyl hexanoate 70 |
| 5 | pentyl pentanoate | 1-phenylethanol | 36 | 50 | 1-phenylethyl pentanoate 49 |
| 6[d] | hexyl hexanoate | isopropanol | 19 | 83 | isopropyl hexanoate 67 |
| 7 | hexyl hexanoate | 3-pentanol | 26 | 91 | 3-pentyl hexanoate 90 |
| 8 | pentyl pentanoate | cyclohexanol | 36 | 93 | cyclohexyl pentanoate 93 |
| 9 | pentyl pentanoate | cyclopentanol | 36 | 87 | cyclopentyl pentanoate 85 |
| 10 | pentyl pentanoate | 1-phenylethanol | 18 | 51 | 1-phenylethyl pentanoate 49 |
| 11 | pentyl pentanoate | 3-pentanol | 26 | 91 | 3-pentyl pentanoate 90 |

TABLE 8-continued

Acylation of alcohols catalyzed by the ruthenium complex 1[a]

| Entry | Ester | alcohol | Time (hrs) | Conv. of ester % | Yield % |
|---|---|---|---|---|---|
| 12 | 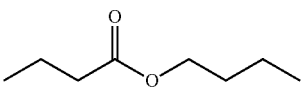 | 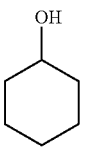 | 34 | 93 | 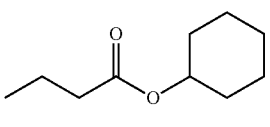 92 |
| 13 | 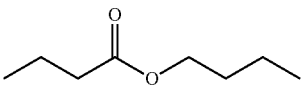 | 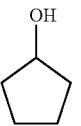 | 28 | 75 | 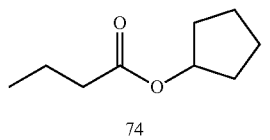 74 |
| 14 | 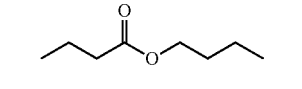 | 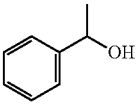 | 36 | 41 | 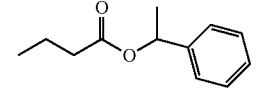 39 |
| 15 | 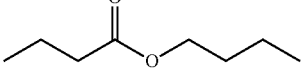 |  | 18 | 77 | 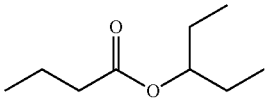 76 |
| 16[e] | 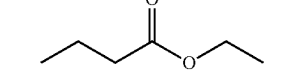 |  | 20 | 75 | 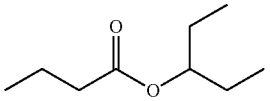 73 |
| 17 | 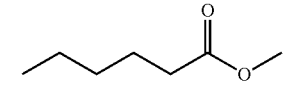 | 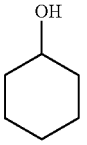 | 17 | 42 | 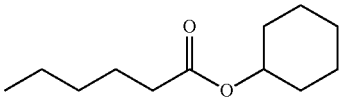 42 |

[a]Complex 1 (0.05 mmol), ester (5 mmol), alcohol (15 mmol) and toluene (3 ml) were refluxed/heated at an oil bath temperature of 135° C. under argon. Conversion of ester and yield of product were analyzed by GC using m-xylene or benzene as internal standards. A small amount of the secondary alcohol was converted into the corresponding ketone.
[b]Benzene was used as solvent. Efficient cooling of the reflux condenser is required to avoid losses of ethyl formate.
[c]1 (0.05 mmol), hexyl hexanoate (5 mmol), cyclohexanol (10 mmol) and toluene (3 ml) were used.
[d]a closed system and 3 ml of 2-propanol were used. An equivalent amount of 1-hexanol (67%) was also detected.
[e]m-xylene was used as solvent and benzene as internal standard.

Experimental Section

General Procedure for the Catalytic Acylation of Alcohols

Complex 1 (0.05 mmol), ester (5 mmol), alcohol (15 mmol) and toluene (3 mL) were added to Schlenk flask under an atmosphere of nitrogen in a glove box. The flask was equipped with a condenser and the solution was refluxed with stirring in an open system under argon for the specified time (Table 8). In the case of isopropanol, the reactions were performed in a closed system at 135° C. The reaction products were analyzed by GC-MS. After cooling to room temperature, m-xylene (1 mmol) or benzene (1 mmol) were added as internal standards to the reaction mixture and the products were quantitatively analyzed by GC using a Carboxen 1000 column on a HP 690 series GC system or HP-5 cross linked 5% PH ME Siloxane column (30m×0.32 mm×0.25 μm film thickness) on a HP 6890 series GC system. In the reaction of cyclohexanol and esters, evaporation of the solvent, followed by purification over basic alumina column chromatography afforded the pure transesters. $^1$H NMR of the products isolated from the catalysis was identical with the literature.

Example 8

Synthesis of Cyclic Dipeptides and Pyrazines from β-Aminoalcohols

A. Formation of Cyclic Dipeptides

Dehydrogenative coupling of β-aminoalcohols can lead to cyclic dipeptide formation (Scheme 20), except in case of R=H, Me (in which case linear polypeptides are the main products; in case of R=Me, a small amount of cyclic dipeptide is also formed).

Scheme 20

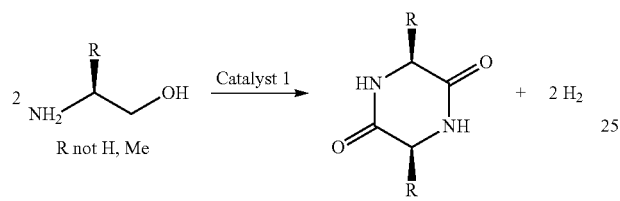

Refluxing a dioxane solution of (S)-2-amino-4-methylpentan-1-ol with complex 1 (1 mol %) led to 64% isolated yield of the cyclic dipeptide, 3,6-diisobutylpiperazine-2,5-dione 7b after workup (Table 9, entry 1). The product structure was confirmed by MS, NMR spectroscopies.

Upon refluxing a dioxane solution containing 2 mmol of (2S,3S)-2-amino-3-methylpentan-1-ol and 0.02 mmol of catalyst 1 for 19 hrs and cooling the reaction mixture, the solid product precipitated and was filtered off and dried under vacuum to give pure 3-(sec-butyl)-6-(sec-butyl)piperazine-2,5-dione 7c in 72% yield (Table 9, entry 2). The structure was confirmed by NMR and MS spectroscopies. Under the same conditions, cyclic peptidation of (S)-2-amino-3-methylbutan-1-ol led to 3,6-diisopropylpiperazine-2,5-dione 7d as an insoluble solid which separated from the reaction mixture and was isolated by filtration and dried under vacuum to give 78% of (3S,6S)-3,6-diisopropylpiperazine-2,5-dione 7d (Table 9, entry 3). The optical rotation of the pure product (−52°) was essentially the same as reported in the literature (−) 54°. Thus, under these experimental condition, no racemization took place.

The reaction of (S)-2-amino-3-phenylpropan-1-ol and 1 in refluxing dioxane led to 90% conversion with the isolation of the corresponding 3,6-dibenzylpiperazine-2,5-dione 7e in 72% yield (Table 9, entry 4). Reaction of 2-amino-2-methylpropan-1-ol under the same conditions yielded 100% conversion with isolation of the corresponding cyclic dipeptide 3,3,6,6-tetramethylpiperazine-2,5-dione 7f in 92% yield (Table 9, entry 5).

Tricyclic ring systems represent an important structural motif in many naturally existing alkaloids. Refluxing a dioxane solution of (S)-pyrrolidin-2-yl-methanol in the presence of catalyst 1 followed by solvent evaporation, hexane addition to the crude solid, and its isolation by filtration and washing with hexane led to octahydrodipyrrolo[1,2-a:1',2'-d]pyrazine-5,10-dione 7g in 99% isolated yield (Table 9, entry 6).

TABLE 9

Synthesis of cyclic dipeptides from β-aminoalcohols catalyzed by complex 1.

| Entry | Catalyst | Aminoalcohol | cyclic dipeptide | Isolated Yields (%) |
|---|---|---|---|---|
| 1 | 1 | | 7b | 64 |
| 2 | 1 | | 7c | 72 |
| 3 | 3 | | 7d | 87 |
| 4 | 3 | | 7e | 82 |

TABLE 9-continued

Synthesis of cyclic dipeptides from β-aminoalcohols catalyzed by complex 1.

| Entry | Catalyst | Aminoalcohol | cyclic dipeptide | Isolated Yields (%) |
|---|---|---|---|---|
| 5 | 1 | (structure) H₂N–C(CH₃)₂–CH₂OH | 7f | 92 |
| 6 | 1 | prolinol | 7g | 99 |

[a]Complex 1 or 3 (0.02 mmol), aminoalcohol (2 mmol) and dioxane (2 ml) were refluxed under argon (oil bath temperature of 135° C.) for 19 h.

B. Formation of Pyrazines

Pyrazines are biologically important organic compounds and their synthesis is of industrial significance. When the RuPNP complex 3 was used as catalyst, pyrazine compounds were obtained from β-amino alcohols (Scheme 21). Thus, a toluene solution of isoleucinol with complex 3 (1 mol %) was vigorously refluxed under argon for 24 hrs resulting in complete conversion of isoleucinol. The solvent was evaporated under vacuum and the residue was subjected to silica-gel column chromatography to afford 2,6-diiso-butyl pyrazine 8a in 53% yield (Table 10, Entry 1). $^1$H NMR exhibits the characteristic aromatic CH at 8.27 ppm and GC-MS confirms the respective molecular weight. The same reaction was also conducted by reflux under air using complex 3, resulting in 48% isolated yield of 8a. The similarity in yields of 8a under argon and under air indicates that air does not play a role as oxidant in the dehydrogenation of the presumed intermediate 1,4-dihydropyrazine to form the pyrazine. Significantly, no cyclic dipeptide was obtained under these conditions. Similar results were obtained with other aminoalcohols. Thus, toluene solutions of (S)-2-amino-3-methylbutan-1-ol, (S)-2-amino-4-methylpentan-1-ol, and (S)-2-amino-2-phenylethanol, were vigorously refluxed (bath temperature 165° C.) for 24 hrs while monitoring reaction progress by GC-MS. After complete disappearance of the amino alcohol, the crude product was purified by column chromatography to get the corresponding pyrazine products 8b-d (Table 10).

Scheme 21

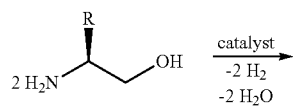

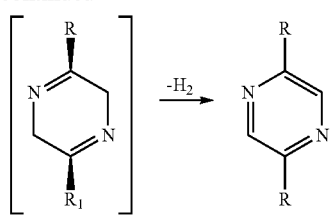

TABLE 10

Synthesis of pyrazines from β-aminoalcohols catalyzed by the ruthenium PNP complex 3[a]

| Entry | β-Aminoalcohol | Pyrazine | Isolated Yields (%) |
|---|---|---|---|
| 1 | 8a (isoleucinol) | 2,5-di-sec-butylpyrazine | 53 |
| 2 | (S)-2-amino-3-methylbutan-1-ol | 2,5-diisopropylpyrazine 8b | 35 |
| 3[b] | (S)-2-amino-4-methylpentan-1-ol | 2,5-diisobutylpyrazine 8c | 38 |

TABLE 10-continued

Synthesis of pyrazines from β-aminoalcohols catalyzed by the ruthenium PNP complex 3[a]

| Entry | β-Aminoalcohol | Pyrazine | Isolated Yields (%) |
|---|---|---|---|
| 4 | | 8d | 45 |
| 5[c] | | 8a | 48 |

[a]Complex 3 (0.02 mmol), aminoalcohol (2 mmol) and toluene (2 ml) were vigorously refluxed (oil bath temperature at 165° C. for 24 h).
[b]Heated in absence of solvent (oil bath temperature at 165° C.).
[c]Reaction performed under air.

General Procedure for the Synthesis of Cyclic Dipeptides from β-Aminoalcohols Complex 1 (0.02 mmol), aminoalcohol (2 mmol) and dioxane (2 mL) were added to Schlenk flask under an atmosphere of nitrogen in a glove box. The flask was equipped with a condenser and the solution was refluxed with stirring in an open system under argon for 19 hrs. The reaction products were analyzed by GC-MS on Agilent 7820A GC coupled with 5975 MSD system. The reaction mixture was cooled; the solid obtained was filtered off, washed with hexane and dried to give the pure cyclic dipeptide.

General Procedure for the Synthesis of Pyrazines from β-Aminoalcohols

Complex 3 (0.02 mmol), aminoalcohol (2 mmol) and toluene (2 mL) were added to Schlenk flask under an atmosphere of nitrogen in a glove box. The flask was equipped with a condenser and the solution was refluxed with stirring under argon in an open system for the 24 hrs. The reaction products were analyzed by GC-MS on Agilent 7820A GC coupled with 5975 MSD system. The solvent was evaporated from the reaction mixture and the crude product was subjected to silica-gel column chromatography using EtOAc:hexane to afford the pyrazine derivatives.

Characterization Data of Cyclic Dipeptides (3S,6S)-3,6-diisobutylpiperazine-2,5-dione

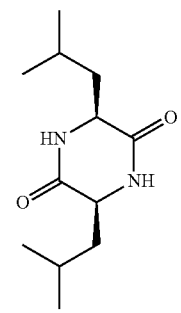 [SMILES: CC(C)C[C@@H]1NC(=O)[C@H](CC(C)C)NC1=O]

mp: 270-272° C.

$^1$H NMR (300 MHz, CD$_3$COOD): 0.84 (broad s, 12H, CH$_3$), 1.7 (broad s, 6H, CH$_2$, CH), 4.23 (broad s, 2H, NCH).

$^{13}$C{$^1$H}NMR (300 MHz, CDCl$_3$): 21.3 (CH$_3$), 21.6 (CH$_3$), 23.7 (CH$_3$), 23.8 (CH$_3$), 26.0 (CH), 26.2 (CH), 43.7 (CH$_2$), 46.4 (CH$_2$), 55.4 (NCH), 55.8 (NCH), 174.9 (C=O), 175.0 (C=O).

MS (ES$^+$, CH$_2$Cl$_2$+TFA): 227 (60%, M+H$^+$), 249 (100%, M+Na), 475 (70%, 2M+Na).

3-((R)-sec-butyl)-6-((S)-sec-butyl)piperazine-2,5-dione

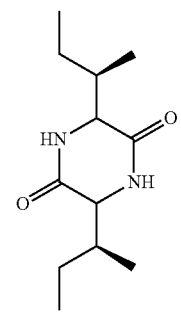 [SMILES: CC[C@@H](C)C1NC(=O)C([C@@H](C)CC)NC1=O]

mp: 276-280° C. (decompose)

$^1$H NMR (300 MHz, CDCl$_3$): 0.86-1.02 (m, 12H, CH$_3$), 1.19-1.47 (m, 4H, CH$_2$), 2.10-2.26 (m, 2H, CH$_2$), 3.91-4.07 (m, 2H, NCH), 6.11-6.31 (m, 2H, NH).

MS (ES⁺, CH₂Cl₂+TFA): 227 (40%, M+H), 244 (100%), 249 (40%, M+Na), 467 (80%), 475 (5%, 2M+Na).

(3S,6S)-3,6-diisopropylpiperazine-2,5-dione

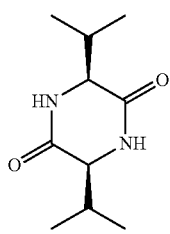

mp: 290-294° C. (decompose)

¹H NMR (300 MHz, CDCl₃ and CD₃COOD): 0.91 (d, J=6.6 Hz, 6H, CH₃), 1.01 (d, J=6.6 Hz, 6H, CH₃), 2.44-2.53 (m, 2H, CH), 4.11 (m, 2H, NCH).

¹³C{¹H}NMR (300 MHz, CDCl₃): 15.7 (CH₃), 18.2 (CH₃), 32.3 (CH), 59.8 (NCH), 171.2 (C=O).

MS (ES⁺, CH₂Cl₂+TFA): 199 (100%, M+H⁺), 221 (60%, M+Na), 419 (15%, 2M+Na).

[α]=−52° (c=0.01, AcOH)

(3S,6S)-3,6-dibenzylpiperazine-2,5-dione

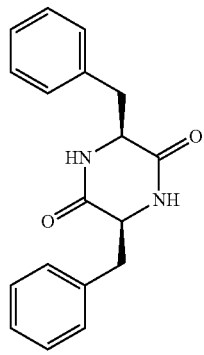 [SMILES: O=C1N[C@@H](Cc2ccccc2)C(=O)N[C@H]1Cc1ccccc1]

mp: 299-302° C. (decompose)

¹H NMR (300 MHz, CDCl₃ and CD₃COOD): 2.15-2.22 (m, 2H, CH₂), 2.95-3.01 (m, 2H, CH₂), 4.39-4.43 (m, 2H, NCH), 7.03 (d, J=6.9 Hz, 4H, =CH), 7.31-7.39 (m, 6H, =CH).

¹³C{¹H}NMR (300 MHz, CD₃COOD): 39.6 (CH₂), 56.2 (NCH), 128.4 (=CH), 129.4 (=CH), 129.9 (=CH), 133.5 (quat-C), 169.9, 173.0 (C=O).

MS (ES⁺, CH₂Cl₂+TFA): 295 (80%, M+H), 317 (100%, M+Na), 611 (60%, 2M+Na).

3,3,6,6-tetramethylpiperazine-2,5-dione

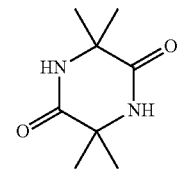

¹H NMR (300 MHz, DMSO-d₆): 1.30 (s, 12H, CH₃), 8.09 (s, 2H, NH).

¹³C{¹H}NMR (300 MHz, DMSO-d₆): 28.6 (CH₃), 55.7 (quat-C), 170.2 (C=O).

MS (ES⁺): 170 (100%, M⁺), 192 (30%), 200 (25%).

(5aS,10aS)-octahydrodipyrrolo[1,2-a:1',2'-d]pyrazine-5,10-dione

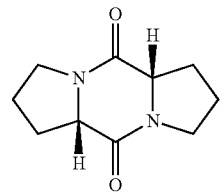 [SMILES: O=C1[C@@H]2CCCN2C(=O)[C@@H]2CCCN12]

mp: 146-148° C.

¹H NMR (300 MHz, CDCl₃): 1.88-2.33 (m, 8H, CH₂), 3.49-3.54 (m, 4H, NCH₂), 4.16 (t, 2H, NCH).

¹³C{¹H}NMR (300 MHz, CDCl₃): 23.3 (CH₂), 27.6 (CH₂), 45.1 (NCH₂), 60.5 (NCH), 166.3 (C=O).

MS (ES⁺): 194 (70%, M⁺), 216 (100%, M+Na−1), 217 (10%, M+Na).

Characterization Data of Pyrazines 2,5-di-sec-butylpyrazine

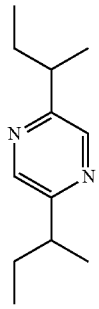

¹H NMR (300 MHz, CDCl₃): 0.77 (t, 6H, CH₃, J=7.2 Hz), 1.22 (d, 6H, CH₃, J=6.9 Hz), 1.52-1.74 (m, 4H, CH₂), 2.68-2.76 (m, 2H, CH), 8.27 (s, 2H, =CH).

$^{13}C\{^1H\}$ NMR (300 MHz, CDCl$_3$): 11.6 (CH$_3$), 19.6 (CH$_3$), 29.3 (CH$_2$), 40.2 (CH), 142.4 (=CH), 158.1 (quat-C).

2,5-diisopropylpyrazine

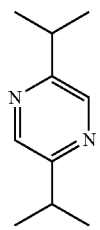

$^1$H NMR (300 MHz, CDCl$_3$): 1.23 (d, 12H, CH$_3$, J=7.2 Hz), 2.95-3.04 (m, 2H, CH), 8.30 (s, 2H, =CH).

$^{13}C\{^1H\}$ NMR (300 MHz, CDCl$_3$): 21.8 (CH$_3$), 33.1 (CH), 141.4 (=CH), 158.9 (quat-C).

2,5-diisobutylpyrazine

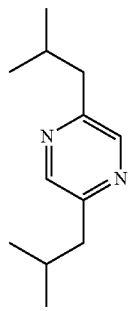

$^1$H NMR (300 MHz, CDCl$_3$): 0.94 (d, 12H, CH$_3$, J=6.6 Hz), 2.04-2.13 (m, 2H, CH), 2.63 (d, 4H, CH$_2$, J=7.2 Hz), 8.32 (s, J=6.9 Hz, 2H, =CH).

$^{13}C\{^1H\}$ NMR (300 MHz, CDCl$_3$): 21.9 (CH$_3$), 28.6 (CH), 43.6 (CH$_2$), 143.5 (=CH), 153.4 (quat-C).

2,5-diphenylpyrazine

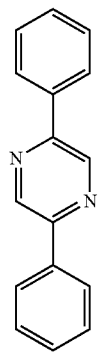

$^1$H NMR (300 MHz, CDCl$_3$): 7.48-7.57 (m, 6H, =CH$_3$), 8.07-8.10 (m, 4H, =CH), 9.09 (s, 2H, =CH).

$^{13}C\{^1H\}$ NMR (300 MHz, CDCl$_3$): 126.8 (=CH), 129.1 (=CH), 129.7 (=CH), 136.3 (quat-C), 141.2 (=CH), 150.6 (quat-C).

Example 9

Catalytic Hydrogenation of Organic Carbonates (a) A 100 mL Fischer-Porter tube was charged under nitrogen with catalyst 1 (0.01 mmol), organic carbonate (10.0 mmol), and THF (2 mL). The Fischer-Porter tube was purged by three successive cycles of pressurization/venting with H$_2$ (30 psi), then pressurized with H2 (10 atm). The solution was heated at 110° C. (bath temperature) with stirring for 48 hrs. After cooling to ~5° C. (ice/water), the H$_2$ was vented carefully and the products were determined by GC.

(b) Complex 1 (4.5 mg, 0.01 mmol) and 1,4-dioxane (5 mL) were placed in a stainless-steel 100 mL Parr Instrument under glove box (nitrogen atm). A solution of dimethyl carbonate (1.50 g, 25 mmol) in 1,4-dioxane (15 mL) was added, and the Parr Apparatus was purged by three successive cycles of pressurization/venting with H2 (4 atm), then pressurized with H2 (40 or 60 atm), closed and placed in a heating pan with a thermostat at 145° C. with stirring. After the specified time, the reaction vessel was cooled in an ice/water bath and the excess H$_2$ was vented carefully and the products were determined by GC.

While certain embodiments of the invention have been illustrated and described, it will be clear that the invention is not limited to the embodiments described herein. Numerous modifications, changes, variations, substitutions and equivalents will be apparent to those skilled in the art without departing from the spirit and scope of the present invention as described by the claims, which follow.

REFERENCES AND NOTES

1. R. C. Larock, *Comprehensive Organic Transformations* (VCH, New York, ed. 2, 1999).
2. N, Sewald, H.-D. Jakubke, *Peptides: Chemistry and Biology* (Wiley-VCH, 2002).
3a. A. Greenberg, C. M. Breneman, J. F. Liebman, *The Amide Lingkage: Selected Structural Aspects in Chemistry, Biochemistry, and Material Science* (Wiley, New York, 2000).
3b. M. B. Smith, J. March, *Advanced Organic Chemistry* (Wiley, New York, ed. 5, 2001).
4. B. L. Bray, *Nat. Rev.* 2, 587-93 (2003).
5. M. B. Smith, *Compendium of Organic Synthetic Methods* (Wiley, 2001), Vol. 9, Pp 100-116.
6. C. J. Cobley, M. van den Heuvel, A. Abbadi, J. G. de Vries, *Tetrahedron Lett.* 41, 2467-2470 (2000).
7. S.-I. Murahashi, T. Naota, E. Saito, *J. Am. Chem. Soc.* 108, 7846-7847 (1986).
8. S.-I. Murahashi, S. Sasao, E. Saito, T. Naota, *J. Org. Chem.* 57, 2521-2523 (1992).
9. Y. Tamaru, Y. Yamada, Z. Yoshida, *Synthesis* 1983, 474-476 (1983).
10. A. Tillack, I. Rudloff, M. Beller, *Eur. J. Org. Chem.* 2001, 523-528 (2001).
11. W.-K. Chan, C.-M, Ho, M.-K. Wong, C.-M. Che, *J. Am. Chem. Soc.* 128, 14796-14797 (2006).
12. S. H. Cho, E. J. Yoo, I. Bae, S. Chang, *J. Am. Chem. Soc.* 127, 16046-16047 (2005).
13. M. P. Cassidy, J. Raushel, V. V. Fokin, *Angew. Chem. Int. Ed.* 45, 3154-3157 (2006).

14. Seyden-Penne, J. *Reductions by the Alumino and Borohydrides in Organic Synthesis;* 2nd ed.; Wiley-VCH: New York, 1997.
15. (a) Rylander, P. M. *Hydrogenation Methods*; Academic Press: London, 1985. (b) Hartwig, J. *Organotransition Metal Chemistry*; University Science Books: Sausalito, Calif., 2010; pp 651-655.
16. (a) Hirosawa, C.; Wakasa, N.; Fuchikami, T. *Tetrahedron, Lett.* 1996, 37, 6749. (b) Núñez Magro, A. A.; Eastham, G. R.; Cole-Hamilton, D. J. *Chem. Commun.* 2007, 3154. (c) Beamson, G.; Papworth, A. J.; Philipps, C.; Smith, A. M.; Whyman, R. *Adv. Synth. Catal.* 2010, 352, 869. (d) Beamson, G.; Papworth, A. J.; Philipps, C.; Smith, A. M.; Whyman, R. *J. Catal.* 2010, 269, 93.
17. (a) Fernandes, A. C.; Romao, C. C. *J. Mol. Catal. A.,* 2007, 272, 60. (b) Das, S.; Addis, D.; Zhou, S.; Junge, K.; Beller, M. *J. Am. Chem. Soc.* 2010, 132, 1770.
18. Ito, M.; Koo, L. W.; Himizu, A.; Kobayashi, C.; Sakaguchi, A.; Ikariya, T. *Angew. Chem. Int. Ed.* 2009, 48, 1324.
19. (a) Lawrence, S. A. *Amines: Synthesis, Properties and Applications*; Cambridge University Press: Cambridge, 2005. (b) Ricci, A. *Amino Group Chemistry: From Synthesis to the Life Sciences*; Wiley-VCH: Weinheim, 2008. (c) Kumara Swamy, K. C.; Bhuvan Kumar, N. N.; Balaraman, E.; Pavan Kumar, K. V. P. *Chem. Rev.* 2009, 109, 2551.
20. J. Zhang, G. Leitus, Y. Ben-David, D. Milstein, *J. Am. Chem. Soc.* 127, 10840-10841 (2005).
21. J. Zhang, M. Gandelman, L. J. W. Shimon, D. Milstein, *Dalton. Trans.* 2007, 107-113 (2007).
22. J. Zhang, M. Gandelman, L. J. W. Shimon, D. Milstein, *Organometallics* 23, 4026-4033 (2004).
23. J. Zhang, G. Leitus, Y. Ben-David, D. Milstein, *Angew. Chem. Int. Ed.* 45, 1113-1115 (2006).
24. M. Hudlický, *Oxidations in Organic Chemistry*, (ACS monograph 186, Washigton D.C., 1990), Pp 114-155.
25. 1-Butanol was acylated with amines using stoichiometric amount of imidazole (via carbonyl imidazole). Reaction time and yield were not reported. S. P. Rannard, N. J. Davis, *Org. Lett.* 2, 2117-2120 (2000).
26. For a procedure based on 3 separate reactions, involving aldehyde synthesis by alcohol dehydrogenation, reaction of the aldehyde with hydroxylamine hydrochloride to form an oxime, and rearrangement of the oxime to an amine, see N. A. Owston, A. J. Parker, J. M. J. Williams, *Org. Lett.* 9, 73-75 (2007).
27. In the presence of an excess of a sacrificial hydrogen acceptor, ruthenium catalyzed lactamization of amino alcohols with a total of 16 turnovers was reported: T. Naota, S.-I. Murahashi, *Synlett* 1991, 693-694 (1991).
28. Rh-catalyzed lactamization of aryl amino alcohols in the presence of base and hydrogen acceptor with a total of 20 turnovers: K. Fujita, Y. Takahashi, M. Owaki, K. Yamamoto, R. Yamaguchi *Org. Lett.* 6, 2785-2788 (2004).
29. See *Science* Online (www.Sciencemag.org/feature/data/xxxxxxx.shl) Material for detailed procedures.
30. Intermolecular formation of amides from ester and amines catalyzed by aluminium and tin reagents are known. M. B. Smith, *Compendium of Organic Synthetic Methods* (Wiley, 2001), Vol. 9, p 110.
31. E. Ben-Ari, G. Leitus, L. J. W. Shimon, D. Milstein, *J. Am. Chem. Soc.* 128, 15390-15391 (2006).
32. Ruthenium catalyzed alkylation of amines by alcohols was reported, see M. H. S. A. Hamid, J. M. J. Williams, *Chem. Commun.* 2007, 725-727 (2007).
33. Y. Watanabe, Y. Tsuji, H. Ige, Y. Ohsugi, T. Ohta, *J. Org. Chem.* 49, 3359-3363 (1984).
34. R. A. T. M. Abbenhuis, J. Boersma, G. van Koten, *J. Org. Chem.* 63, 4282-4290 (1998).
35. N. Ahmad, J. J. Levison, S. D. Robinson, M. F. Uttley, *Inorg. Synth.* 15, 45 (1974).
36. B. Horst, D. Lothar, F. Juergen, R. Siegfried, *Chem. Ber.* 95, 1832-1893 (1962).
37. J. C. Williams, A. E. McDermott, *J. Phys. Chem.* 102, 6248-6259 (1998).
38. Zeng, H.; Guan, Z. *J. Am. Chem. Soc.* 2011, 133, 1159.

What is claimed is:

1. A process for hydrogenating an amide to generate an alcohol and amine, which process comprises reacting the amide with molecular hydrogen ($H_2$), in the absence of a solvent or in a solvent system consisting of an organic solvent, in the presence of a Ruthenium complex represented by the structure of formula A1', A2' or A3':

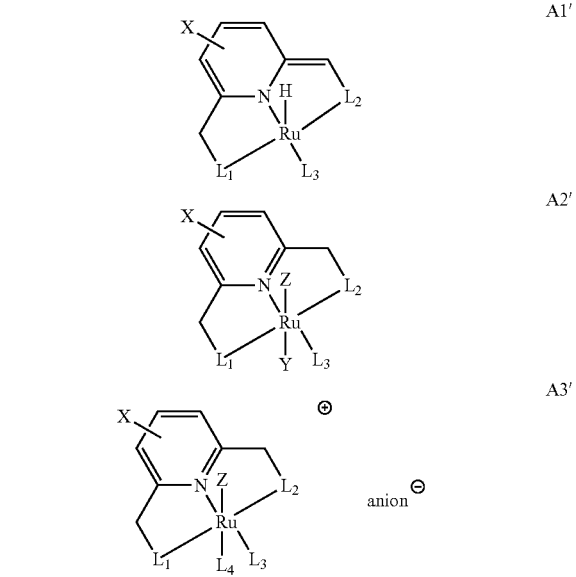

wherein
$L_1$ is $N(R)_2$;
$L_2$ is selected from the group consisting of nucleophilic carbene ($:CR_2$), $P(R_2)$, $P(OR)_2$, $N(R)_2$, imine, SR, SH, $S(=O)R$, heteroaryl wherein the heteroatom is selected from nitrogen and sulfur, $As(R_2)$, $Sb(R)_2$ and an N-heterocyclic carbene represented by the structure:

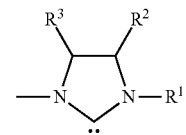

wherein each of R, $R^1$, $R^2$ and $R^3$ are independently selected from the group consisting of alkyl, cycloalkyl, aryl, alkylaryl, heterocyclyl and heteroaryl;
$L_3$ is a mono-dentate two-electron donor selected from the group consisting of CO, $P(R)_3$, $P(OR)_3$, $NO^+$, $As(R)_3$, $Sb(R)_3$, $S(R)_2$, nitrile (RCN) and isonitrile (RNC) wherein R is as defined above;
$L_4$ is absent or is $L_3$;

Y and Z are each independently H or an anionic ligand selected from the group consisting of halogen, OCOR, OCOCF$_3$, OSO$_2$R, OSO$_2$CF$_3$, CN, OH, OR, N(R$_2$), RS and SH; wherein R is as defined above;

X represents zero, one, two or three substituents selected from the group consisting of alkyl, aryl, halogen, nitro, amide, ester, cyano, alkoxy, cycloalkyl, alkylaryl, heterocyclyl, heteroaryl, an inorganic support and a polymeric moiety; and anion represents a group bearing a single negative charge wherein the process comprises the step of hydrogenating an amide represented by the formula R$^4$C(=O)—N—R$^5$R$^{5'}$ to an alcohol of formula R$^4$CH$_2$OH and amine of formula R$^5$R$^{5'}$NH:

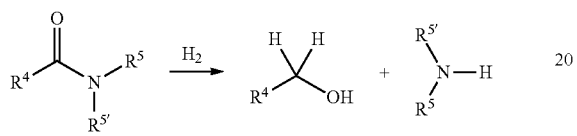

wherein R$^4$, R$^5$ and R$^{5'}$ are each independently selected from the group consisting of H, an unsubstituted or substituted alkyl, alkoxyalkyl, cycloalkyl, aryl, alkylaryl, heterocyclyl and heteroaryl.

2. The process of claim 1, wherein the process is conducted either with (a) Ruthenium complex A1' in the absence of a base; or (b) Ruthenium complex A2' or A3' in the presence of one or two equivalents of base relative to the amount of the Ruthenium complex.

3. The process of claim 1, wherein the complex is represented by the structure of formula 1:

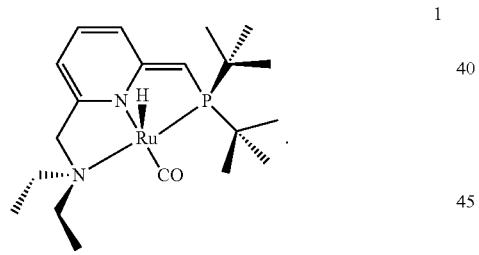

4. The process of claim 1, wherein the amide is selected from the group consisting of N-benzyl-2-methoxyacetamide, N-hexyl-2-methoxyacetamide, N-hexyl-3-methyloxetane-3-carboxamide, N-hexyl-2-furanylcarboxamide, N-benzylbenzamide, N-ethylacetamide, N-methylpropionamide, N-cyclohexyl-2-methoxyacetamide, N-phenylacetamide, N-phenylhexylamide, 2-methoxy-N-phenylacetamide, N-phenylbenzamide, Ethylenediamine-N,N'-(2-methoxyacetamide), N-hexanoylmorpholine, N-butanoylmorpholine, N-2-metoxyacetylpyrrolidine, N-formylmorpholine, N,N-dimethylformamide, N,N-diethylbenzamide, benzamide, 4-methylbenzamide, cyclohexanecarboxamide, hexanamide, acetamide, acrylamide and pivalamide.

5. The process of claim 1, wherein when the amide is a cyclic amide (lactam), the process results in an amino alcohol, or wherein the amide is a polyamide or a polypeptide.

6. A process for hydrogenating an organic carbonate represented by the formula R$^8$O—C(=O)—OR$^{8'}$ to the corresponding alcohols(s) and methanol:

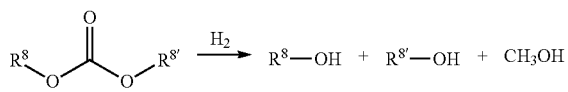

wherein R$^8$ and R$^{8'}$ are the same or different and are selected from the group consisting of an unsubstituted or substituted alkyl, alkoxyalkyl, cycloalkyl, aryl, alkylaryl, heterocyclyl and heteroaryl, which process comprises reacting the carbonate with molecular hydrogen (H$_2$), in the presence of a Ruthenium complex represented by the structure of formula A1', A2' or A3':

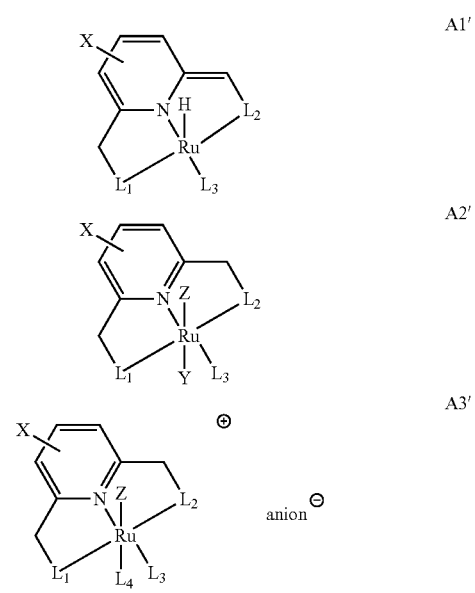

wherein

L$_1$ is N(R)$_2$;

L$_2$ is selected from the group consisting of nucleophilic carbene (:CR$_2$), P(R$_2$) P(OR)$_2$, N(R)$_2$, imine, SR, SH, S(=O)R, heteroaryl wherein the heteroatom is selected from nitrogen and sulfur, As(R$_2$), Sb(R)$_2$ and an N-heterocyclic carbene represented by the structure:

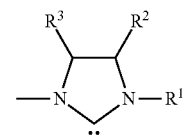

wherein each of R, R$^1$, R$^2$ and R$^3$ are independently selected from the group consisting of alkyl, cycloalkyl, aryl, alkylaryl, heterocyclyl and heteroaryl;

L$_3$ is a mono-dentate two-electron donor selected from the group consisting of CO, P(R)$_3$, P(OR)$_3$, NO$^+$, As(R)$_3$, Sb(R)$_3$, S(R)$_2$, nitrile (RCN) and isonitrile (RNC) wherein R is as defined above;

L$_4$ is absent or is L$_3$;

Y and Z are each independently H or an anionic ligand selected from the group consisting of halogen, OCOR, OCOCF$_3$ OSO$_2$R OSO$_2$CF$_3$, CN, OH, OR, N(R$_2$), RS and SH; wherein R is as defined above;

X represents zero, one, two or three substituents selected from the group consisting of alkyl, aryl, halogen, nitro, amide, ester, cyano, alkoxy, cycloalkyl, alkylaryl, heterocyclyl, heteroaryl, an inorganic support and a polymeric moiety; and anion represents a group bearing a single negative charge.

7. The process of claim 6, wherein the carbonate is dimethyl carbonate, diethyl carbonate, dipropyl carbonate or dibutyl carbonate.

8. A process for hydrogenating a carbamate represented by the formula $R^9O$—$C(=O)$—$NHR^{10}$ to the corresponding amine, alcohol and methanol:

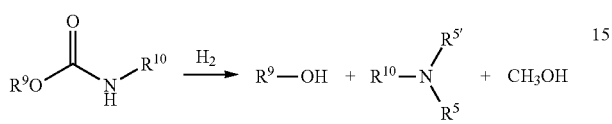

wherein $R^9$ is selected from the group consisting of an unsubstituted or substituted alkyl, alkoxyalkyl, cycloalkyl, aryl, alkylaryl, heterocyclyl and heteroaryl; and $R^{10}$ is selected from the group consisting of H or an unsubstituted or substituted alkyl, alkoxyalkyl, cycloalkyl, aryl, alkylaryl, heterocyclyl and heteroaryl, which process comprises reacting the carbamate with molecular hydrogen ($H_2$), in the presence of a Ruthenium complex represented by the structure of formula A1', A2' or A3':

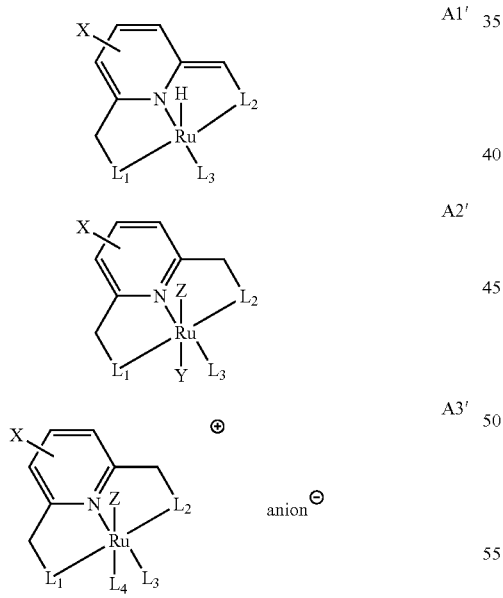

wherein $L_1$ is $N(R)_2$;

$L_2$ is selected from the group consisting of nucleophilic carbene (:$CR_2$), $P(R_2)$ $P(OR)_2$, $N(R)_2$, imine, SR, SH, S(=O)R, heteroaryl wherein the heteroatom is selected from nitrogen and sulfur, $As(R_2)$, $Sb(R)_2$ and an N-heterocyclic carbene represented by the structure:

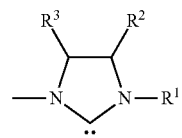

wherein each of R, $R^1$, $R^2$ and $R^3$ are independently selected from the group consisting of alkyl, cycloalkyl, aryl, alkylaryl, heterocyclyl and heteroaryl;

$L_3$ is a mono-dentate two-electron donor selected from the group consisting of CO, $P(R)_3$, $P(OR)_3$, $NO^+$, $As(R)_3$, $Sb(R)_3$, $S(R)_2$, nitrile (RCN) and isonitrile (RNC) wherein R is as defined above;

$L_4$ is absent or is $L_3$;

Y and Z are each independently H or an anionic ligand selected from the group consisting of halogen, OCOR, $OCOCF_3$ $OSO_2R$ $OSO_2CF_3$, CN, OH, OR, $N(R_2)$, RS and SH; wherein R is as defined above;

X represents zero, one, two or three substituents selected from the group consisting of alkyl, aryl, halogen, nitro, amide, ester, cyano, alkoxy, cycloalkyl, alkylaryl, heterocyclyl, heteroaryl, an inorganic support and a polymeric moiety; and anion represents a group bearing a single negative charge.

9. The process of claim 8, wherein the carbamate is methyl benzylcarbamate or methyl 4-methoxybenzylcarbamate.

10. A process for hydrogenating a urea compound to the corresponding amine and methanol:

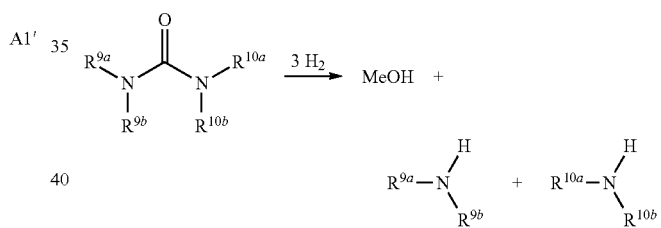

wherein each of $R^{9a}$ and $R^{10a}$, which may be the same or different, is selected from the group consisting of an unsubstituted or substituted alkyl, alkoxyalkyl, cycloalkyl, aryl, alkylaryl, and heterocyclyl, and each of $R^{9b}$ and $R^{10b}$, which may be the same or different, is selected from the group consisting of H, an unsubstituted or substituted alkyl, alkoxyalkyl, cycloalkyl, aryl, alkylaryl, and heterocyclyl; or wherein at least one of $R^{9a}$ and $R^{10a}$, and/or $R^{9b}$ and $R^{10b}$ together with the nitrogen to which they are attached form a heterocyclic ring, which process comprises reacting the urea compound with molecular hydrogen ($H_2$), in the presence of a Ruthenium complex represented by the structure of formula A1', A2' or A3':

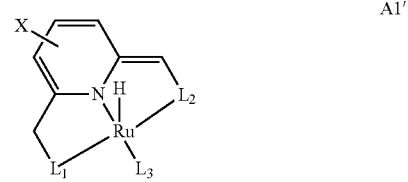

-continued

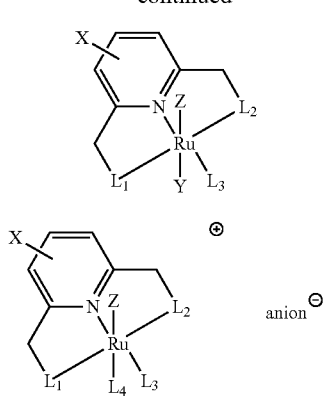

wherein
L₁ is N(R)₂;
L₂ is selected from the group consisting of nucleophilic carbene (:CR₂), P(R₂) P(OR)₂, N(R)₂, imine, SR, SH, S(=O)R, heteroaryl wherein the heteroatom is selected from nitrogen and sulfur, As(R₂), Sb(R)₂ and an N-heterocyclic carbene represented by the structure:

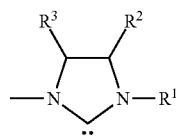

wherein each of R, R¹, R² and R³ are independently selected from the group consisting of alkyl, cycloalkyl, aryl, alkylaryl, heterocyclyl and heteroaryl;
L₃ is a mono-dentate two-electron donor selected from the group consisting of CO, P(R)₃, P(OR)₃, NO⁺, As(R)₃, Sb(R)₃, S(R)₂, nitrile (RCN) and isonitrile (RNC) wherein R is as defined above;
L₄ is absent or is L₃;
Y and Z are each independently H or an anionic ligand selected from the group consisting of halogen, OCOR, OCOCF₃ OSO₂R OSO₂CF₃, CN, OH, OR, N(R₂), RS and SH; wherein R is as defined above;
X represents zero, one, two or three substituents selected from the group consisting of alkyl, aryl, halogen, nitro, amide, ester, cyano, alkoxy, cycloalkyl, alkylaryl, heterocyclyl, heteroaryl, an inorganic support and a polymeric moiety; and
anion represents a group bearing a single negative charge.

11. The process of claim 10, wherein the urea compound is selected from the group consisting of 1,3-dimethylurea, 1,3-dipropylurea, 1,3-dihexylurea, 1,3-bis(2-methoxyethyl)urea, 1,3-dicyclohexylurea, 1,3-dibenzylurea, 1,3-bis(4-methylbenzyl)urea, 1,3-bis(4-methylbenzyl)urea, 1,3-diphenylurea, 1,3-bis(4-(tert-butyl)phenyl)urea, 1,1,3,3-tetramethylurea, and di(piperidin-1-yl)methanone.

12. The process of claim 6, wherein the carbonate is a polycarbonate.

13. The process of claim 1, wherein the process is conducted in an organic solvent selected from the group consisting of benzene, toluene, o-, m- or p-xylene, mesitylene (1,3, 5-trimethyl benzene), dioxane, THF, DME, anisole and cyclohexane.

14. The process of claim 6, wherein the process is conducted either with (a) Ruthenium complex A1' in the absence of a base; or (b) Ruthenium complex A2' or A3' in the presence of one or two equivalents of base relative to the amount of the Ruthenium complex.

15. The process of claim 8, wherein the process is conducted either with (a) Ruthenium complex A1' in the absence of a base; or (b) Ruthenium complex A2' or A3' in the presence of one or two equivalents of base relative to the amount of the Ruthenium complex.

16. The process of claim 10, wherein the process is conducted either with (a) Ruthenium complex A1' in the absence of a base; or (b) Ruthenium complex A2' or A3' in the presence of one or two equivalents of base relative to the amount of the Ruthenium complex.

17. The process of claim 6, wherein the complex is represented by the structure of formula 1:

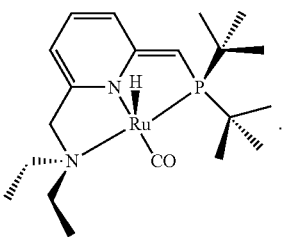

18. The process of claim 8, wherein the complex is represented by the structure of formula 1:

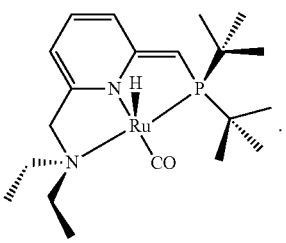

19. The process of claim 10, wherein the complex is represented by the structure of formula 1:

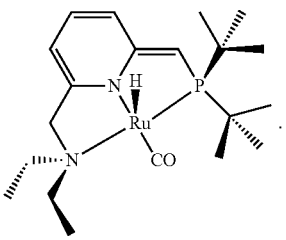

20. The process of claim 12, wherein the polycarbonate is polypropylene carbonate.

21. The process of claim 8, wherein the carbamate is a polycarbamate.

22. The process of claim 10, wherein the urea compound is a polyurea.

* * * * *